United States Patent
Lu

(10) Patent No.: US 7,968,725 B2
(45) Date of Patent: Jun. 28, 2011

(54) PYRIDINYL MODULATORS OF γ-SECRETASE

(75) Inventor: Tianbao Lu, Churchville, PA (US)

(73) Assignee: Janssen Pharmaceutica N.V., Beerse (BE)

( * ) Notice: Subject to any disclaimer, the term of this patent is extended or adjusted under 35 U.S.C. 154(b) by 0 days.

(21) Appl. No.: 12/478,820

(22) Filed: Jun. 5, 2009

(65) Prior Publication Data

US 2010/0022583 A1    Jan. 28, 2010

Related U.S. Application Data

(60) Provisional application No. 61/082,586, filed on Jul. 22, 2008.

(51) Int. Cl.
*C07D 213/55* (2006.01)
*A01N 43/40* (2006.01)

(52) U.S. Cl. ........................................ 546/342; 514/277
(58) Field of Classification Search .................. 546/342; 514/277
See application file for complete search history.

(56) References Cited

U.S. PATENT DOCUMENTS

2002/0128319 A1    9/2002    Koo et al.

FOREIGN PATENT DOCUMENTS

| WO | WO 01/78721 A1 | 10/2001 |
| WO | WO 03/008635 A2 | 1/2003 |
| WO | WO 2006/008558 A1 | 1/2006 |

OTHER PUBLICATIONS

West, Anthony R., Solid State Chemistry and its Applications, Wiley, New York, 1988, pp. 358 & 365.*
Hcaplus 1974:47782 abstract, "Pyrylium salts from pyrones and some organometallic compounds", Krivun et. al., 1973.*
Wilson et. al., "Preparation of terphenylcarboxylates for treatment of Alzheimer's disease", Hcaplus 2007:1201441, 2007.*
Patani et. al., "Bioisosterism: A Rational Approach in Drug Design", Chem. Rev. 1996, 96, pp. 3147-3176.*
Buchwald, H., et al. "Long-Term, Continuous Intravenous Heparin Administration by an Implantable Infusion Pump in Ambulatory Patients with Recurrent Venous Thrombosis", Surgery 88, p. 507 (1980).
During, M., et al. "Controlled Release of Dopamine from a Polymeric Brain Implant: In Vivo Characterization", Ann. Neurol. 25, p. 351 (1989).
Eriksen, J., et al. "NSAIDs and Enanatiomers of Flurbiprofen Target Gamma-Secretase and Lower A-beta-42 in vivo", Journal of Clinical Investigation, New York, NY US vol. 112, No. 3, (2003), XP002311406.
Evans, D., et al. "Synthesis of Diaryl Ethers through the Cooper-Promoted arylation of Phenols with Arylbornic Acids. An Expedient Synthesis of Thyroxine", Tetrahedron Letter 39 (1998) 2937-2940.

Frautschy, S., et al. "Microglial Response to Amyloid Plaques in APPsw Transgenic Mice", Am. J. of Pathology, VI. 52, No. 1 p. 307 (1998).
Howard, M., et al. "Acute Subdural Hematomas: An Age-Dependent Clinical Entity", J. Neurosurgery, vol. 71, p. 858 (1989).
Hsiao, K., et al. "Correlative Memory Deficits, Aβ Elevation and Amyloid Plaques in Transgenic Mice", Science 274, p. 99 (1996).
Ida, N., et al. "Analysis of Heterogeneous βA4 Peptides in Human Cerebrospinal Fluid and Blood by a Newly Developed Sensitive Western Blot Assay", J. Biol. Chem. 271, p. 22908 (1996).
Irizarry, M., et al. "APP$_{sw}$ Transgenic Mice Develop Age-Related Aβ Deposits and Neuropil Abnormalities, but no Neuronal Loss in CA1", J. of Neuropathology and Experimental Neurology, vol. 56(9), p. 965 (1997).
Jensen, M., et al. "Quantification of Alzheimer Amyloid Peptides Ending at Residues 40 and 42 by Novel ELISA Systems", Mol. Med. 6 p. 291 (2000).
Kaminski, T., et al. "Side-Chain Retention During Lithiation of 4-Picoline and 3,4-Lutidine: Easy Access to Molecular Diversity in Pyridine Series", European J. Organic Chemistry (2003) p. 3855-3860.
Kawarabayahsi, T., et al. "Age-Dependent Changes in Brain, CSF, and Plasma Amyloid β Protein in the Tg2576 Transgenic Mouse Model of Alzheimer's Disease", J. Neurosci. 21 p. 372 (2001).
Krivun, S., et al. "Pyrylium Salts from Pyrones and Some Organometallic Compounds", Chemistry of Heterocyclic Compounds, vol. 9 (1973) p. 1191-1194.
Langer, R., "New Methods of Drug Delivery", Science 249, p. 1527 (1990).
Langer and Peppas "Chemical and Physical Structure of Polymers as Carriers for Controlled Release of Bioactive Agents: A Review", Macromol. Chem. Phys. C23(1), 61-126 (1983).

(Continued)

*Primary Examiner* — Janet Andres
*Assistant Examiner* — Heidi Reese
(74) *Attorney, Agent, or Firm* — Woodcock Washburn LLP

(57) ABSTRACT

The present invention relates to compounds of Formula I as shown below, wherein the definitions of A, X, $R^1$, $R^2$, $R^3$, $R^4$, $R^5$, $R^6$, $R^7$, $R^8$, and $R^9$ are provided in the specification. Compounds of Formula I are useful for the treatment of diseases associated with γ-secretase activity, including Alzheimer's disease.

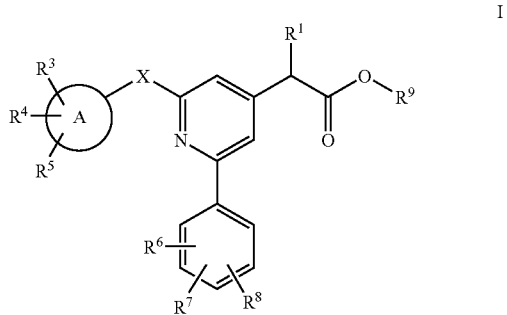

8 Claims, No Drawings

OTHER PUBLICATIONS

Larner, A., "Secretases as Therapeutic Targets in Alzheimer's Disease: Patents 2000-2004", Exp. Opinion Ther. Patents 14, p. 1403 (2004).

Lehman, J., et al. "Alterations in β-Amyloid Production and Deposition in Brain Regions of Two Transgenic Models", Neurobiol. Aging 24, p. 645 (2003).

Levy, R., et al. "Inhibition of Calcification of Bioprosthetic Heart Valves by Local Controlled Release Diphosphonate", Science 228, p. 190 (1985).

Lim, G., et al. Ibuprofen Effects on Alzheimer Pathology and Open Field Activity in APPsw Transgenic Mice, Neuroibol. Aging 22, p. 645 (2001).

Lim, G., et al. "Ibuprofen Suppresses Plaque Pathology and Open Field Activity in APPsw Transgenic Mice", Journal of Neuroscience, vol. 20(15), p. 5709 (2000).

Marjaux, E., et al. "γ-Secretase Inhibitors: Still in the Running as Alzheimer's Therapeutics", Drug Discovery Today: Therapeutics Strategies 1, p. 1 (2004).

Morihara, T., et al. "Selective Inhibition of Aβ42 Production b NSAID R-Enantiomer", J., Neurochem. 83, p. 1009 (2002).

Myers, A., et al. "Use of Pseudo Ephedrine as a Practical Chiral Auxiliary for Asymmetric Synthesis", Journal of American Chemical Society, 116 (20), p. 9361 (1994).

Peretto, D., et al. "Synthesis and Biological Activity of Fluriprofen Analogues as Selective Inhibitors of β-Amylid 1-42 Secretion", J. Med. Chem. 48 p. 5705 (2005).

Saudek, C., et al. "A Preliminary Trial of the Programmable Implantable Medication System for Insulin Delivery", N. Engl. J. Med. p. 321 (1989).

Schweisguth, F., et al. Regulation of Notch Signaling Activity, Curr. Biol. 14, p. R129 (2004).

Sefton, M., "Implantable Pumps", CRC Crit. Ref. Biomed. Eng. 14, p. 201 (1987).

Shimizu, K., et al. "Binding of Deltal, Jagged1, and Jagged2 to Notch2 Rapidly Induces Cleavage, Nuclear Translocation, and Hyperphosphorylation of Notch2", Mol. Cell. Biol. 20, p. 6913 (2000).

Steiner, H., "Uncovering γ-Sucretase", Curr. Alzheimer Research 1(3), p. 175 (2004).

Tanzi, R., et al. "Twenty Years of the Alzlheimer's Disease Amyloid Hypothesis: A Genetic Perspective", Cell, vol. 120, (2005) p. 545-555.

Vassar, R., et al. "β-Secretese Cleavage of Alzheimer's Amyloid Precursor Protein by the Transmembrane Aspartic Protease BACE", science 286, p. 735 (1999).

Wang, R., et al. "The Profile of Soluble Amyloid β Protein in Cultured Cell Media", J. Biol. Chem. 271 p. 31894 (1996).

Weggen, S., et al. "A Subset of NSAIDs Lower Amylidogenic Aβ42 Independently of Cyclooxygenase Activity", Nature 414, p. 212 (2001).

Xia, W., et al. "Preseilin 1 Regulates the Processing of β-Amyloid Precursor Protein C-Terminal Fragments and the Generation of Amyloid β-Protein in Endoplasmic Reticulum and Golgi", Biochemistry 3, 16465 (1998).

Yan, R., et al. "Membrane Anchored Aspartyl Protease with Alzheimer's Disease β Secretase Activity", Nature 402, p. 533 (1999).

\* cited by examiner

PYRIDINYL MODULATORS OF γ-SECRETASE

CROSS-REFERENCE TO RELATED APPLICATIONS

The present application claims the benefits of the filing of U.S. Provisional Application No. 61/082,586 filed Jul. 22, 2008. The complete disclosures of the aforementioned related patent applications are hereby incorporated herein by reference for all purposes.

FIELD OF THE INVENTION

The present invention relates to compounds of Formula I as shown below, wherein the definitions of A, X, $R^1$ $R^2$, $R^3$, $R^4$, $R^5$, $R^6$, $R^7$, $R^8$, and $R^9$ are provided in the specification. Compounds of Formula I are useful for the treatment of diseases associated with γ-secretase activity, including Alzheimer's disease.

BACKGROUND OF THE INVENTION

Alzheimer's Disease (AD) is a progressive neurodegenerative disorder marked by loss of memory, cognition, and behavioral stability. AD afflicts 6-10% of the population over age 65 and up to 50% over age 85. It is the leading cause of dementia and the third leading cause of death after cardiovascular disease and cancer. There is currently no effective treatment for AD. The total net cost related to AD in the U.S. exceeds $100 billion annually.

AD does not have a simple etiology, however, it has been associated with certain risk factors including (1) age, (2) family history (3) and head trauma; other factors include environmental toxins and low level of education. Specific neuropathological lesions in the limbic and cerebral cortices include intracellular neurofibrillary tangles consisting of hyperphosphorylated tau protein and the extracellular deposition of fibrillar aggregates of amyloid beta peptides (amyloid plaques). The major component of amyloid plaques are the amyloid beta (A-beta, Abeta or Aβ) peptides of various lengths. A variant thereof, which is the Aβ1-42-peptide (Abeta-42), is believed to be the major causative agent for amyloid formation. Another variant is the Aβ1-40-peptide (Abeta-40). Amyloid beta is the proteolytic product of a precursor protein, beta amyloid precursor protein (beta-APP or APP).

Familial, early onset autosomal dominant forms of AD have been linked to missense mutations in the β-amyloid precursor protein (β-APP or APP) and in the presenilin proteins 1 and 2. In some patients, late onset forms of AD have been correlated with a specific allele of the apolipoprotein E (ApoE) gene, and, more recently, the finding of a mutation in alpha2-macroglobulin, which may be linked to at least 30% of the AD population. Despite this heterogeneity, all forms of AD exhibit similar pathological findings. Genetic analysis has provided the best clues for a logical therapeutic approach to AD. All mutations, found to date, affect the quantitative or qualitative production of the amyloidogenic peptides known as Abeta-peptides (Aβ), specifically Aβ42, and have given strong support to the "amyloid cascade hypothesis" of AD (Tanzi and Bertram, 2005, Cell 120, 545). The likely link between Aβ peptide generation and AD pathology emphasizes the need for a better understanding of the mechanisms of Aβ production and strongly warrants a therapeutic approach at modulating Aβ levels.

The release of Aβ peptides is modulated by at least two proteolytic activities referred to as β- and γ-secretase cleaving at the N-terminus (Met-Asp bond) and the C-terminus (residues 37-42) of the Aβ peptide, respectively. In the secretory pathway, there is evidence that β-secretase cleaves first, leading to the secretion of s-APPβ (sβ) and the retention of a 11 kDa membrane-bound carboxy terminal fragment (CTF). The latter is believed to give rise to Aβ peptides following cleavage by γ-secretase. The amount of the longer isoform, Aβ42, is selectively increased in patients carrying certain mutations in a particular protein (presenilin), and these mutations have been correlated with early-onset familial Alzheimer's disease. Therefore, Aβ42 is believed by many researchers to be the main culprit of the pathogenesis of Alzheimer's disease.

It has now become clear that the γ-secretase activity cannot be ascribed to a single particular protein, but is in fact associated with an assembly of different proteins.

The gamma-secretase activity resides within a multiprotein complex containing at least four components: the presenilin (PS) heterodimer, nicastrin, aph-1 and pen-2. The PS heterodimer consists of the amino- and carboxyterminal PS fragments generated by endoproteolysis of the precursor protein. The two aspartates of the catalytic site are at the interface of this heterodimer. It has recently been suggested that nicastrin serves as a gamma-secretase-substrate receptor. The functions of the other members of gamma-secretase are unknown, but they are all required for activity (Steiner, 2004. Curr. Alzheimer Research 1(3): 175-181).

Thus, although the molecular mechanism of the second cleavage-step has remained elusive until present, the γ-secretase-complex has become one of the prime targets in the search for compounds for the treatment of Alzheimer's disease.

Various strategies have been proposed for targeting gamma-secretase in Alzheimer's disease, ranging from targeting the catalytic site directly, developing substrate-specific inhibitors and modulators of gamma-secretase activity (Marjaux et al., 2004. Drug Discovery Today: Therapeutic Strategies, Volume 1, 1-6). Accordingly, a variety of compounds were described that have secretases as targets (Lamer, 2004. Secretases as therapeutics targets in Alzheimer's disease: patents 2000-2004. Expert Opin. Ther. Patents 14, 1403-1420.)

Indeed, this finding was recently supported by biochemical studies in which an effect of certain NSAIDs on γ-secretase was shown (Weggen et al (2001) Nature 414, 6860, 212 and WO 01/78721 and US 2002/0128319; Morihara et al (2002) J. Neurochem. 83, 1009; Eriksen (2003) J. Clin. Invest. 112, 440). Potential limitations for the use of NSAIDs to prevent or treat AD are their inhibition activity of Cox enzymes, which can lead to unwanted side effects, and their low CNS penetration (Peretto et al., 2005, J. Med. Chem. 48, 5705-5720).

Thus, there is a strong need for novel compounds which modulate γ-secretase activity thereby opening new avenues for the treatment of Alzheimer's disease.

The object of the present invention is to provide such compounds.

SUMMARY OF THE INVENTION

The invention comprises compounds having the general Formula (I)

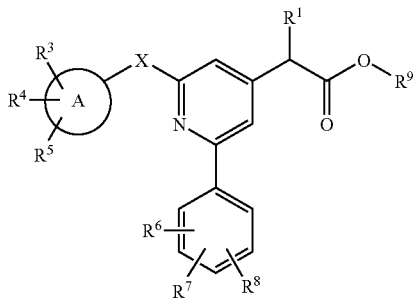

wherein
A is phenyl, pyridyl, pyrimidyl, pyridazyl, napthyl, biphenyl, quinolinyl, isoquinolinyl, quinazolinyl, or benzothiazolyl, alternatively, A is taken together with $R^3$, $R^4$, and $R^5$, and is selected from the group consisting of:

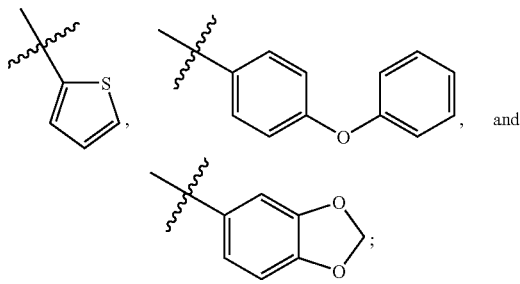

X is a direct bond, or —$NR^2$—;
  wherein $R^2$ is $C_{(1-5)}$alkyl or $C_{(1-5)}$alkenyl either of which is optionally substituted with cyclohexyl, heterocyclyl, or up to three substituents independently selected from the group consisting of F, Cl, Br, I, and $CF_3$;
$R^1$ is H, $C_{(1-5)}$alkyl, or $C_{(1-5)}$alkenyl; wherein said alkyl and alkenyl groups are optionally substituted with up to three substituents independently selected from the group consisting of F, Cl, Br, I and $CF_3$;
$R^3$, and $R^6$ are independently selected from the group consisting of H, F, Cl, Br, I, CN, OH, $C(O)N(C_{(1-4)}alkyl)_2$, $S(O)_2C_{(1-4)}alkyl$, $SO_2N(C_{(1-4)}alkyl)_2$, $S(O)N(C_{(1-4)}alkyl)_2$, $N(C_{(1-4)}alkyl)S(O)_2C_{(1-4)}alkyl$, $N(C_{(1-4)}alkyl)S(O)C_{(1-4)}alkyl$, $S(O)_2C_{(1-4)}alkyl$, $N(C_{(1-4)}alkyl)S(O)_2N(C_{(1-4)}alkyl)_2$, $SC_{(1-4)}alkyl$, $N(C_{(1-4)}alkyl)_2$, $N(C_{(1-4)}alkyl)C(O)C_{(1-4)}alkyl$, $N(C_{(1-4)}alkyl)C(O)N(C_{(1-4)}alkyl)_2$, $N(C_{(1-4)}alkyl)C(O)OC_{(1-4)}alkyl$, $OC(O)N(C_{(1-4)}alkyl)_2$, $C(O)C_{(1-4)}alkyl$, substituted and unsubstituted $C_1$-$C_4$-alkyl and substituted and unsubstituted $C_1$-$C_4$-alkoxy, and wherein the substituents of both groups $C_1$-$C_4$-alkyl and $C_1$-$C_4$-alkoxy are selected from the group consisting of F, Cl, Br, I, and $CF_3$;
$R^4$, $R^5$, $R^7$, and $R^8$ are independently selected from the group consisting of $CF_3$, $OCF_3$, H, F, Cl, —$OC_{(1-4)}$alkyl, $C_{(1-4)}$alkyl, —$SO_2CH_3$, and CN;
$R^9$ is H, $C_{(1-5)}$alkyl, or $C_{(1-5)}$alkenyl; wherein said alkyl and alkenyl groups are optionally substituted with up to three substituents independently selected from the group consisting of F, Cl, Br, I and $CF_3$
and solvates, hydrates, esters, and pharmaceutically acceptable salts thereof.

DETAILED DESCRIPTION OF THE INVENTION

The invention comprises compounds having the general Formula (I)

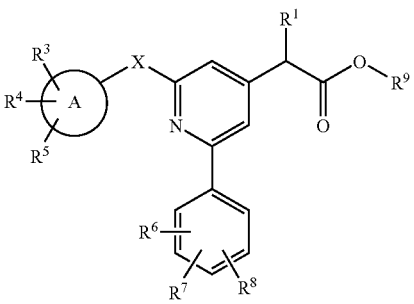

wherein
A is phenyl, pyridyl, pyrimidyl, pyridazyl, napthyl, biphenyl, quinolinyl, isoquinolinyl, quinazolinyl, or benzothiazolyl, alternatively, A is taken together with $R^3$, $R^4$, and $R^5$, and is selected from the group consisting of:

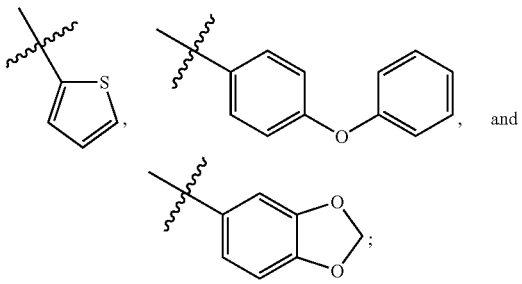

X is a direct bond, or —$NR^2$—;
  wherein $R^2$ is $C_{(1-5)}$alkyl or $C_{(1-5)}$alkenyl either of which is optionally substituted with cyclohexyl, heterocyclyl, or up to three substituents independently selected from the group consisting of F, Cl, Br, I, and $CF_3$;
$R^1$ is H, $C_{(1-5)}$alkyl, or $C_{(1-5)}$alkenyl; wherein said alkyl and alkenyl groups are optionally substituted with up to three substituents independently selected from the group consisting of F, Cl, Br, I and $CF_3$;
$R^3$, and $R^6$ are independently selected from the group consisting of H, F, Cl, Br, I, CN, OH, $C(O)N(C_{(1-4)}alkyl)_2$, $S(O)_2C_{(1-4)}alkyl$, $SO_2N(C_{(1-4)}alkyl)_2$, $S(O)N(C_{(1-4)}alkyl)_2$, $N(C_{(1-4)}alkyl)S(O)_2C_{(1-4)}alkyl$, $N(C_{(1-4)}alkyl)S(O)C_{(1-4)}alkyl$, $S(O)_2C_{(1-4)}alkyl$, $N(C_{(1-4)}alkyl)S(O)_2N(C_{(1-4)}alkyl)_2$, $SC_{(1-4)}alkyl$, $N(C_{(1-4)}alkyl)_2$, $N(C_{(1-4)}alkyl)C(O)C_{(1-4)}alkyl$, $N(C_{(1-4)}alkyl)C(O)N(C_{(1-4)}alkyl)_2$, $N(C_{(1-4)}alkyl)C(O)OC_{(1-4)}alkyl$, $OC(O)N(C_{(1-4)}alkyl)_2$, $C(O)C_{(1-4)}alkyl$, substituted and unsubstituted $C_1$-$C_4$-alkyl and substituted and unsubstituted $C_1$-$C_4$-alkoxy, and wherein the substituents of both groups $C_1$-$C_4$-alkyl and $C_1$-$C_4$-alkoxy are selected from the group consisting of F, Cl, Br, I, and $CF_3$;
$R^4$, $R^5$, $R^7$, and $R^8$ are independently selected from the group consisting of $CF_3$, $OCF_3$, H, F, Cl, —$OC_{(1-4)}$alkyl, $C_{(1-4)}$alkyl, —$SO_2CH_3$, and CN;
$R^9$ is H, $C_{(1-5)}$alkyl, or $C_{(1-5)}$alkenyl; wherein said alkyl and alkenyl groups are optionally substituted with up to three substituents independently selected from the group consisting of F, Cl, Br, I and $CF_3$ and solvates, hydrates, esters, and pharmaceutically acceptable salts thereof.

In another embodiment of the invention:

A is phenyl, pyridyl, napthyl, biphenyl, quinolinyl, isoquinolinyl, or benzothiazolyl, alternatively, A is taken together with $R^3$, $R^4$, and $R^5$, and is selected from the group consisting of:

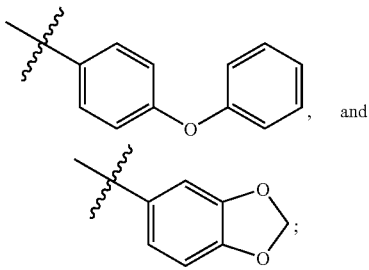

$R^1$ is H, $C_{(1-5)}$alkyl, or $C_{(1-5)}$alkenyl;

X is a direct bond, or —$NR^2$—;
  wherein $R^2$ is $C_{(1-5)}$alkyl optionally substituted with $C_{(1-6)}$cycloalkyl or $C_{(1-6)}$heterocyclyl;

$R^3$ is H, $CF_3$, F, $OCF_3$, $C_{(1-4)}$alkyl, —$OC_{(1-4)}$alkyl, or —$SO_2CH_3$;

$R^4$ is H, $CF_3$, F, $OCF_3$, $C_{(1-4)}$alkyl, —$OC_{(1-4)}$alkyl, or —$SO_2CH_3$;

$R^5$ is H, $CF_3$, F, $OCF_3$, $C_{(1-4)}$alkyl, —$OC_{(1-4)}$alkyl, or —$SO_2CH_3$;

$R^6$ is H, F, $OCF_3$, or $CF_3$;

$R^7$ is H, F, $OCF_3$, or $CF_3$;

$R^8$ is H, F, $OCF_3$, or $CF_3$;

$R^9$ is H, or $C_{(1-4)}$alkyl;

and solvates, hydrates, esters, and pharmaceutically acceptable salts thereof.

In another embodiment of the invention:

A is phenyl, pyridyl, napthyl, or biphenyl, alternatively, A is taken together with $R^3$, $R^4$, and $R^5$, and is selected from the group consisting of:

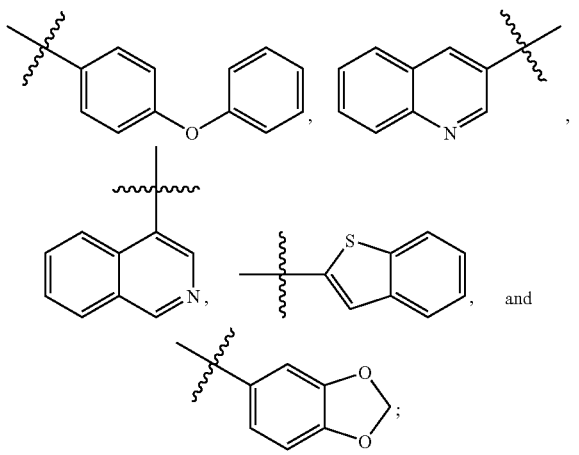

$R^1$ is H, $C_{(1-4)}$alkyl, or $C_{(1-4)}$alkenyl;

X is a direct bond, or —$NR^2$—;
  wherein $R^2$ is $C_{(1-5)}$alkyl optionally substituted with cyclohexyl or piperidinyl;

$R^3$ is $CF_3$, F, $OCF_3$, $C_{(1-4)}$alkyl, —$OC_{(1-4)}$alkyl, or —$SO_2CH_3$;

$R^4$ is H, F, $OCF_3$, or $CF_3$;

$R^5$ is H, F, $OCF_3$, or $CF_3$;

$R^6$ is F, or $CF_3$;

$R^7$ is H, or F;

$R^8$ is H, or F;

$R^9$ is H;

and solvates, hydrates, esters, and pharmaceutically acceptable salts thereof.

In another embodiment of the invention:

A is phenyl or pyridyl, alternatively, A is taken together with $R^3$, $R^4$, and $R^5$, and is selected from the group consisting of:

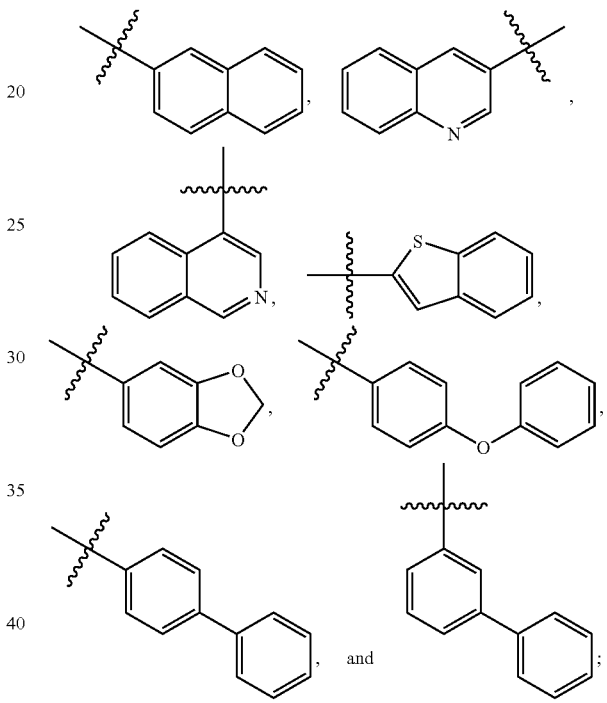

$R^1$ is selected from the group consisting of H, —$CH_2CH(CH_3)_2$, and 2-methyl 1-propen-3-yl;

X is a direct bond, or —$NR^2$—;
  wherein $R^2$ is selected from the group consisting of alkyl selected from the group consisting of —$CH_2CH(CH_3)_2$, —$CH_2CH_2CH(CH_3)_2$, and ethyl, wherein said ethyl is substituted with cyclohexyl or piperidinyl;

$R^3$ is $CF_3$, F, $OCF_3$, $OCH_3$, $CH_3$, isopropyl, tert-butyl, —$OCH_2CH(CH_3)_2$, or —$SO_2CH_3$;

$R^4$ is H, F, or $CF_3$;

$R^5$ is H, or F;

$R^6$ is $CF_3$;

$R^7$ is H;

$R^8$ is H;

$R^9$ is H;

and solvates, hydrates, esters, and pharmaceutically acceptable salts thereof.

In another embodiment of the invention:

A is taken together with $R^3$, $R^4$, and $R^5$, and is selected from the group consisting of:

R[1] is selected from the group consisting of H, —CH$_2$CH(CH$_3$)$_2$, and 2-methyl 1-propen-3-yl;

X is a direct bond, or —NR[1]—;

wherein R[2] is selected from the group consisting of alkyl selected from the group consisting of —CH$_2$CH(CH$_3$)$_2$, —CH$_2$CH$_2$CH(CH$_3$)$_2$, and ethyl, wherein said ethyl is substituted with cyclohexyl or piperidinyl;

R[6] is CF$_3$;

R[7] is H;

R[8] is H;

R[9] is H;

and solvates, hydrates, esters, and pharmaceutically acceptable salts thereof.

Another embodiment of the invention comprises a compound selected from the group consisting of:

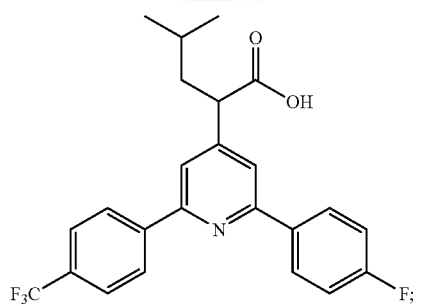
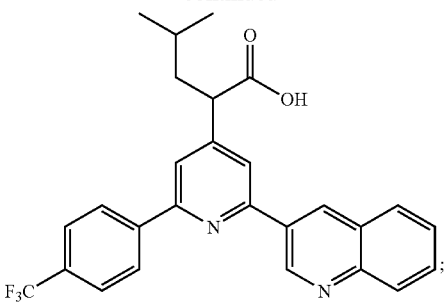

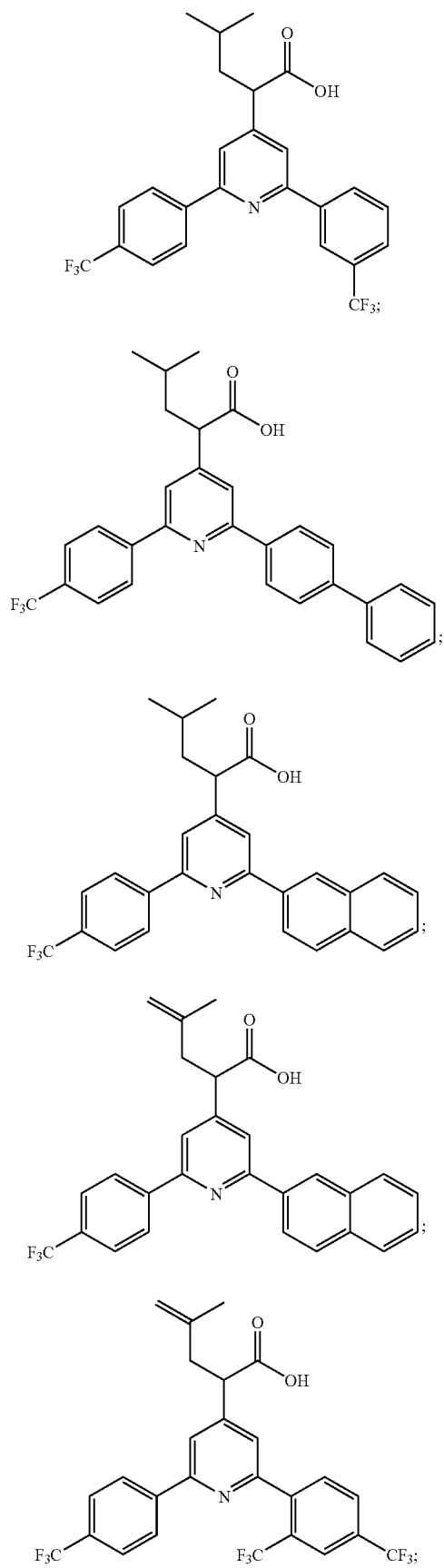
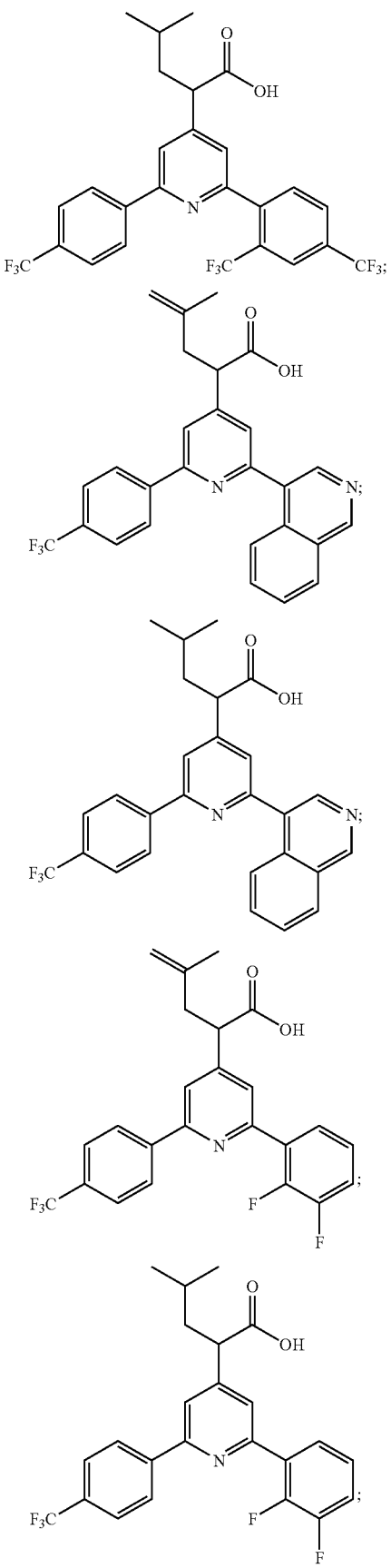

-continued
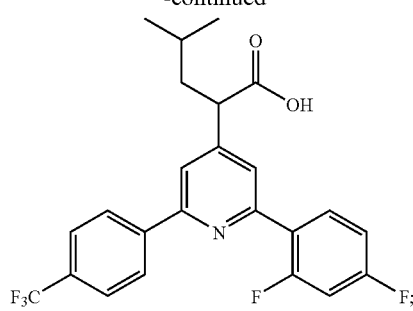
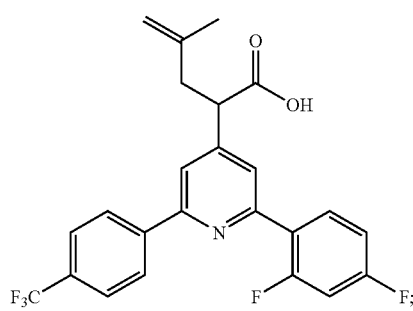
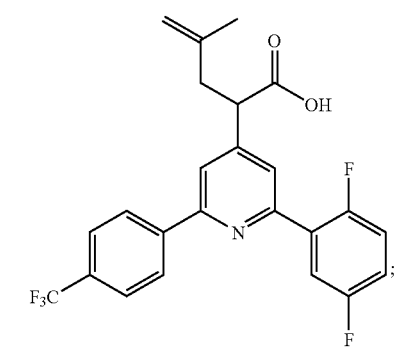
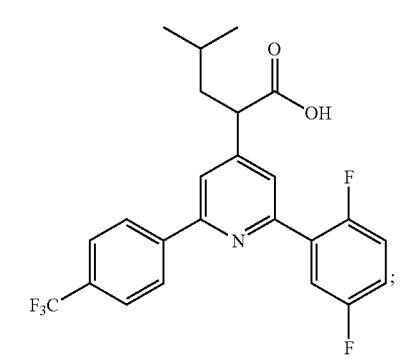
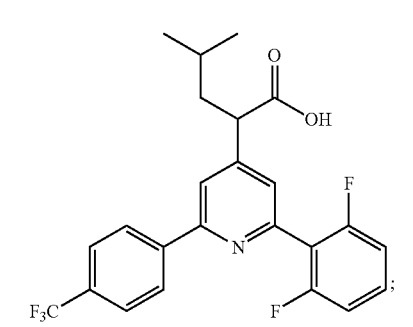
-continued
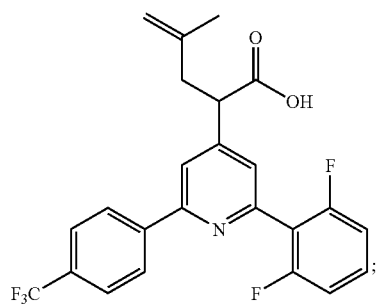
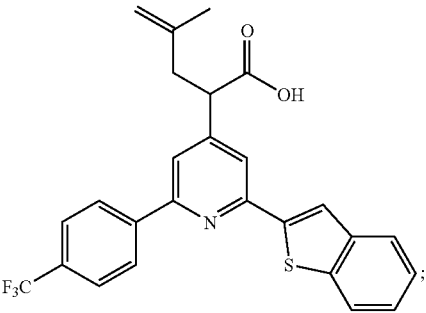
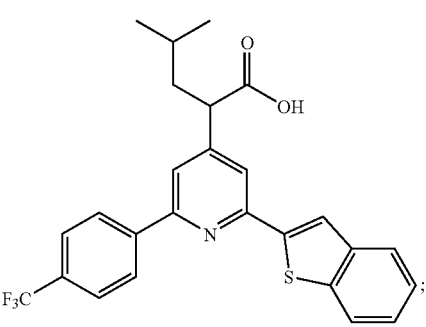
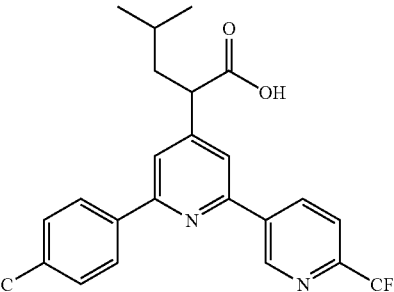
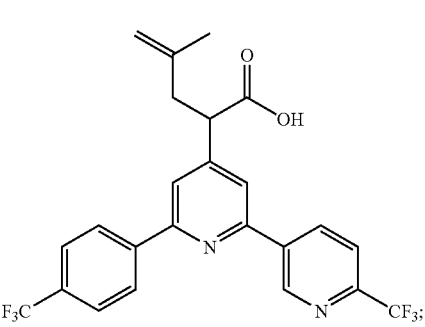

15
-continued
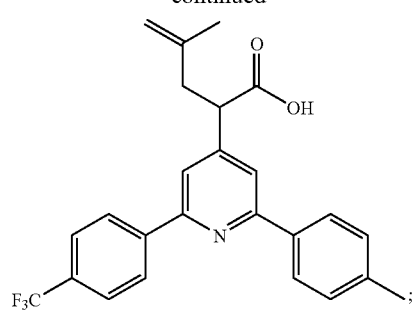
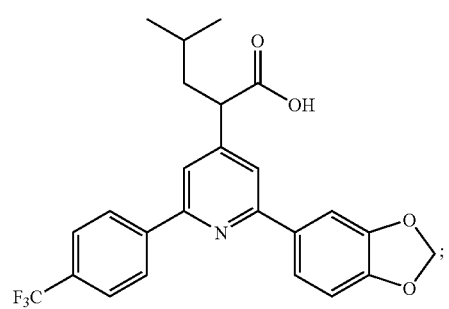
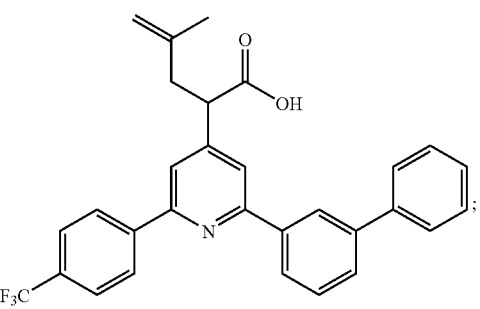
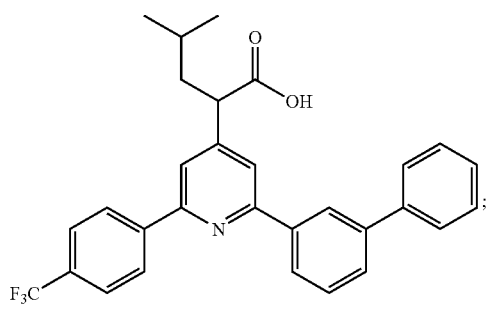
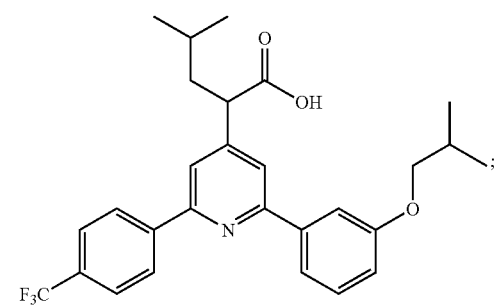
16
-continued
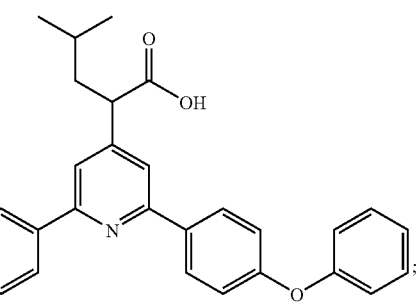
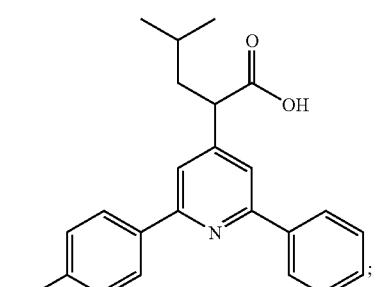
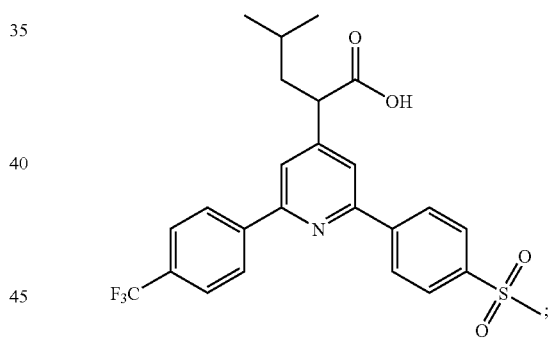
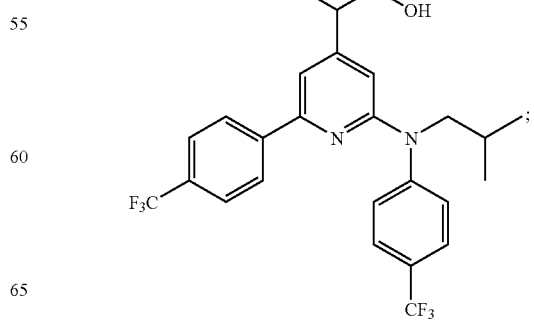

-continued

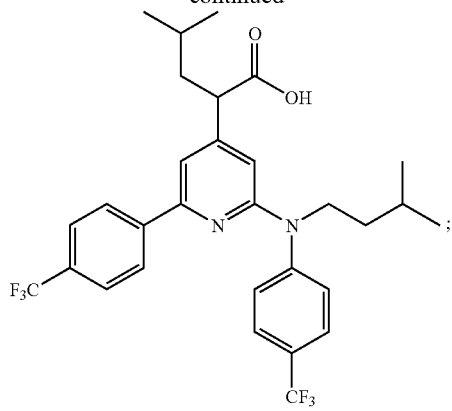

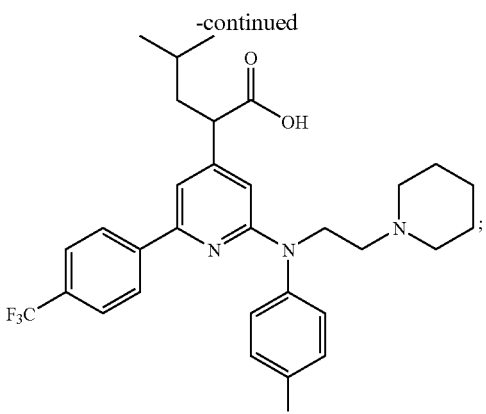

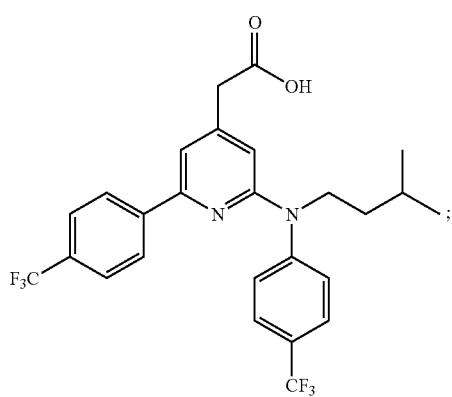

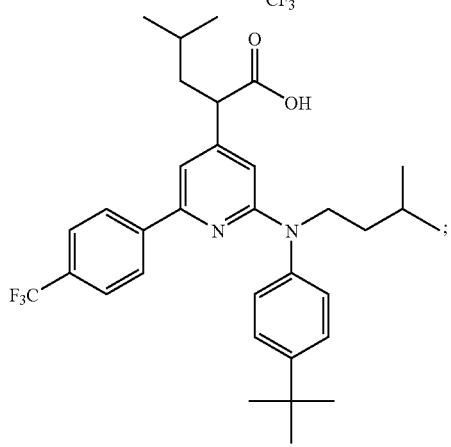

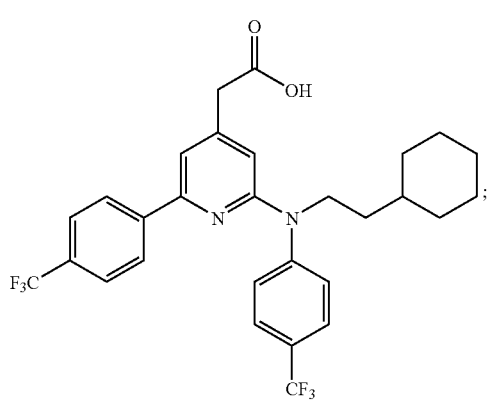

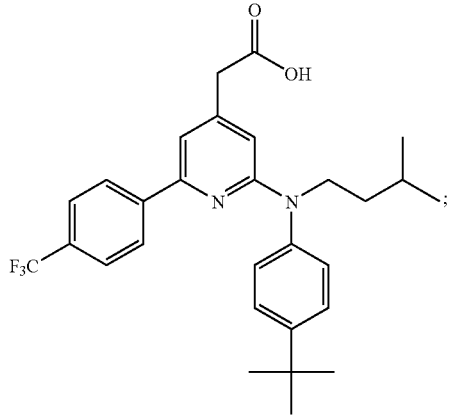

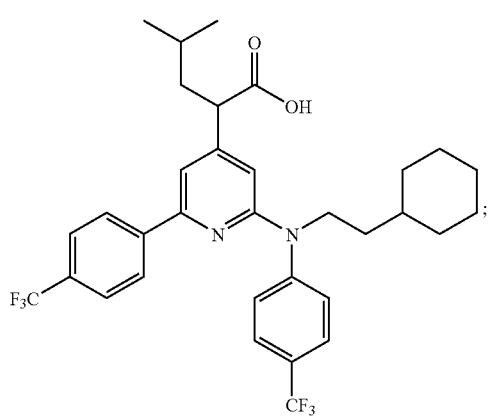

and solvates, hydrates, esters, and pharmaceutically acceptable salts thereof.

In another embodiment, the invention relates to a compound as described in the above examples or Formula I for use as a medicament.

In another embodiment, the invention relates to the use of a compound according to the above examples or Formula I for the preparation of a medicament for the modulation of γ-secretase.

In another embodiment, the invention relates to the use of a compound according to the above examples or Formula I for the preparation of a medicament for the treatment of a disease associated with an elevated level of Aβ42-production.

In another embodiment, the invention relates to the use of a compound according to the above examples or Formula I for the preparation of a medicament for the treatment of Alzheimer's disease.

In another embodiment, the invention relates to a method of treating a mammal for the modulation of γ-secretase, wherein said method comprises administering to the mammal a therapeutically effective amount of a compound of Formula I.

In another embodiment, the invention relates to a method of treating in a mammal a disease associated with an elevated level of Aβ42-production, wherein said method comprises administering to the mammal a therapeutically effective amount of a compound of Formula I.

One skilled in the art will recognize that the compounds of Formula I may have one or more asymmetric carbon atoms in their structure. It is intended that the present invention include within its scope single enantiomer forms of the compounds, racemic mixtures, and mixtures of enantiomers in which an enantiomeric excess is present.

Some of the compounds of the inventions and/or salts or esters thereof will exist in different stereoisomeric forms. All of these forms are subjects of the invention.

Described below are exemplary salts of the compounds according to the invention which are included herein. The list of the different salts stated below is not meant to be complete and limiting.

Compounds according to the invention which contain one or more acidic groups can be used according to the invention, e.g. as their alkali metal salts, alkaline earth metal salts or ammonium salts. More precise examples of such salts include sodium salts, potassium salts, calcium salts, magnesium salts or salts with ammonia or organic amines such as, e.g. ethylamine, ethanolamine, triethanolamine or amino acids.

The term "pharmaceutically acceptable" means approved by a regulatory agency such as the EMEA (Europe) and/or the FDA (US) and/or any other national regulatory agency for use in animals, preferably in humans.

The respective salts of the compounds according to the invention can be obtained by customary methods which are known to the person skilled in the art, for example by contacting these with an organic or inorganic base in a solvent or dispersant, or by cation exchange with other salts.

Furthermore, the invention includes all salts of the compounds according to the invention which, owing to low physiological compatibility, are not directly suitable for use in pharmaceuticals but which can be used, for example, as intermediates for chemical reactions or for the preparation of pharmaceutically acceptable salts or which might be suitable for studying γ-secretase modulating activity of a compound according of the invention in any suitable manner, such as any suitable in vitro assay.

The invention is considered to include prodrugs, i.e., derivatives of an acting drug that possess superior delivery capabilities and therapeutic value as compared to the acting drug. Prodrugs are transformed into active drugs by in vivo enzymatic or chemical processes.

The present invention furthermore includes all solvates of the compounds according to the invention.

The present invention furthermore includes derivatives/prodrugs (including the salts thereof) of the compounds according to the invention which contain physiologically tolerable and cleavable groups and which are metabolized in animals, preferably mammals, most preferably humans into a compound according to the invention.

The present invention furthermore includes the metabolites of the compounds according to the invention.

The term "metabolites" refers to all molecules derived from any of the compounds according to the invention in a cell or organism, preferably mammal.

Preferably the term "metabolites" relates to molecules which differ from any molecule which is present in any such cell or organism under physiological conditions.

The structure of the metabolites of the compounds according to the invention will be obvious to any person skilled in the art, using the various appropriate methods.

The invention also relates to compounds of the invention for use as medicaments. The compounds are as defined above, furthermore with respect to the medicaments the embodiments as described below with respect to the use of the invention, e.g. formulation, application and combination, also apply to this aspect of the invention.

In particular the compounds according to the invention are suitable for the treatment of Alzheimer's disease.

Details relating to said use are further disclosed below.

The compounds can be used for modulation of γ-secretase activity.

As used herein, the term "modulation of γ-secretase activity" refers to an effect on the processing of APP by the γ-secretase-complex. Preferably it refers to an effect in which the overall rate of processing of APP remains essentially as without the application of said compounds, but in which the relative quantities of the processed products are changed, more preferably in such a way that the amount of the Aβ42-peptide produced is reduced. For example a different Abeta species can be produced (e.g. Abeta-38 or other Abeta peptide species of shorter amino acid sequence instead of Abeta-42) or the relative quantities of the products are different (e.g. the ratio of Abeta-40 to Abeta-42 is changed, preferably increased).

Gamma secretase activity can e.g. be measured by determining APP processing, e.g. by determining the levels of Abeta peptide species produced, most importantly levels of Abeta-42 (see Example section, infra).

It has been previously shown that the γ-secretase complex is also involved in the processing of the Notch-protein. Notch is a signaling protein which plays a crucial role in developmental processes (e.g. reviewed in Schweisguth F (2004) Curr. Biol. 14, R129).

With respect to the use of said compounds for the modulation of γ-secretase activity in therapy, it seems particularly advantageous not to interfere with the Notch-processing activity of the γ-secretase activity in order to avoid putative undesired side-effects.

Thus, compounds are preferred which do not show an effect on the Notch-processing activity of the γ-secretase-complex.

Within the meaning of the invention, "effect on the Notch processing activity" includes both an inhibition or an activation of the Notch-processing activity by a certain factor.

A compound is defined as not having an effect on the Notch processing activity, if said factor is smaller than 20, preferably smaller than 10, more preferably smaller than 5, most preferably smaller than 2 in the respective assay as described in Shimizu et al (2000) Mol. Cell. Biol, 20: 6913 at a concentration of 30 μM.

Such a γ-secretase modulation can be carried out, e.g. in animals such as mammals. Exemplary mammals are mice, rats, guinea pigs, monkeys, dogs, cats. The modulation can also be carried out in humans. In a particular embodiment of the invention, said modulation is performed in vitro or in cell culture. As known to the person skilled in the art, several in vitro and cell culture assays are available.

Exemplary assays useful for measuring the production of C-terminal APP fragments in cell lines or transgenic animals by Western blot analysis include but are not limited to those described in Yan et al., 1999, Nature 402, 533-537.

An example of an in vitro γ-secretase assay is described in WO-03/008635. In this assay a suitable peptide substrate is contacted with a γ-secretase preparation and the ability to cleave the substrate is measured.

Concentrations of the various products of the γ-secretase cleavage (the Aβ-peptides) can be determined by various methods known to a person skilled in the art. Examples for such methods include determination of the peptides by mass-spectrometry or detection by antibodies.

Exemplary assays useful for the characterization of the profile of soluble Aβ peptides in cultured cell media and biological fluids include but are not limited to those described by Wang et al., 1996, J. Biol. Chem. 271, 31894-31902. In this assay a combination of immunoprecipitation of Abeta-peptides with specific antibodies and detection and quantification of the peptide species with matrix-assisted laser desorption ionization time-of-flight mass spectrometry is used.

Exemplary assays useful for measuring the production of Abeta-40 and Abeta-42 peptides by ELISA include but are not limited to those described in Vassar et al, 1999, Science 286, 735-741. Further information is disclosed for example in N. Ida et al. (1996) J. Biol. Chem. 271, 22908, and M. Jensen et al. (2000) Mol. Med. 6, 291. Suitable antibodies are available for example from The Genetics Company, Inc., Switzerland. Antibody-based kits are also available from Innogenetics, Belgium.

Cells which can be employed in such assays include cells which endogenously express the γ-secretase complex and transfected cells which transiently or stably express some or all interactors of the γ-secretase complex. Numerous available cell lines suitable for such assays are known to the skilled person. Cells and cell lines of neuronal or glial origin are particularly suitable. Furthermore, cells and tissues of the brain as well as homogenates and membrane preparations thereof may be used (Xia et al., 1998, Biochemistry 37, 16465-16471).

Such assays might be carried out for example to study the effect of the compounds according to the invention in different experimental conditions and configurations.

Furthermore, such assays might be carried out as part of functional studies on the γ-secretase complex.

For example, either one or more interactors (either in their wild-type form or carrying certain mutations and/or modifications) of the γ-secretase complex of an animal, preferably a mammal, more preferably humans, might be expressed in certain cell lines and the effect of the compounds according to the invention might be studied.

Mutated forms of the interactor(s) used can either be mutated forms which have been described in certain animals, preferably mammals, more preferably humans or mutated forms which have not previously been described in said animals.

Modifications of the interactors of the γ-secretase complex include both any physiological modification of said interactors and other modifications which have been described as modifications of proteins in a biological system.

Examples of such modifications include, but are not limited to, glycosylation, phosphorylation, prenylation, myristylation and farnesylation.

Furthermore, the compounds according to the invention can be used for the preparation of a medicament for the modulation of γ-secretase activity.

The activity of the γ-secretase can be modulated in different ways, i.e. resulting in different profiles of the various Aβ-peptides.

Respective dosages, routes of administration, formulations etc are disclosed further below.

The invention further relates to the use of the compounds of Formula I for the treatment of a disease associated with an elevated level of Aβ42-production. The disease with elevated levels of Abeta peptide production and deposition in the brain is typically Alzheimer's disease (AD), cerebral amyloid angiopathy, multi-infarct dementia, dementia pugilistica or Down syndrome, preferably AD.

As used herein, the term "treatment" is intended to refer to all processes, wherein there may be a slowing, interrupting, arresting, or stopping of the progression of a disease, but does not necessarily indicate a total elimination of all symptoms.

As used herein, the term "elevated level of Aβ42-production" refers to a condition in which the rate of production of Aβ42-peptide is increased due to an overall increase in the processing of APP or, preferably, it refers to a condition in which the production of the Aβ42 peptide is increased due to a modification of the APP-processing profile in comparison to the wild-type APP and non-pathological situation.

As outlined above, such an elevated Aβ42-level is a hallmark of patients developing or suffering from Alzheimer's disease.

One advantage of the compounds or a part of the compounds of the present invention may lie in their enhanced CNS-penetration.

Furthermore the invention relates to a pharmaceutical composition comprising a compound of Formula I in a mixture with an inert carrier.

Modulators of γ-secretase derived from compounds of Formula I can be formulated into pharmaceutical compositions comprising a compound of Formula I in a mixture with an inert carrier, where said inert carrier is a pharmaceutical carrier.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, including but not limited to peanut oil, soybean oil, mineral oil, sesame oil and the like. Water is a preferred carrier when the pharmaceutical composition is administered orally. Saline and aqueous dextrose are preferred carriers when the pharmaceutical composition is administered intravenously. Saline solutions and aqueous dextrose and glycerol solutions are preferably employed as liquid carriers for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsions, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

The compounds according to the invention and their pharmaceutically acceptable salts, optionally in combination with other pharmaceutically active compounds are suitable to treat or prevent Alzheimer's disease or the symptoms thereof. Such additional compounds include cognition-enhancing drugs such as acetylcholinesterase inhibitors (e.g. Donepezil, Tacrine, Galantamine, Rivastigmin), NMDA antagonists (e.g. Memantine) PDE4 inhibitors (e.g. Ariflo) or any other drug known to a person skilled in the art suitable to treat or prevent Alzheimer's disease. Such compounds also include cholesterol-lowering drugs such as statins (e.g. simvastatin). These compounds can be administered to animals, preferably to mammals, and in particular humans, as pharmaceuticals by themselves, in mixtures with one anther or in the form of pharmaceutical preparations.

Preservatives and other additives can also be present, such as, for example, antimicrobials, antioxidants, chelating agents, inert gases and the like. All carriers can be mixed as needed with disintegrants, diluents, granulating agents, lubricants, binders and the like using conventional techniques known in the art.

This invention further provides a method of treating a subject having a condition ameliorated by modulation of γ-secretase activity, which comprises administering to the subject a therapeutically effective dose of the instant pharmaceutical composition.

As used herein, the term "subject" includes, without limitation, any animal or artificially modified animal having a disorder ameliorated by modulation of γ-secretase activity. In a preferred embodiment, the subject is a human.

As used herein, a "therapeutically effective dose" of a pharmaceutical composition is an amount sufficient to stop, reverse or reduce the progression of a disorder. A "prophylactically effective dose" of a pharmaceutical composition is an amount sufficient to prevent a disorder, i.e., eliminate, ameliorate and/or delay the disorder's onset. Methods are known in the art for determining therapeutically and prophylactically effective doses for the instant pharmaceutical composition. The effective dose for administering the pharmaceutical composition to a human, for example, can be determined mathematically from the results of animal studies.

Various delivery systems are known and can be used to administer a compound of the invention for the treatment of Alzheimer's disease or for the modulation of the γ-secretase activity, e.g. encapsulation in liposomes, microparticles, and microcapsules: If not delivered directly to the central nervous system, preferably the brain, it is advantageous to select and/or modify methods of administration in such a way as to allow the pharmaceutical compound to cross the blood-brain barrier.

Methods of introduction include, but are not limited to, intradermal, intramuscular, intraperitoneal, intravenous, subcutaneous, intranasal, epidural, and oral routes.

The compounds may be administered by any convenient route, for example by infusion, by bolus injection, by absorption through epithelial or mucocutaneous linings and may be administered together with other biologically active agents. Administration can be systemic or local. In addition, it may be desirable to introduce the pharmaceutical compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g. by use of an inhaler or nebulizer, and formulation with an aerosolizing agent.

Modulators of γ-secretase derived from compounds of Formula I can be delivered in a vesicle, in particular a liposome (Langer (1990) Science 249, 1527).

Modulators of γ-secretase derived from compounds of Formula I can be delivered via a controlled release system. In one embodiment, a pump may be used (Sefton (1987) CRC Crit. Ref Biomed. Eng. 14, 201; Buchwald et al. (1980) Surgery 88, 507; Saudek et al. (1989) N. Engl. J. Med. 321, 574). In another embodiment, polymeric materials can be used (Ranger and Peppas (1983) Macromol. Sci. Rev. Macromol. Chem. 23, 61; Levy et al. (1985) Science 228, 190; During et al. (1989) Ann. Neurol. 25, 351; Howard et al. (1989) J. Neurosurg. 71, 858). In yet another embodiment, a controlled release system can be placed in proximity of the therapeutic target, i.e., the brain, thus requiring only a fraction of the systemic dose (e.g. Goodson, 1984, In: Medical Applications of Controlled Release, supra, Vol. 2, 115). Other controlled release systems are discussed in the review by Langer (1990, Science 249, 1527).

In order to select an appropriate way of administration, the person skilled in the art will also consider routes of administration which have been selected for other known Anti-Alzheimer-drugs.

For example, Aricept/Donepezil and Cognex/Tacrine (all acetylcholinesterase-inhibitors) are being taken orally, Axura/Memantine (an NMDA-receptor antagonist) has been launched both as tablets/liquid and as an i.v.-solution.

Furthermore, the skilled person in the art will take into account the available data with respect to routes of administration of members of the NSAID-family in clinical trials and other studies investigating their effect on Alzheimer's disease.

In order to select the appropriate dosage, the person skilled in the art will choose a dosage which has been shown to be not toxic in preclinical and/or clinical studies and which can be in accordance with the values given beforehand, or which may deviate from these.

The precise dose to be employed in the formulation will also depend on the route of administration, and the seriousness of the disease or disorder, and should be decided according to the judgment of the practitioner and each patient's circumstances. However, suitable dosage ranges for intravenous administration are generally about 20-500 micrograms of active compound per kilogram body weight. Suitable dosage ranges for intranasal administration are generally about 0.01 mg/kg body weight to 1 mg/kg body weight. Effective doses may be extrapolated from dose-response curves derived from in vitro or animal model test systems.

An exemplary animal model is the transgenic mouse strain "Tg2576" containing an APP695-form with the double mutation KM670/671NL. For reference see e.g. U.S. Pat. No. 5,877,399 and Hsiao et al. (1996) Science 274, 99 and also Kawarabayahsi T (2001) J. Neurosci. 21, 372; Frautschy et al. (1998) Am. J. Pathol. 152, 307; Irizarry et al. (1997) J. Neuropathol. Exp. Neurol. 56, 965; Lehman et al. (2003) Neurobiol. Aging 24, 645.

Substantial data from several studies are available to the skilled person in the art, which are instructive to the skilled person to select the appropriate dosage for the chosen therapeutic regimen.

Numerous studies have been published in which the effects of molecules on the γ-secretase activity are described. Exemplary studies are Lim et al. (2001) Neurobiol. Aging 22, 983; Lim et al. (2000) J Neurosci. 20, 5709; Weggen et al. (2001) Nature 414, 212; Eriksen et al. (2003) J Clin Invest. 112, 440; Yan et al. (2003) J Neurosci. 23, 7504.

DEFINITIONS

The term "alkenyl," whether used alone or as part of a substituent group, for example, "$C_{1-4}$alkenyl(aryl)," refers to a partially unsaturated branched or straight chain monovalent hydrocarbon radical having at least one carbon-carbon double bond, whereby the double bond is derived by the removal of one hydrogen atom from each of two adjacent carbon atoms of a parent alkyl molecule and the radical is derived by the removal of one hydrogen atom from a single carbon atom. Atoms may be oriented about the double bond in either the cis (Z) or trans (E) conformation. Typical alkenyl radicals include, but are not limited to, ethenyl, propenyl, allyl (2-propenyl), butenyl and the like. Examples include $C_{2-8}$alkenyl or $C_{2-4}$alkenyl groups.

The term "$C_{a-b}$" (where a and b are integers referring to a designated number of carbon atoms) refers to an alkyl, alkenyl, alkynyl, alkoxy or cycloalkyl radical or to the alkyl portion of a radical in which alkyl appears as the prefix root containing from a to b carbon atoms inclusive. For example, $C_{1-4}$ denotes a radical containing 1, 2, 3 or 4 carbon atoms.

The term "alkyl" refers to both linear and branched chain radicals of up to 12 carbon atoms, preferably up to 6 carbon atoms, unless otherwise indicated, and includes, but is not limited to, methyl, ethyl, propyl, isopropyl, n-butyl, isobutyl, sec-butyl, tert-butyl, pentyl, isopentyl, hexyl, isohexyl, heptyl, octyl, 2,2,4-trimethylpentyl, nonyl, decyl, undecyl and dodecyl.

The term "heterocyclyl" refers to a saturated or partially unsaturated monocyclic ring radical derived by the removal of one hydrogen atom from a single carbon or nitrogen ring atom. Typical heterocyclyl radicals include 2H-pyrrolyl, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, piperidinyl, 1,4-dioxanyl, morpholinyl, 1,4-dithianyl, thiomorpholinyl, piperazinyl, azepanyl, hexahydro-1,4-diazepinyl and the like.

The term "substituted," refers to a core molecule on which one or more hydrogen atoms have been replaced with one or more functional radical moieties. Substitution is not limited to a core molecule, but may also occur on a substituent radical, whereby the substituent radical becomes a linking group.

General Synthesis Description

Compounds of Formula I can be prepared by methods known to those who are skilled in the art. The following reaction schemes are only meant to represent examples of the invention and are in no way meant to be a limit of the invention.

Schemes 1a-1c illustrates the synthetic route leading to compounds of Formula I, where X is a bond.

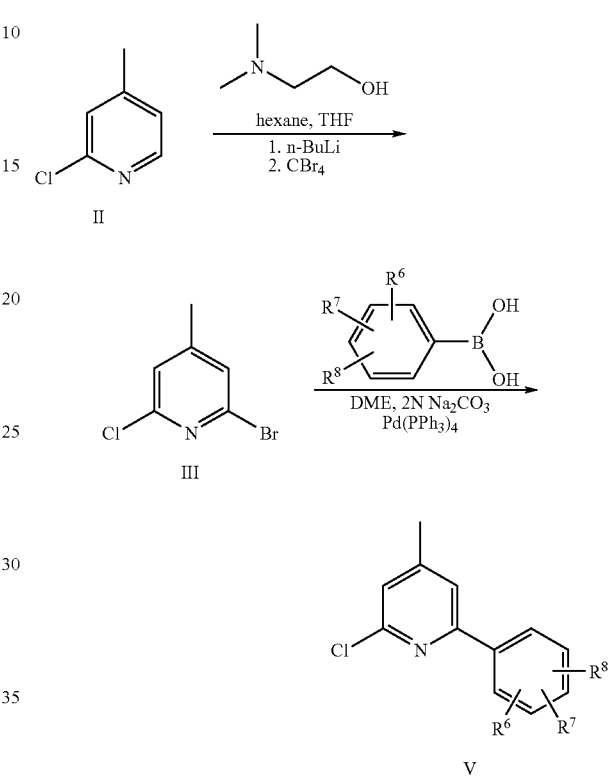

Starting with 2-chloro-4-methylpyridine II, treatment with n-butyllithium in the presence of N,N-dimethylaminoethanol in hexane, followed by addition of carbon tetrabromide in THF affords 2-bromo-6-chloro-4-methylpyridine III. Compound III undergoes a palladium coupling with boronic acid IV in the presence of a base, such as $Na_2CO_3$, in a suitable solvent, such as DME, to give chloropyridine V.

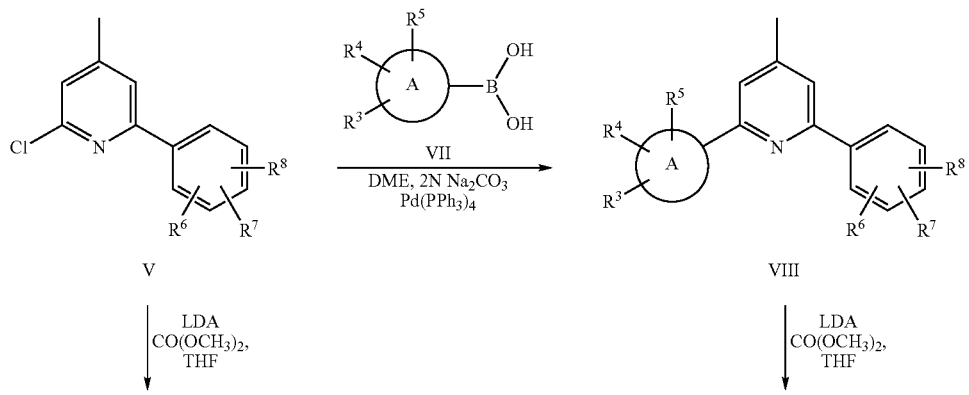

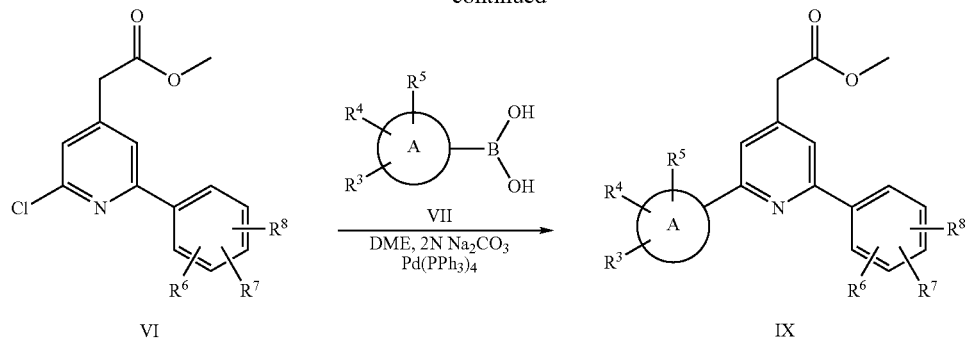

Continuing to Scheme 1b, Chloropyridine V is then coupled with boronic acid VII in the presence of a palladium catalyst, such as Pd(PPh$_3$)$_4$, and a base, such as Na$_2$CO$_3$, in a solvent, such as DME to generate compound VIII. Further treatment of VIII with LDA and dimethyl carbonate in a solvent, such as THF, to produce compound IX. Alternatively, chloropyridine V can be treated with LDA and dimethyl carbonate in a solvent, such as THF, to generate VI. Coupling of VI with boronic acid VII in the presence of a palladium catalyst, such as Pd(PPh$_3$)$_4$, a base, such as Na$_2$CO$_3$ in a solvent, such as DME gives compound IX.

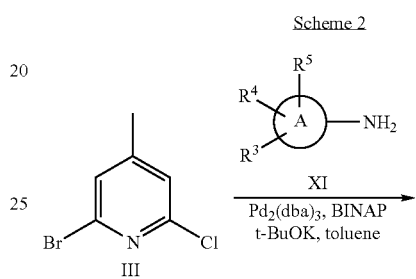

According to Scheme 1c, compound IX can then be reacted with R$^1$Hal (where Hal is halogen, such as Br, or Cl) in the presence of a base, such as potassium bis(trimethylsilyl)amide, in a suitable solvent, such as THF, to give the ester X. Catalytic reduction of the R$^1$ alkene (if desired), followed by hydrolysis of the ester X provides compounds of Formula I where R$^9$ is H. Re-esterification under standard conditions provides compounds of Formula I where R$^9$ is other than H.

Scheme 2 illustrates the synthetic route leading to compounds of the Formula I where X is NR$^2$.

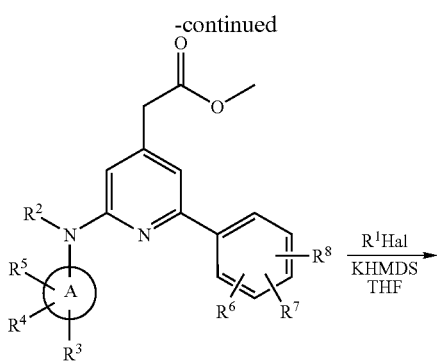

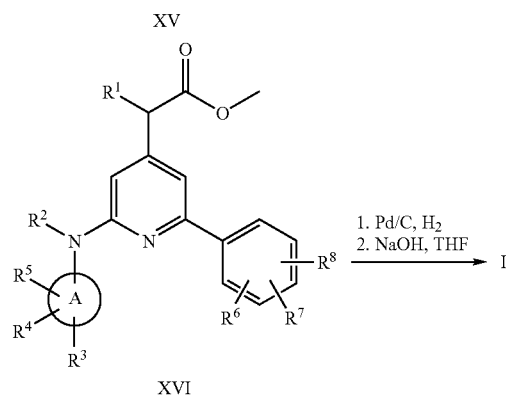

2-Bromo-6-chloro-4-methylpyridine III can be coupled with amine XI in the presence of a suitable catalyst, such as Pd$_2$(dba)$_3$, a ligand, such as BINAP or XANTPHOS and a base, such as potassium tert-butoxide, in a solvent, such as toluene to give compound XII. Alkylation of XII with R$^2$X in the presence of a base, such as NaH, and a solvent, such as THF, affords XIII. Coupling of XIII with boronic acid IV in the presence of a palladium catalyst, such as Pd(PPh$_3$)$_4$, and a base, such as 2N Na$_2$CO$_3$, in a solvent, such as DME generates compound XIV. Treatment of XIV with LDA and dimethyl carbonate in a solvent, such as THF yields compound XV. Alkylation of compound XV with R$^1$Hal (where Hal is a halogen, such as Br, or Cl) in the presence of a base, such as potassium bis(trimethylsilyl)amide, in a suitable solvent, such as THF affords ester XVI. Catalytic reduction followed by hydrolysis of the ester XVI provides compounds of Formula I.

Synthetic Procedures

All reactions were carried out under inert atmosphere unless otherwise stated. NMR spectra were obtained on a Bruker dpx400. LCMS was carried out on an Agilent 1100 using a ZORBAX® SB-C18, 4.6×75 mm, 3.5 micron column for method A. Column flow was 1 ml/min and solvents used were water and acetonitrile (0.1% TFA) with an injection volume of 10 ul. Wavelengths were 254 and 210 nm. Methods are described below:

| Method | Flow Rate | Solvent |
|---|---|---|
| A | 1 ml/min | 0-1.5-95% MeCN |
| | | 1.5-6 min 95% |
| | | 4.5-5 min 95%-5% MeCN |

Abbreviations

Ac acetyl
BINAP 2,2'-bis(diphenylphosphino)-1,1'-binaphthyl
DCM dichloromethane
DME 1,2-dimethoxyethane
DMF N,N-dimethylformamide
DMSO dimethyl sulfoxide
Et ethyl
EtOAc ethyl acetate\
KHMDS potassium bis(trimethylsilyl)amide
LCMS liquid chromatography-mass spectrometry
LDA lithium diisopropylamide
Me methyl
Pd$^2$(dba)$_3$ tris(dibenzylideneacetone)dipalladium
Ph phenyl
t-BuOK potassium tert-butoxide
TFA trifluoroacetic acid
THF tetrahydrofuran
XANTPHOS 4,5-Bis(diphenylphosphino)-9,9-dimethylxanthene

EXPERIMENTAL

Example 1

2-[2,6-Bis-(4-trifluoromethyl-phenyl)-pyridin-4-yl]-4-methyl-pentanoic acid

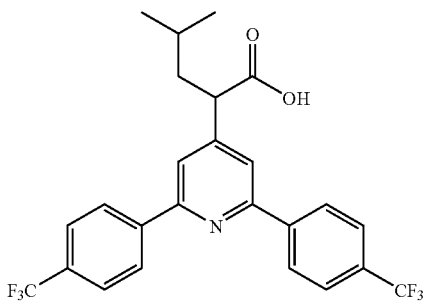

a) 2-Bromo-6-chloro-4-methyl-pyridine

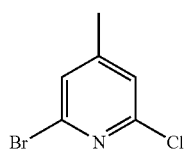

This compound was prepared according to procedure described by Thomas Kaminski, et al., *Eur. J. Org. Chem.*, 2003, 3855-3860. ¹H NMR (300 MHz, CDCl₃) δ 7.26 (s, 1H), 7.13 (s, OH), 2.34 (s, 3H).

b) 4-Methyl-2,6-bis-(4-trifluoromethylphenyl)-pyridine

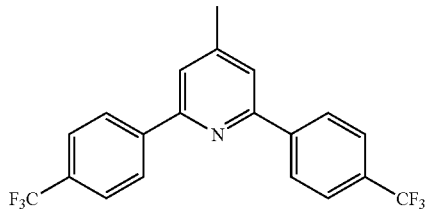

To a degassed solution of 2-bromo-6-chloro-4-methyl-pyridine (1.45 g, 7.04 mmol), 4-trifluoromethylbenzeneboronic acid (3.8 g, 20 mmol), 2N Na₂CO₃ (10 mL) in DME (80 mL) was added tetrakis(triphenylphosphine)palladium (690 mg, 0.6 mmol) under argon. The mixture was heated to 85° C. for 4 h, cooled to room temperature, diluted with water, and extracted with methylene chloride (3×). The organic solution was washed with brine, dried over Na₂SO₄, and concentrated. The residue was purified by column chromatography on silica gel (0-20% methylene chloride in heptane) to give the product as an off white solid (1.75 g, 65%). ¹H NMR (300 MHz, CDCl₃) δ 8.24 (d, J=7.91 Hz, 26H), 7.75 (d, J=8.29 Hz, 26H), 7.61 (s, 13H), 2.53 (s, 19H). MS m/e 382.2 (M+H)

c) [2,6-Bis-(4-trifluoromethyl-phenyl)-pyridin-4-yl]-acetic acid methyl ester

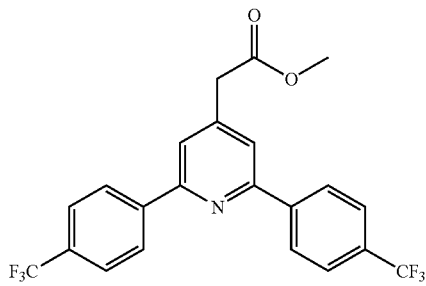

A solution of LDA (1.8 M in THF/heptane/ethyl benzene, 4.4 mL, 7.92 mmol) was added slowly to a stirred solution of 4-methyl-2,6-bis-(4-trifluoromethylphenyl)-pyridine (1.37 g, 3.6 mmol) under N₂ at −78° C. After 30 minutes, dimethyl carbonate (720 μL, 8.0 mmol) was added. After stirring at −78° C. for an additional 30 minutes, the solution was allowed to warm up slowly and stirred at 0° C. for 30 minutes The reaction was quenched with saturated aqueous NH₄Cl (10 mL). The mixture was partitioned between CH₂Cl₂ and H₂O. The aqueous layer was extracted with CH₂Cl₂ (2×). The combined extracts were washed with brine, then dried (Na₂SO₄), filtered and evaporated. The residue was purified by column chromatography on silica gel (10-50% CH₂Cl₂ in heptane) to give the product as a white solid (1.38 g, 87%). ¹H NMR (300 MHz, CDCl₃) δ 8.24 (d, J=7.91 Hz, 4H), 7.76 (d, J=7.91 Hz, 4H), 7.72 (s, 2H), 3.80 (s, 2H), 3.77 (s, 3H). MS m/e 440.2 (M+H)

d) 2-[2,6-Bis-(4-trifluoromethyl-phenyl)-pyridin-4-yl]-4-methyl-pent-4-enoic acid methyl ester

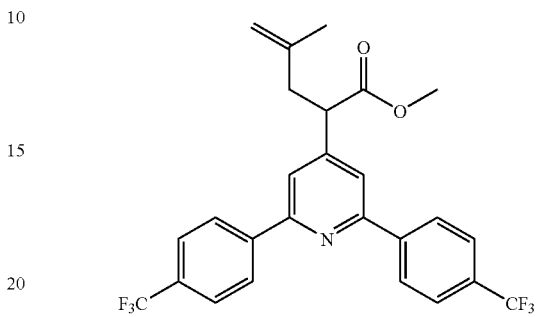

To a solution of [2,6-bis-(4-trifluoromethylphenyl)-pyridin-4-yl]-acetic acid methyl ester (1.18 g, 2.69 mmol) in THF (30 mL) at −78° C. under argon was added potassium bis(trimethylsilyl)amide (0.5 M solution in toluene, 5.38 mL, 2.69 mmol). After stirring for 30 minutes, 3-bromo-2-methylpropene (273 μL, 2.69 mmol) was added and stirred for an additional 30 minutes. The reaction mixture was allowed to warm up slowly and stirred for another 30 minutes at 0° C. The mixture was then concentrated and purified by column chromatography on silica gel (0-8% ethyl acetate in heptane) to give the product as a white solid (940 mg, 71%). ¹H NMR (300 MHz, CDCl₃) δ 8.24 (d, J=8.29 Hz, 4H), 7.76 (d, J=8.29 Hz, 4H), 7.74 (s, 2H), 4.79 (d, J=19.59 Hz, 2H), 3.97 (dd, J=6.78, 9.04 Hz, 1H), 3.72 (s, 3H), 2.95 (dd, J=8.85, 14.51 Hz, 1H), 2.56 (dd, J=6.59, 14.51 Hz, 1H), 1.78 (s, 3H). MS m/e 494.2 (M+H)

e) 2-[2,6-Bis-(4-trifluoromethyl-phenyl)-pyridin-4-yl]-4-methyl-pentanoic acid methyl ester

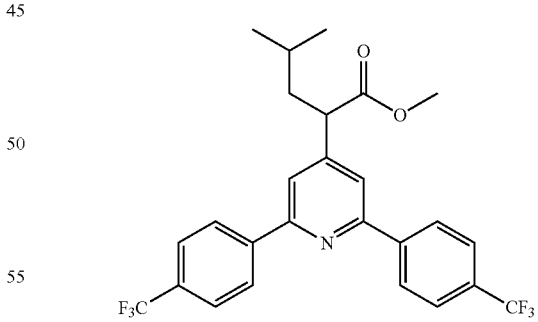

A solution of 2-[2,6-bis-(4-trifluoromethyl-phenyl)-pyridin-4-yl]-4-methyl-pent-4-enoic acid methyl ester (280 mg, 0.57 mmol), Pd/C (10%, 30 mg) in methanol (10 mL) was hydrogenated for 4 h. The mixture was filtered through Celite, washed with methanol, and evaporated. The residue was dissolved in CH₂Cl₂, filtered and evaporated to give the product as a white solid (260 mg, 92%). ¹H NMR (300 MHz, CDCl₃) δ 8.24 (d, J=8.29 Hz, 4H), 7.76 (d, J=8.29 Hz, 4H), 7.73 (s, 2H), 3.82 (t, J=7.72 Hz, 1H), 3.72 (s, 3H), 2.11 (dt, J=7.72, 13.94 Hz, 1H), 1.76 (dt, J=6.92, 13.66 Hz, 1H), 1.49-1.62 (m, 1H), 0.97 (d, J=6.40 Hz, 6H). MS m/e 496.2 (M+H).

f) 2-[2,6-Bis-(4-trifluoromethyl-phenyl)-pyridin-4-yl]-4-methyl-pentanoic acid

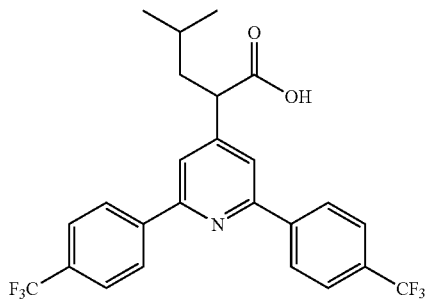

A solution of 2-[2,6-bis-(4-trifluoromethyl-phenyl)-pyridin-4-yl]-4-methyl-pentanoic acid methyl ester (250 mg, 0.5 mmol) in NaOH (1N, 1 mL) and THF (5 mL) was stirred at 40° C. overnight. The mixture was cooled to room temperature, acidified with 10% citric acid, and extracted with $CH_2Cl_2$ (3×). The organic layer was washed with brine, dried over $Na_2SO_4$, filtered and evaporated. The residue was purified by chromatography (5-25% ethyl acetate in $CH_2Cl_2$) to give the product as a white solid (190 mg, 78%). $^1H$ NMR (300 MHz, $CDCl_3$) δ 8.23 (d, J=8.29 Hz, 4H), 7.68-7.83 (m, 6H), 3.85 (t, J=7.72 Hz, 1H), 2.05-2.17 (m, 1H), 1.79 (dt, J=7.06, 13.75 Hz, 1H), 1.53-1.64 (m, 1H), 0.98 (d, J=6.40 Hz, 6H). MS m/e 482.2 (M+H).

Example 2

2-[2-(4-Fluoro-phenyl)-6-(4-trifluoromethyl-phenyl)-pyridin-4-yl]-4-methyl-pentanoic acid

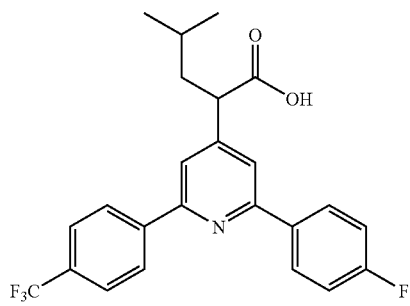

a) 2-Chloro-4-methyl-6-(4-trifluoromethyl-phenyl)-pyridine

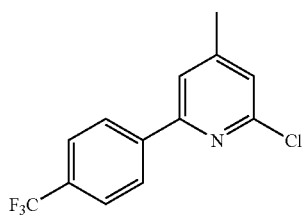

To a degassed solution of 2-bromo-6-chloro-4-methyl-pyridine (900 mg, 4.37 mmol), 4-trifluoromethylbenzeneboronic acid (830 mg, 4.37 mmol), 2N $Na_2CO_3$ (4 mL) in DME (40 mL) was added tetrakis(triphenylphosphine)palladium (320 mg, 0.3 mmol) under argon. The mixture was heated to 55° C. for 5 h, cooled to room temperature, diluted with water, and extracted with methylene chloride (3×). The organic solution was washed with brine, dried over $Na_2SO_4$, and concentrated. The residue was purified by column chromatography on silica gel (10-25% methylene chloride in heptane) to give the product as an off white solid (800 mg, 68%). $^1H$ NMR (300 MHz, $CDCl_3$) δ 8.09 (d, J=7.91 Hz, 2H), 7.71 (d, J=8.29 Hz, 2H), 7.49 (s, 1H), 7.16 (s, 1H), 2.43 (s, 3H). MS m/e 272.1 (M+H).

b) 2-(4-Fluoro-phenyl)-4-methyl-6-(4-trifluoromethyl-phenyl)-pyridine

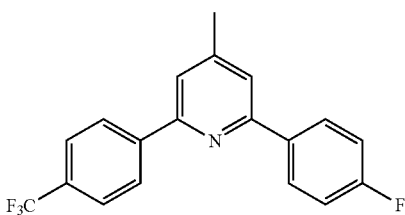

To a degassed solution of 2-chloro-4-methyl-6-(4-trifluoromethyl-phenyl)-pyridine (270 mg, 1.0 mmol), 4-fluorobenzeneboronic acid (155 mg, 1.0 mmol), 2N $Na_2CO_3$ (1.5 mL) in DME (10 mL) was added tetrakis(triphenylphosphine)palladium (70 mg, 0.06 mmol) under argon. The mixture was heated to 85° C. for 6 h, cooled to room temperature, diluted with water, and extracted with methylene chloride (3×). The organic solution was washed with brine, dried over $Na_2SO_4$, and concentrated. The residue was purified by column chromatography on silica gel (5-20% methylene chloride in heptane) to give the product as an off white solid (275 mg, 83%). $^1H$ NMR (300 MHz, $CDCl_3$) δ 8.23 (d, J=7.91 Hz, 2H), 8.12 (dd, J=5.27, 9.04 Hz, 2H), 7.74 (d, J=8.29 Hz, 2H), 7.54 (d, J=3.01 Hz, 2H), 7.18 (t, J=8.67 Hz, 2H), 2.50 (s, 3H). MS m/e 332.3 (M+H)

c) [2-(4-Fluoro-phenyl)-6-(4-trifluoromethyl-phenyl)-pyridin-4-yl]-acetic acid methyl ester

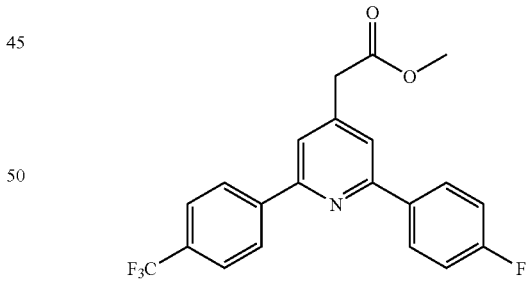

A solution of LDA (1.8 M in THF/heptane/ethyl benzene, 1.1 mL, 2.0 mmol) was added slowly to a stirred solution of 2-(4-fluoro-phenyl)-4-methyl-6-(4-trifluoromethyl-phenyl)-pyridine (260 g, 0.8 mmol) under $N_2$ at −78° C. After 30 minutes dimethyl carbonate (200 μL, 2.0 mmol) was added. After stirring at −78° C. for an additional 30 minutes, the solution was allowed to warm slowly and stirred at 0° C. for 30 minutes. The reaction was quenched with saturated aqueous $NH_4Cl$ (2 mL). The mixture was partitioned between $CH_2Cl_2$ and $H_2O$. The aqueous layer was extracted with $CH_2Cl_2$ (2×). The combined extracts were washed with brine, then dried ($Na_2SO_4$), filtered and evaporated. The residue was purified by column chromatography on silica gel (40-80% CH$_2$Cl$_2$ in heptane) to give the product as a white solid (130 mg, 42%). $^1$H NMR (300 MHz, CDCl$_3$) δ 8.23 (d, J=7.91 Hz, 2H), 8.13 (dd, J=5.46, 8.85 Hz, 2H), 7.75 (d, J=8.29 Hz, 2H), 7.64 (d, J=2.64 Hz, 2H), 7.19 (t, J=8.67 Hz, 2H), 3.78 (s, 2H), 3.76 (s, 3H). MS m/e 390.2 (M+H).

d) 2-[2-(4-Fluoro-phenyl)-6-(4-trifluoromethyl-phenyl)-pyridin-4-yl]-4-methyl-pent-4-enoic acid methyl ester

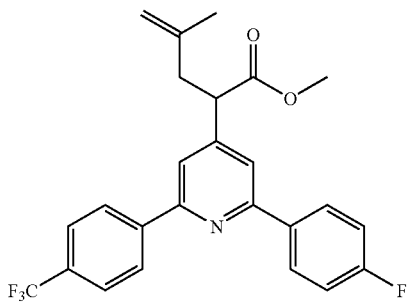

To a solution of [2-(4-fluoro-phenyl)-6-(4-trifluoromethyl-phenyl)-pyridin-4-yl]-acetic acid methyl ester (130 mg, 0.3 mmol) in THF (5 mL) at −78° C. under argon was added potassium bis(trimethylsilyl)amide (0.5 M solution in toluene, 600 μL, 0.3 mmol). After stirring for 30 minutes, 3-bromo-2-methylpropene (40 mg, 0.3 mmol) was added and stirred for 30 additional minutes. The reaction mixture was allowed to warm up slowly and stirred for another 30 minutes at 0° C. The mixture was then concentrated and purified by column chromatography on silica gel (0-8% ethyl acetate in heptane) to give the product as a colorless oil (80 mg, 60%). $^1$H NMR (300 MHz, CDCl$_3$) δ 8.23 (d, J=8.29 Hz, 2H), 8.08-8.18 (m, 2H), 7.75 (d, J=8.29 Hz, 2H), 7.67 (d, J=1.88 Hz, 2H), 7.19 (t, J=8.85 Hz, 2H), 4.78 (d, J=18.08 Hz, 2H), 3.95 (dd, J=6.78, 9.04 Hz, 1H), 3.72 (s, 3H), 2.94 (dd, J=9.04, 14.69 Hz, 1H), 2.55 (dd, J=6.40, 14.69 Hz, 1H), 1.77 (s, 3H). MS m/e 444.3 (M+H).

e) 2-[2-(4-Fluoro-phenyl)-6-(4-trifluoromethyl-phenyl)-pyridin-4-yl]-4-methyl-pentanoic acid methyl ester

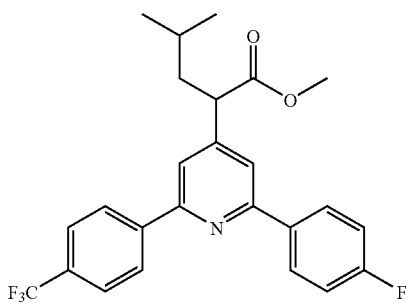

A solution of 2-[2-(4-fluoro-phenyl)-6-(4-trifluoromethyl-phenyl)-pyridin-4-yl]-4-methyl-pent-4-enoic acid methyl ester (80 mg, 0.18 mmol), Pd/C (10%, 10 mg) in methanol (10 mL) was hydrogenated for 4 h. The mixture was filtered through Celite, washed with methanol, and evaporated. The residue was dissolved in CH$_2$Cl$_2$, filtered and evaporated to give the product as a colorless oil (80 mg, 100%). $^1$H NMR (300 MHz, CDCl$_3$) δ 8.23 (d, J=8.29 Hz, 2H), 8.08-8.18 (m, 2H), 7.75 (d, J=8.29 Hz, 2H), 7.66 (d, J=1.88 Hz, 2H), 7.13-7.24 (m, 2H), 3.80 (t, J=7.72 Hz, 1H), 3.72 (s, 3H), 2.09 (dt, J=7.72, 13.56 Hz, 1H), 1.75 (dt, J=7.06, 13.75 Hz, 1H), 1.54 (dt, J=6.73, 13.28 Hz, 1H), 1.46-1.48 (m, 0H), 0.96 (d, J=6.40 Hz, 6H). MS m/e 446.3 (M+H).

f) 2-[2-(4-Fluoro-phenyl)-6-(4-trifluoromethyl-phenyl)-pyridin-4-yl]-4-methyl-pentanoic acid

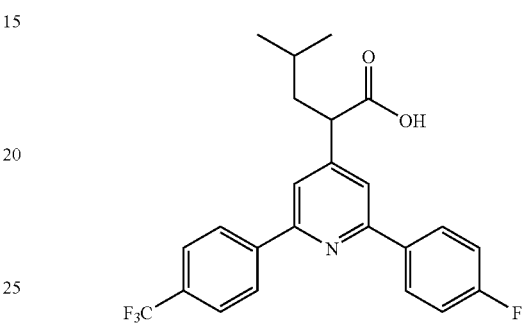

A solution of 2-[2-(4-fluoro-phenyl)-6-(4-trifluoromethyl-phenyl)-pyridin-4-yl]-4-methyl-pentanoic acid methyl ester (80 mg, 0.18 mmol) in NaOH (1N, 1 mL) and THF (4 mL) was stirred at 40° C. overnight. The mixture was cooled to room temperature, acidified with 10% citric acid, and extracted with CH$_2$Cl$_2$ (3×). The organic layer was washed with brine, dried over Na$_2$SO$_4$, filtered and evaporated. The residue was purified by chromatography (5-25% ethyl acetate in CH$_2$Cl$_2$) to give the product as a white foam (60 mg, 77%). $^1$H NMR (300 MHz, CDCl$_3$) δ 8.21 (d, J=8.29 Hz, 2H), 8.05-8.15 (m, 2H), 7.73 (d, J=8.29 Hz, 2H), 7.65 (d, J=1.51 Hz, 2H), 7.11-7.23 (m, 2H), 3.80 (t, J=7.72 Hz, 1H), 2.08-2.16 (m, 1H), 1.77 (dt, J=7.06, 13.75 Hz, 1H), 1.48-1.64 (m, 1H), 0.96 (d, J=6.40 Hz, 6H). MS m/e 432.3 (M+H).

Example 3

4-Methyl-2-[2-(4-trifluoromethoxy-phenyl)-6-(4-trifluoromethyl-phenyl)-pyridin-4-yl]-pentanoic acid

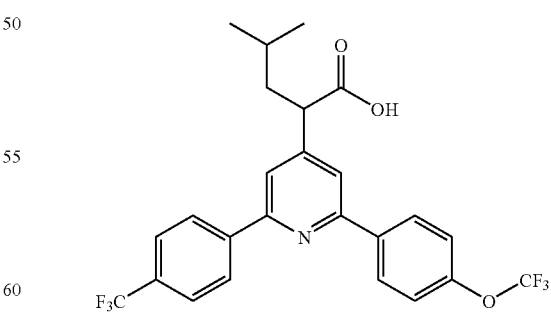

The title compound was prepared using 4-trifluoromethyl-benzeneboronic acid in place of 4-fluorobenzeneboronic acid as described in Example 2. $^1$H NMR (300 MHz, CDCl$_3$) δ 8.21 (d, J=8.29 Hz, 2H), 8.14 (d, J=9.04 Hz, 2H), 7.74 (d, J=8.29 Hz, 2H), 7.68 (d, J=2.64 Hz, 2H), 7.34 (d, J=8.29 Hz, 2H), 3.82 (t, J=7.72 Hz, 1H), 2.04-2.16 (m, 1H), 1.69-1.86 (m, 1H), 1.48-1.64 (m, 1H), 0.96 (d, J=6.40 Hz, 6H). MS m/e 498.3 (M+H).

Example 4

2-[2-(4-Methoxy-phenyl)-6-(4-trifluoromethyl-phenyl)-pyridin-4-yl]-4-methyl-pentanoic acid

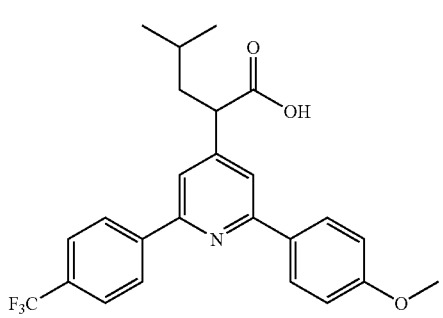

The title compound was prepared using 4-methoxybenzeneboronic acid in place of 4-fluorobenzeneboronic acid as described in Example 2. ¹H NMR (300 MHz, CDCl₃) δ 8.22 (d, J=8.29 Hz, 2H), 8.08 (d, J=9.04 Hz, 2H), 7.73 (d, J=8.29 Hz, 2H), 7.62 (d, J=6.78 Hz, 2H), 7.01 (d, J=8.67 Hz, 2H), 3.88 (s, 3H), 3.79 (t, J=7.72 Hz, 1H), 2.00-2.15 (m, 1H), 1.77 (dt, J=7.06, 13.75 Hz, 1H), 1.52-1.63 (m, 1H), 0.95 (d, J=6.40 Hz, 5H). MS m/e 444.2 (M+H).

Example 5

4-Methyl-2-[2-(4-trifluoromethyl-phenyl)-6-(3,4,5-trifluoro-phenyl)-pyridin-4-yl]-pentanoic acid

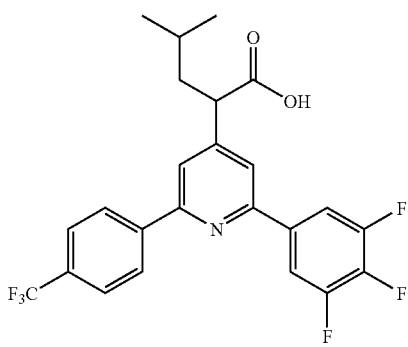

The title compound was prepared using 3,4,5-trifluorobenzeneboronic acid in place of 4-fluorobenzeneboronic acid as described in Example 2. ¹H NMR (300 MHz, CDCl₃) δ 8.20 (d, J=8.29 Hz, 2H), 7.68-7.83 (m, 5H), 7.62 (s, 1H), 3.83 (t, J=7.72 Hz, 1H), 2.07-2.17 (m, 1H), 1.77 (dt, J=7.06, 13.75 Hz, 1H), 1.57 (dt, J=6.73, 13.28 Hz, 1H), 0.97 (d, J=6.78 Hz, 6H). MS m/e 468.1 (M+H).

Example 6

2-[2-(3,5-Bis-trifluoromethyl-phenyl)-6-(4-trifluoromethyl-phenyl)-pyridin-4-yl]-4-methyl-pentanoic acid

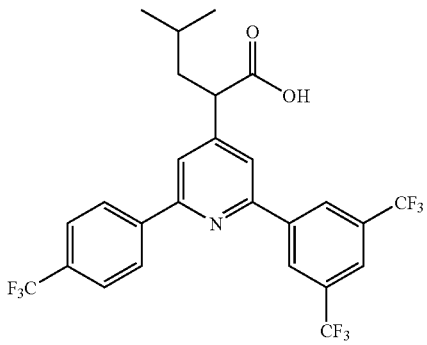

a) [2-Chloro-6-(4-trifluoromethyl-phenyl)-pyridin-4-yl]-acetic acid methyl ester

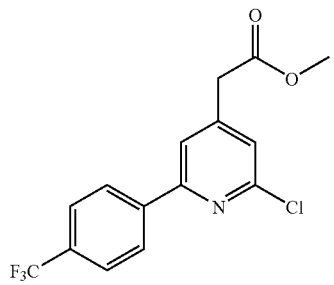

A solution of LDA (1.8 M in THF/heptane/ethyl benzene, 3.0 mL, 5.4 mmol) was added slowly to a stirred solution of 2-Chloro-4-methyl-6-(4-trifluoromethyl-phenyl)-pyridine (545 g, 2.0 mmol) under N₂ at −78° C. After 30 minutes dimethyl carbonate (400 μL, 4.0 mmol) was added. After stirring at −78° C. for an additional 30 minutes, the solution was allowed to warm up slowly and stirred at 0° C. for 30 minutes. The reaction was quenched with saturated aqueous NH₄Cl (4 mL). The mixture was partitioned between CH₂Cl₂ and H₂O. The aqueous layer was extracted with CH₂Cl₂ (2×). The combined extracts were washed with brine, then dried (Na₂SO₄), filtered and evaporated. The residue was purified by column chromatography on silica gel (40-80% CH₂Cl₂ in heptane) to give the product as an off white solid (520 mg, 79%). ¹H NMR (300 MHz, CDCl₃) δ 8.11 (d, J=8.29 Hz, 2H), 7.72 (d, J=8.29 Hz, 2H), 7.62 (s, 1H), 7.28 (s, 1H), 3.76 (s, 3H), 3.71 (s, 2H). MS m/e 330.1 (M+H).

b) [2-(3,5-Bis-trifluoromethyl-phenyl)-6-(4-trifluoromethyl-phenyl)-pyridin-4-yl]-acetic acid methyl ester

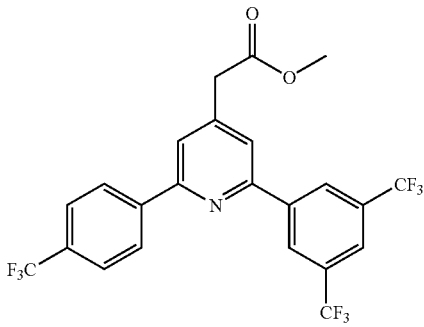

To a degassed solution of [2-chloro-6-(4-trifluoromethyl-phenyl)-pyridin-4-yl]-acetic acid methyl ester (165 mg, 0.5 mmol), 3,5-di(trifluoromethyl)benzeneboronic acid (160 mg, 0.6 mmol), 2N Na$_2$CO$_3$ (1.0 mL) in DME (9 mL) was added tetrakis(triphenylphosphine)palladium (70 mg, 0.06 mmol) under argon. The mixture was heated to 85° C. for 6 h, cooled to room temperature, diluted with water, and extracted with methylene chloride (3×). The organic solution was washed with brine, dried over Na$_2$SO$_4$, and concentrated. The residue was purified by column chromatography on silica gel (0-20% ethyl acetate in methylene chloride) to give the product as a white solid (150 mg, 59%). $^1$H NMR (300 MHz, CDCl$_3$) δ 8.57 (s, 2H), 8.24 (d, J=8.29 Hz, 2H), 7.96 (s, 1H), 7.73-7.85 (m, 4H), 3.83 (s, 2H), 3.78 (s, 3H). MS m/e 508.2 (M+H).

c) 2-[2-(3,5-Bis-trifluoromethyl-phenyl)-6-(4-trifluoromethyl-phenyl)-pyridin-4-yl]-4-methyl-pent-4-enoic acid methyl ester

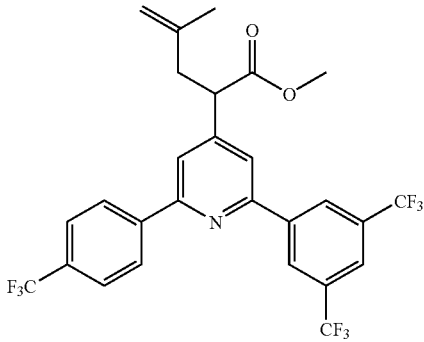

To a solution of [2-(3,5-bis-trifluoromethyl-phenyl)-6-(4-trifluoromethyl-phenyl)-pyridin-4-yl]-acetic acid methyl ester (150 mg, 0.3 mmol) in THF (5 mL) at −78° C. under argon was added potassium bis(trimethylsilyl)amide (0.5 M solution in toluene, 600 μL, 0.3 mmol). After stirring for 30 minutes, 3-bromo-2-methylpropene (40 mg, 0.3 mmol) was added and stirred for an additional 30 minutes. The reaction mixture was allowed to warm up slowly and stirred for another 30 minutes at 0° C. The mixture was then concentrated and purified by column chromatography on silica gel (20-60% methylene chloride in heptane) to give the product as a white solid (85 mg, 51%). $^1$H NMR (300 MHz, CDCl$_3$) δ 8.56 (s, 2H), 8.23 (d, J=8.29 Hz, 2H), 7.96 (s, 1H), 7.69-7.86 (m, 4H), 4.80 (d, J=19.59 Hz, 2H), 4.01 (dd, J=6.78, 9.04 Hz, 1H), 3.74 (s, 3H), 2.97 (dd, J=9.04, 14.69 Hz, 1H), 2.58 (dd, J=6.78, 14.69 Hz, 1H), 1.79 (s, 3H). MS m/e 562.2 (M+H).

d) 2-[2-(3,5-Bis-trifluoromethyl-phenyl)-6-(4-trifluoromethyl-phenyl)-pyridin-4-yl]-4-methyl-pentanoic acid methyl ester

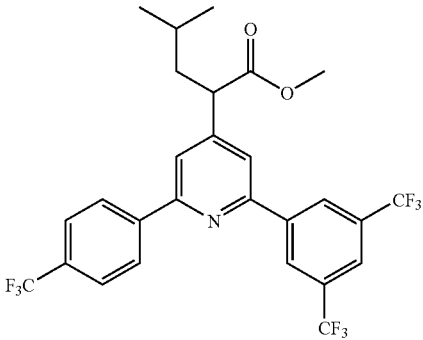

A solution of 2-[2-(3,5-Bis-trifluoromethyl-phenyl)-6-(4-trifluoromethyl-phenyl)-pyridin-4-yl]-4-methyl-pent-4-enoic acid methyl ester (80 mg, 0.14 mmol), Pd/C (10%, 10 mg) in methanol (10 mL) was hydrogenated for 4 h. The mixture was filtered through Celite, washed with methanol, evaporated. The residue was dissolved in CH$_2$Cl$_2$, filtered and evaporated to give the product as a colorless oil (80 mg, 100%). $^1$H NMR (300 MHz, CDCl$_3$) δ 8.56 (s, 2H), 8.24 (d, J=7.91 Hz, 2H), 7.96 (s, 1H), 7.70-7.85 (m, 4H), 3.80-3.92 (m, 1H), 3.73 (s, 3H), 2.14 (ddd, J=6.97, 8.48, 13.56 Hz, 1H), 1.76 (dt, J=7.06, 13.75 Hz, 1H), 1.50-1.65 (m, 1H), 0.98 (d, J=6.78 Hz, 6H). MS m/e 564.2 (M+H).

e) 2-[2-(3,5-Bis-trifluoromethyl-phenyl)-6-(4-trifluoromethyl-phenyl)-pyridin-4-yl]-4-methyl-pentanoic acid

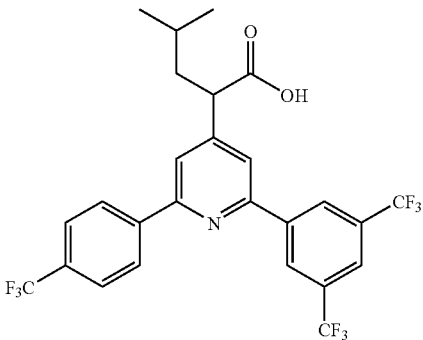

A solution of 2-[2-(3,5-bis-trifluoromethyl-phenyl)-6-(4-trifluoromethyl-phenyl)-pyridin-4-yl]-4-methyl-pentanoic acid methyl ester (80 mg, 0.14 mmol) in NaOH (1N, 1 mL) and THF (4 mL) was stirred at 40° C. overnight. The mixture was cooled to room temperature, acidified with 10% citric acid, extracted with CH$_2$Cl$_2$ (3×). The organic layer was washed with brine, dried over Na$_2$SO$_4$, filtered and evaporated. The residue was purified by chromatography (5-30% ethyl acetate in CH$_2$Cl$_2$) to give the product as a white solid (60 mg, 78%). $^1$H NMR (300 MHz, CDCl$_3$) δ 8.55 (s, 2H), 8.23 (d, J=7.91 Hz, 2H), 7.96 (s, 1H), 7.72-7.85 (m, 4H), 3.89 (t, J=7.91 Hz, 1H), 2.08-2.22 (m, 1H), 1.75-1.85 (m, 1H), 1.55-1.68 (m, 1H), 0.99 (d, J=6.40 Hz, 6H). MS m/e 550.2 (M+H).

Example 7

4-Methyl-2-[2-quinolin-3-yl-6-(4-trifluoromethyl-phenyl)-pyridin-4-yl]-pentanoic acid

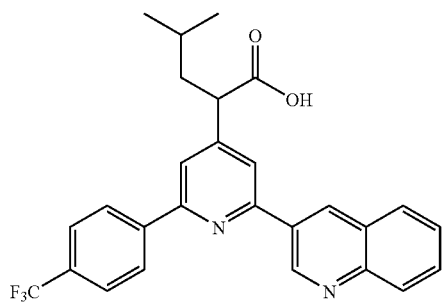

The title compound was prepared using 3-quinolineboronic acid in place of 3,5-di(trifluoromethyl)benzeneboronic acid as described in Example 6. $^1$H NMR (300 MHz, CD$_3$OD) δ 9.74 (d, J=2.26 Hz, 1H), 9.13 (d, J=2.26 Hz, 1H), 8.44 (d, J=8.29 Hz, 2H), 8.08-8.20 (m, 3H), 8.02 (s, 1H), 7.82-7.94 (m, 3H), 7.64-7.79 (m, 1H), 3.99 (t, J=7.91 Hz, 1H), 2.10-2.23 (m, 1H), 1.86 (dt, J=7.21, 13.85 Hz, 1H), 1.56-1.71 (m, 1H), 1.03 (dd, J=2.07, 6.59 Hz, 6H). MS m/e 465.1 (M+H).

Example 8

2-[2-(3-Fluoro-5-trifluoromethyl-phenyl)-6-(4-trifluoromethyl-phenyl)-pyridin-4-yl]-4-methyl-pentanoic acid

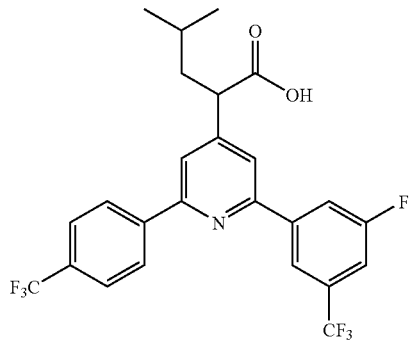

The title compound was prepared using 3-fluoro-5-trifluoromethylbenzeneboronic acid in place of 3,5-di(trifluoromethyl)benzeneboronic acid as described in Example 6. $^1$H NMR (400 MHz, CDCl$_3$) δ 8.22 (d, J=8.07 Hz, 2H), 8.14 (s, 1H), 8.07 (d, J=9.29 Hz, 1H), 7.74-7.82 (m, 3H), 7.71 (d, J=1.22 Hz, 1H), 7.41 (d, J=8.07 Hz, 1H), 3.86 (t, J=7.70 Hz, 1H), 2.13 (ddd, J=7.21, 8.19, 13.69 Hz, 1H), 1.79 (dt, J=7.03, 13.82 Hz, 1H), 1.54-1.66 (m, 1H), 0.98 (d, J=6.60 Hz, 6H). MS m/e 500.1 (M+H).

Example 9

2-[2-(4-Isopropyl-phenyl)-6-(4-trifluoromethyl-phenyl)-pyridin-4-yl]-4-methyl-pentanoic acid

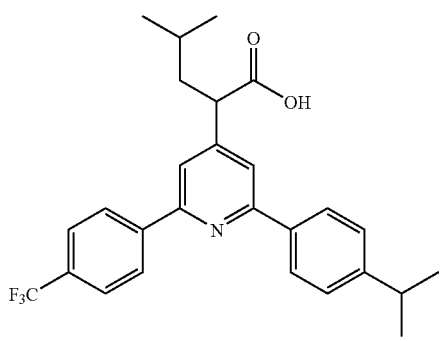

The title compound was prepared using 4-siopropylbenzeneboronic acid in place of 3,5-di(trifluoromethyl)benzeneboronic acid as described in Example 6. $^1$H NMR (300 MHz, CDCl$_3$) δ 8.23 (d, J=7.91 Hz, 2H), 8.03 (d, J=8.29 Hz, 2H), 7.73 (d, J=7.91 Hz, 2H), 7.66 (d, J=6.41 Hz, 2H), 7.35 (d, J=7.91 Hz, 2H), 3.79 (t, J=7.72 Hz, 1H), 2.90-3.05 (m, 1H), 1.99-2.15 (m, 1H), 1.77 (dt, J=7.06, 13.75 Hz, 1H), 1.49-1.63 (m, 1H), 1.29 (d, J=7.16 Hz, 6H), 0.94 (d, J=6.40 Hz, 6H). MS m/e 456.3 (M+H).

Example 10

2-[2-(3,5-Difluoro-phenyl)-6-(4-trifluoromethyl-phenyl)-pyridin-4-yl]-4-methyl-pentanoic acid

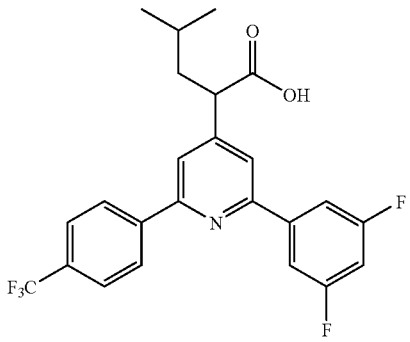

The title compound was prepared using 3,5-difluorobenzeneboronic acid in place of 3,5-di(trifluoromethyl)benzeneboronic acid as described in Example 6. $^1$H NMR (300 MHz, CDCl$_3$) δ 8.21 (d, J=8.29 Hz, 2H), 7.72-7.81 (m, 3H), 7.60-7.70 (m, 3H), 6.88 (tt, J=2.26, 8.67 Hz, 1H), 3.82 (t, J=7.72 Hz, 1H), 2.07-2.17 (m, 1H), 1.77 (dt, J=7.06, 13.75 Hz, 1H), 1.50-1.63 (m, 1H), 0.96 (d, J=6.40 Hz, 6H). MS m/e 450.1 (M+H).

Example 11

4-Methyl-2-[2-p-tolyl-6-(4-trifluoromethyl-phenyl)-pyridin-4-yl]-pentanoic acid

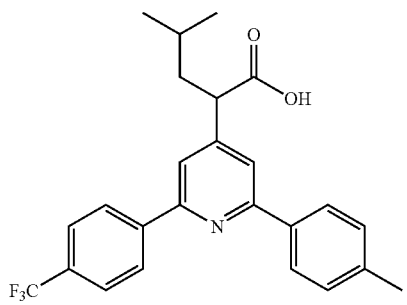

The title compound was prepared using 4-methylbenzeneboronic acid in place of 3,5-di(trifluoromethyl)benzeneboronic acid as described in Example 6. $^1$H NMR (300 MHz, CDCl$_3$) δ 8.22 (d, J=8.29 Hz, 2H), 8.01 (d, J=7.91 Hz, 2H), 7.73 (d, J=8.29 Hz, 2H), 7.65 (d, J=7.91 Hz, 2H), 7.29 (d, J=7.91 Hz, 2H), 3.79 (t, J=7.72 Hz, 1H), 2.42 (s, 3H), 2.04-2.13 (m, 1H), 1.77 (dt, J=7.06, 13.75 Hz, 1H), 1.50-1.63 (m, 1H), 0.95 (d, J=6.78 Hz, 6H). MS m/e 428.3 (M+H).

Example 12

4-Methyl-2-[2-(3-trifluoromethyl-phenyl)-6-(4-trifluoromethyl-phenyl)-pyridin-4-yl]-pentanoic acid

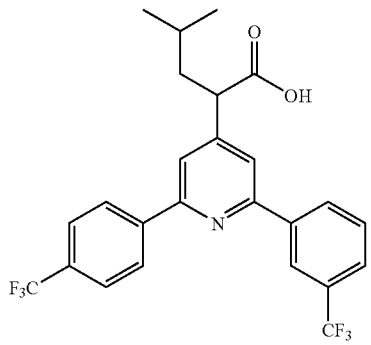

The title compound was prepared using 3-trifluoromethyl-benzeneboronic acid in place of 3,5-di(trifluoromethyl)benzeneboronic acid as described in Example 6. $^1$H NMR (300 MHz, CDCl$_3$) δ 8.35 (s, 1H), 8.29 (d, J=7.91 Hz, 1H), 8.22 (d, J=8.29 Hz, 2H), 7.67-7.81 (m, 5H), 7.57-7.66 (m, 1H), 3.84 (t, J=7.72 Hz, 1H), 2.07-2.18 (m, 1H), 1.79 (dt, J=6.97, 13.94 Hz, 1H), 1.52-1.64 (m, 1H), 0.97 (d, J=6.78 Hz, 6H). MS m/e 482.2 (M+H).

Example 13

2-[2-Biphenyl-4-yl-6-(4-trifluoromethyl-phenyl)-pyridin-4-yl]-4-methyl-pentanoic acid

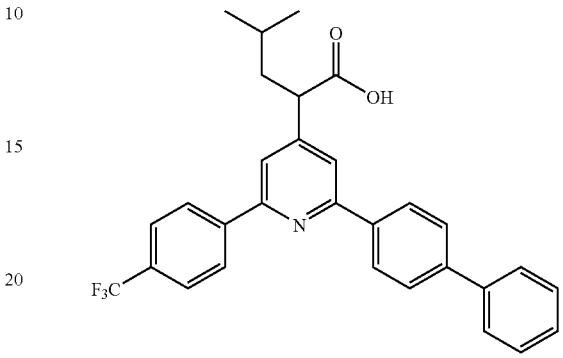

The title compound was prepared using 4-phenylbenzeneboronic acid in place of 3,5-di(trifluoromethyl)benzeneboronic acid as described in Example 6. $^1$H NMR (300 MHz, CDCl$_3$) δ 8.16-8.31 (m, 4H), 7.71-7.80 (m, 5H), 7.61-7.70 (m, 3H), 7.47 (t, J=7.35 Hz, 2H), 7.35-7.44 (m, 1H), 3.83 (t, J=7.72 Hz, 1H), 2.10 (dd, J=6.22, 7.72 Hz, 1H), 1.80 (dt, J=6.97, 13.94 Hz, 1H), 1.51-1.65 (m, 1H), 0.97 (d, J=6.40 Hz, 6H). MS m/e 490.2 (M+H).

Example 14

4-Methyl-2-[2-naphthalen-2-yl-6-(4-trifluoromethyl-phenyl)-pyridin-4-yl]-pentanoic acid

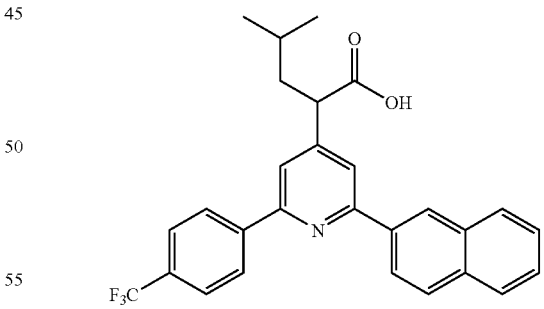

The title compound was prepared using 2-naphthaleneboronic acid in place of 3,5-di(trifluoromethyl)benzeneboronic acid as described in Example 6. $^1$H NMR (300 MHz, CDCl$_3$) δ 8.57 (s, 1H), 8.27 (d, J=8.29 Hz, 3H), 7.92-8.03 (m, 2H), 7.83-7.92 (m, 2H), 7.76 (d, J=7.91 Hz, 2H), 7.70 (s, 1H), 7.45-7.56 (m, 2H), 3.85 (t, J=7.72 Hz, 1H), 2.06-2.21 (m, 1H), 1.74-1.87 (m, 1H), 1.53-1.66 (m, 1H), 0.97 (d, J=6.78 Hz, 6H). MS m/e 464.1 (M+H).

Example 15

4-Methyl-2-[2-naphthalen-2-yl-6-(4-trifluoromethyl-phenyl)-pyridin-4-yl]-pent-4-enoic acid

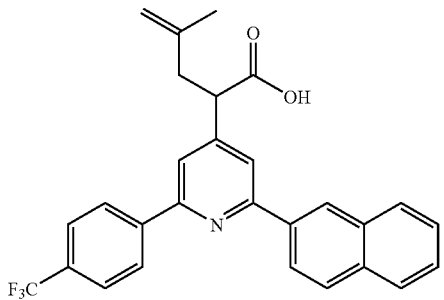

A solution of 4 4-methyl-2-[2-naphthalen-2-yl-6-(4-trifluoromethyl-phenyl)-pyridin-4-yl]-pent-4-enoic acid methyl ester (prepared using 2-naphthaleneboronic acid in place of 3,5-di(trifluoromethyl)benzeneboronic acid as described in Example 6) 30 mg, 0.06 mmol) in NaOH (1N, 0.5 mL) and THF (3 mL) was stirred at 40° C. overnight. The mixture was cooled to room temperature, acidified with 10% citric acid, extracted with $CH_2Cl_2$ (3×). The organic layer was washed with brine, dried over $Na_2SO_4$, filtered and evaporated. The residue was purified by chromatography (0-30% ethyl acetate in $CH_2Cl_2$) to give the product as a white solid (17 mg, 61%). $^1H$ NMR (300 MHz, $CDCl_3$) δ 8.57 (s, 1H), 8.27 (d, J=8.67 Hz, 3H), 7.92-8.03 (m, 2H), 7.83-7.92 (m, 2H), 7.76 (d, J=8.29 Hz, 2H), 7.71 (s, 1H), 7.48-7.57 (m, 2H), 4.81 (d, J=9.42 Hz, 2H), 4.01 (dd, J=6.97, 8.48 Hz, 1H), 2.97 (dd, J=8.67, 14.69 Hz, 1H), 2.61 (dd, J=6.78, 14.69 Hz, 1H), 1.78 (s, 3H). MS m/e 462.1 (M+H).

Example 16

2-[2-(2,4-Bis-trifluoromethyl-phenyl)-6-(4-trifluoromethyl-phenyl)-pyridin-4-yl]-4-methyl-pent-4-enoic acid

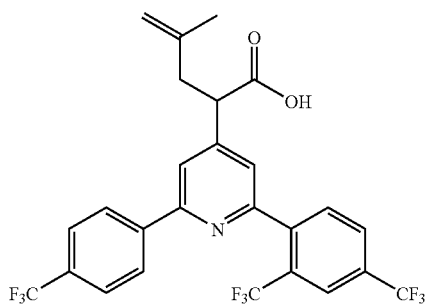

The title compound was prepared using 3,5-di(trifluoromethyl)benzeneboronic acid as described in Examples 6 and 15. $^1H$ NMR (300 MHz, $CDCl_3$) δ 8.14 (d, J=7.91 Hz, 2H), 8.06 (s, 1H), 7.91 (d, J=8.29 Hz, 1H), 7.78 (s, 1H), 7.72 (d, J=7.91 Hz, 3H), 7.43 (s, 1H), 4.68-4.85 (m, 2H), 3.96 (t, J=7.72 Hz, 1H), 2.90 (dd, J=8.29, 14.69 Hz, 1H), 2.57 (dd, J=7.16, 14.69 Hz, 1H), 1.75 (s, 3H). MS m/e 548.1 (M+H).

Example 17

2-[2-(2,4-Bis-trifluoromethyl-phenyl)-6-(4-trifluoromethyl-phenyl)-pyridin-4-yl]-4-methyl-pentanoic acid

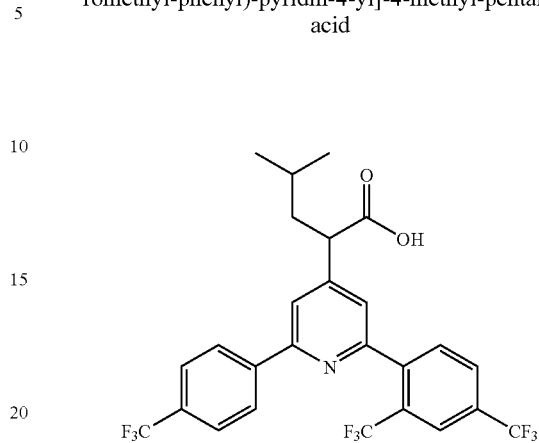

The title compound was prepared using 2,4-di(trifluoromethyl)benzeneboronic acid in place of 3,5-di(trifluoromethyl)benzeneboronic acid as described in Example 6. $^1H$ NMR (300 MHz, $CDCl_3$) δ 8.15 (d, J=8.29 Hz, 2H), 8.07 (s, 1H), 7.91 (d, J=8.29 Hz, 1H), 7.78 (s, 1H), 7.68-7.77 (m, 3H), 7.44 (s, 1H), 3.83 (t, J=7.72 Hz, 1H), 1.99-2.11 (m, 1H), 1.73-1.87 (m, 1H), 1.49-1.61 (m, 1H), 0.96 (d, J=6.78 Hz, 6H). MS m/e 550.3 (M+H).

Example 18

2-[2-Isoquinolin-4-yl-6-(4-trifluoromethyl-phenyl)-pyridin-4-yl]-4-methyl-pent-4-enoic acid

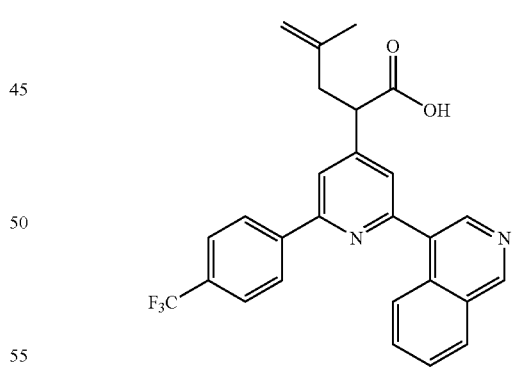

The title compound was prepared using 4-isoquinolineboronic acid pinacol ester in place of 3,5-di(trifluoromethyl)benzeneboronic acid as described in Examples 6 and 15. $^1H$ NMR (300 MHz, $CDCl_3$) δ 9.33 (s, 1H), 8.72 (s, 1H), 8.48 (d, J=8.67 Hz, 1H), 8.20 (d, J=8.29 Hz, 2H), 8.12 (d, J=7.91 Hz, 1H), 7.88 (s, 1H), 7.79-7.86 (m, 2H), 7.66-7.79 (m, 3H), 4.82 (d, J=9.42 Hz, 2H), 4.00-4.10 (m, 1H), 3.00 (dd, J=7.91, 14.69 Hz, 1H), 2.62 (dd, J=7.16, 14.69 Hz, 1H), 1.81 (s, 3H). MS m/e 463.2 (M+H).

Example 19

2-[2-Isoquinolin-4-yl-6-(4-trifluoromethyl-phenyl)-pyridin-4-yl]-4-methyl-pentanoic acid

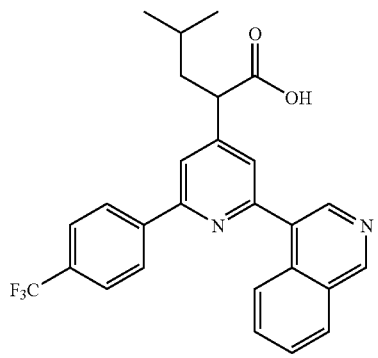

The title compound was prepared using 4-isoquinolineboronic acid pinacol ester in place of 3,5-di(trifluoromethyl)benzeneboronic acid as described in Example 6. $^1$H NMR (300 MHz, CDCl$_3$) δ 9.33 (s, 1H), 8.75 (s, 1H), 8.52 (d, J=8.29 Hz, 1H), 8.21 (d, J=8.29 Hz, 2H), 8.12 (d, J=7.91 Hz, 1H), 7.89 (s, 1H), 7.77-7.86 (m, 2H), 7.68-7.77 (m, 3H), 3.92 (t, J=7.72 Hz, 1H), 2.09-2.25 (m, 1H), 1.79 (dt, J=7.06, 13.75 Hz, 1H), 1.59-1.73 (m, 1H), 0.99 (d, J=6.40 Hz, 6H). MS m/e 465.1 (M+H).

Example 20

2-[2-(2,3-Difluoro-phenyl)-6-(4-trifluoromethyl-phenyl)-pyridin-4-yl]-4-methyl-pent-4-enoic acid

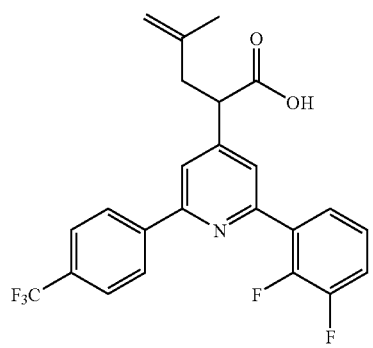

The title compound was prepared using 2,3-difluorobenzeneboronic acid in place of 3,5-di(trifluoromethyl)benzeneboronic acid as described in Examples 6 and 15. $^1$H NMR (300 MHz, CDCl$_3$): δ 8.18 (d, J=7.91 Hz, 2H), 7.81-7.96 (m, 1H), 7.65-7.81 (m, 4H), 7.06-7.36 (m, 2H), 4.78 (d, J=14.69 Hz, 2H), 3.97 (t, J=7.72 Hz, 1H), 2.92 (dd, J=8.29, 14.69 Hz, 1H), 2.59 (dd, J=7.16, 14.69 Hz, 1H), 1.77 (s, 3H). MS m/e 448.0 (M+H).

Example 21

2-[2-(2,3-Difluoro-phenyl)-6-(4-trifluoromethyl-phenyl)-pyridin-4-yl]-4-methyl-pentanoic acid

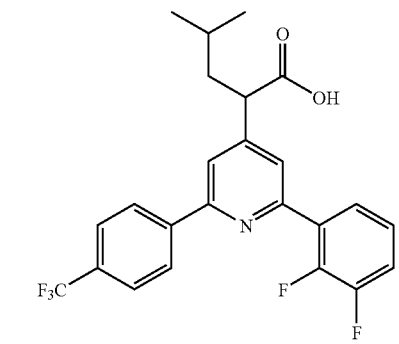

The title compound was prepared using 2,3-difluorobenzeneboronic acid in place of 3,5-di(trifluoromethyl)benzeneboronic acid as described in Example 6. $^1$H NMR (300 MHz, CDCl$_3$): δ 8.19 (d, J=7.91 Hz, 2H), 7.84-7.91 (m, 1H), 7.69-7.78 (m, 4H), 7.15-7.27 (m, 2H), 3.82 (t, J=7.91 Hz, 1H), 2.00-2.13 (m, 1H), 1.71-1.86 (m, 1H), 1.47-1.63 (m, 1H), 0.96 (d, J=6.65 Hz, 6H). MS m/e 450.1 (M+H).

Example 22

2-[2-(2,4-Difluoro-phenyl)-6-(4-trifluoromethyl-phenyl)-pyridin-4-yl]-4-methyl-pentanoic acid

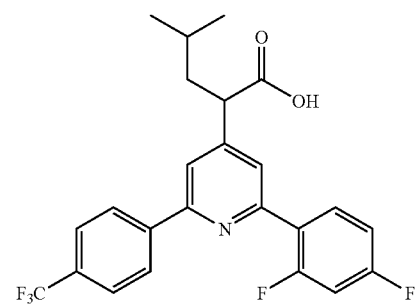

The title compound was prepared using 2,4-difluorobenzeneboronic acid in place of 3,5-di(trifluoromethyl)benzeneboronic acid as described in Examples 6. $^1$H NMR (300 MHz, CDCl$_3$): δ 8.13-8.22 (m, 3H), 7.67-7.79 (m, 4H), 7.03 (td, J=3.39, 8.29 Hz, 1H), 6.92 (ddd, J=2.45, 8.85, 11.30 Hz, 1H), 3.80 (t, J=7.72 Hz, 1H), 2.01-2.11 (m, 1H), 1.78 (dt, J=7.06, 13.75 Hz, 1H), 1.49-1.62 (m, 1H), 0.95 (d, J=6.7 Hz, 6H). MS m/e 450.1 (M+H).

Example 23

2-[2-(2,4-Difluoro-phenyl)-6-(4-trifluoromethyl-phenyl)-pyridin-4-yl]-4-methyl-pent-4-enoic acid

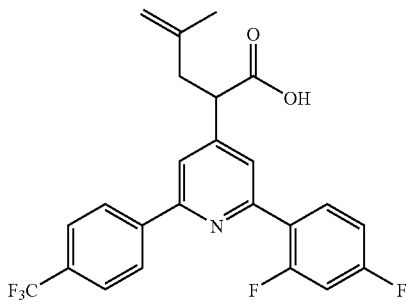

The title compound was prepared using 2,4-difluorobenzeneboronic acid in place of 3,5-di(trifluoromethyl)benzeneboronic acid as described in Examples 6 and 15. $^1$H NMR (300 MHz, CDCl$_3$): δ 8.10-8.22 (m, 3H), 7.66-7.77 (m, 4H), 7.03 (td, J=2.26, 8.29 Hz, 1H), 6.92 (ddd, J=2.45, 8.85, 11.30 Hz, 1H), 4.78 (d, J=14.32 Hz, 2H), 3.96 (t, J=7.72 Hz, 1H), 2.91 (dd, J=8.29, 14.69 Hz, 1H), 2.58 (dd, J=7.16, 14.69 Hz, 1H), 1.76 (s, 3H). MS m/e 448.0 (M+H).

Example 24

2-[2-(2,5-Difluoro-phenyl)-6-(4-trifluoromethyl-phenyl)-pyridin-4-yl]-4-methyl-pent-4-enoic acid

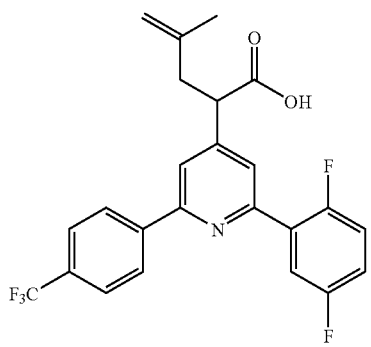

The title compound was prepared using 2,5-difluorobenzeneboronic acid in place of 3,5-di(trifluoromethyl)benzeneboronic acid as described in Examples 6 and 15. $^1$H NMR (300 MHz, CDCl$_3$): δ 8.19 (d, J=8.29 Hz, 2H), 7.89 (ddd, J=3.01, 6.12, 9.32 Hz, 1H), 7.81 (s, 1H), 7.69-7.78 (m, 3H), 7.04-7.17 (m, 2H), 4.78 (d, J=14.32 Hz, 2H), 3.96 (t, J=7.91 Hz, 1H), 2.91 (dd, J=8.67, 14.69 Hz, 1H), 2.58 (dd, J=7.16, 14.69 Hz, 1H), 1.76 (s, 3H). MS m/e 448.0 (M+H).

Example 25

2-[2-(2,5-Difluoro-phenyl)-6-(4-trifluoromethyl-phenyl)-pyridin-4-yl]-4-methyl-pentanoic acid

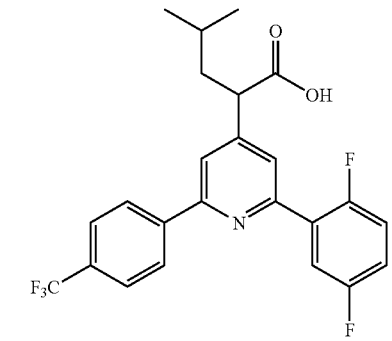

The title compound was prepared using 2,5-difluorobenzeneboronic acid in place of 3,5-di(trifluoromethyl)benzeneboronic acid as described in Example 6. $^1$H NMR (300 MHz, CDCl$_3$): δ 8.19 (d, J=7.91 Hz, 2H), 7.89 (ddd, J=3.01, 5.93, 9.14 Hz, 1H), 7.81 (s, 1H), 7.68-7.77 (m, 3H), 7.04-7.16 (m, 2H), 3.81 (t, J=7.91 Hz, 1H), 1.97-2.17 (m, 1H), 1.71-1.88 (m, 1H), 1.47-1.62 (m, 1H), 0.95 (d, J=6.45 Hz 6H). MS m/e 450.1 (M+H).

Example 26

2-[2-(2,6-Difluoro-phenyl)-6-(4-trifluoromethyl-phenyl)-pyridin-4-yl]-4-methyl-pentanoic acid

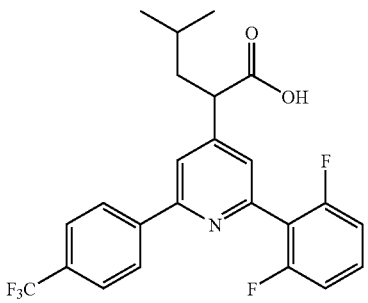

The title compound was prepared using 2,6-difluorobenzeneboronic acid in place of 3,5-di(trifluoromethyl)benzeneboronic acid as described in Example 6. $^1$H NMR (300 MHz, CDCl$_3$): δ 8.14 (d, J=8.29 Hz, 2H), 7.65-7.78 (m, 3H), 7.46 (s, 1H), 7.35 (tt, J=6.26, 8.43 Hz, 1H), 6.95-7.06 (m, 2H), 3.79 (t, J=7.72 Hz, 1H), 2.00-2.12 (m, 1H), 1.70-1.83 (m, 1H), 1.57 (dt, J=6.73, 13.28 Hz, 1H), 0.95 (d, J=6.50 Hz, 6H). MS m/e 450.1 (M+H).

Example 27

2-[2-(2,6-Difluoro-phenyl)-6-(4-trifluoromethyl-phenyl)-pyridin-4-yl]-4-methyl-pent-4-enoic acid

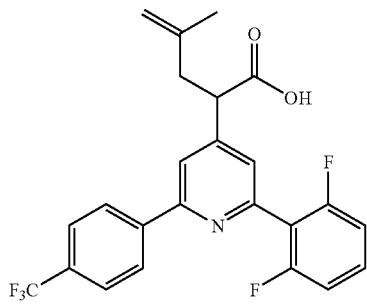

The title compound was prepared using 2,6-difluorobenzeneboronic acid in place of 3,5-di(trifluoromethyl)benzeneboronic acid as described in Examples 6 and 15. $^1$H NMR (300 MHz, CDCl$_3$): δ 8.13 (d, J=7.91 Hz, 2H), 7.66-7.78 (m, 3H), 7.45 (s, 1H), 7.28-7.40 (m, 1H), 6.91-7.07 (m, 2H), 4.77 (d, J=17.33 Hz, 2H), 3.93 (dd, J=6.97, 8.48 Hz, 1H), 2.89 (dd, J=8.29, 14.69 Hz, 1H), 2.55 (dd, J=7.16, 14.69 Hz, 1H), 1.75 (s, 3H). MS m/e 448.0 (M+H).

Example 28

2-[2-Benzo[b]thiophen-2-yl-6-(4-trifluoromethyl-phenyl)-pyridin-4-yl]-4-methyl-pent-4-enoic acid

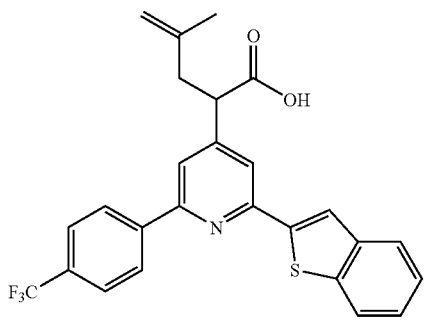

The title compound was prepared using benzothiophene-2-boronic acid in place of 3,5-di(trifluoromethyl)benzeneboronic acid as described in Examples 6 and 15. $^1$H NMR (300 MHz, DMSO-d$_6$) δ 8.42 (d, J=8.29 Hz, 2H), 8.33 (s, 1H), 8.16 (s, 1H), 8.02-8.07 (m, 2H), 7.88-7.99 (m, 3H), 7.37-7.48 (m, 2H), 4.74 (d, J=9.42 Hz, 2H), 4.07 (t, J=7.72 Hz, 1H), 2.87 (s, 1H), 2.74 (s, 1H), 1.75 (s, 3H). MS m/e 468.1 (M+H).

Example 29

2-[2-Benzo[b]thiophen-2-yl-6-(4-trifluoromethyl-phenyl)-pyridin-4-yl]-4-methyl-pentanoic acid

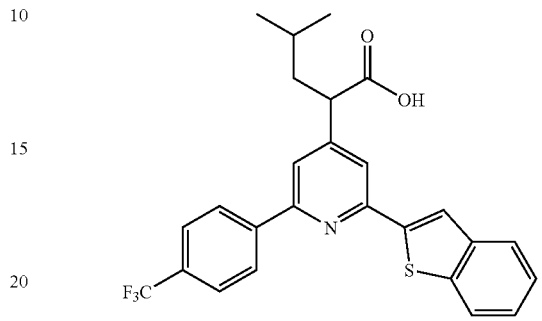

The title compound was prepared using benzothiophene-2-boronic acid in place of 3,5-di(trifluoromethyl)benzeneboronic acid as described in Example 6. $^1$H NMR (300 MHz, CD$_3$OD) δ 8.38 (d, J=8.29 Hz, 2H), 8.08 (s, 1H), 7.97 (s, 1H), 7.79-7.94 (m, 5H), 7.33-7.44 (m, 2H), 3.91 (t, J=7.72 Hz, 1H), 2.04-2.18 (m, 1H), 1.81 (dt, J=7.06, 13.75 Hz, 1H), 1.55-1.66 (m, 1H), 1.01 (d, J=6.78 Hz, 6H). MS m/e 470.1 (M+H).

Example 30

4-Methyl-2-[6'-trifluoromethyl-6-(4-trifluoromethyl-phenyl)-[2,3']bipyridinyl-4-yl]-pentanoic acid

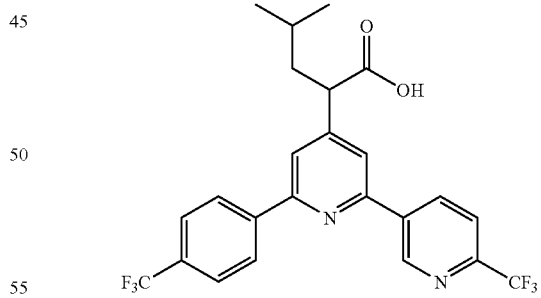

The title compound was prepared using 2-(trifluoromethyl)pyridine-5-ylboronic acid in place of 3,5-di(trifluoromethyl)benzeneboronic acid as described in Example 6. $^1$H NMR (300 MHz, CDCl$_3$): δ 9.46 (s, 1H), 8.66 (dd, J=1.70, 8.10 Hz, 1H), 8.22 (d, J=7.91 Hz, 2H), 7.71-7.90 (m, 5H), 3.89 (t, J=7.72 Hz, 1H), 2.07-2.19 (m, 1H), 1.79 (dt, J=7.06, 13.75 Hz, 1H), 1.51-1.66 (m, 1H), 0.93-1.02 (m, 6H), 0.97 (d, J=6.41 Hz, 6H). MS m/e 483.1 (M+H).

Example 31

4-Methyl-2-[6'-trifluoromethyl-6-(4-trifluoromethyl-phenyl)-[2,3']bipyridinyl-4-yl]-pent-4-enoic acid

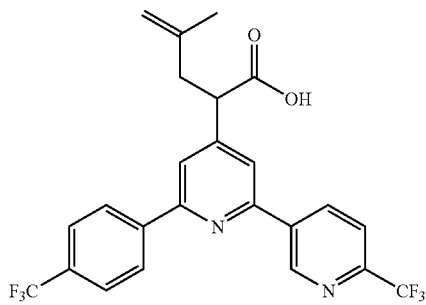

The title compound was prepared using 2-(trifluoromethyl)pyridine-5-ylboronic acid in place of 3,5-di(trifluoromethyl)benzeneboronic acid as described in Examples 6 and 15. $^1$H NMR (300 MHz, CDCl$_3$): δ 9.46 (d, J=1.51 Hz, 1H), 8.68 (dd, J=1.70, 8.10 Hz, 1H), 8.21 (d, J=7.91 Hz, 2H), 7.70-7.93 (m, 5H), 4.80 (d, J=17.33 Hz, 2H), 4.04 (t, J=7.72 Hz, 1H), 2.96 (dd, J=8.29, 14.69 Hz, 1H), 2.60 (dd, J=7.16, 14.69 Hz, 1H), 1.78 (s, 3H). MS m/e 481.1 (M+H).

Example 32

4-Methyl-2-[2-p-tolyl-6-(4-trifluoromethyl-phenyl)-pyridin-4-yl]-pent-4-enoic acid

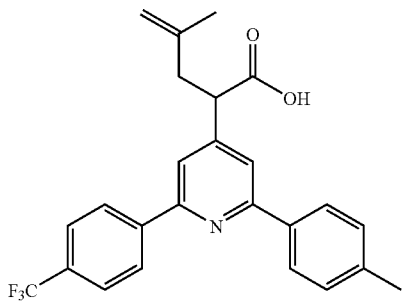

The title compound was prepared using 4-methylbenzeneboronic acid in place of 3,5-di(trifluoromethyl)benzeneboronic acid as described in Examples 6 and 15. $^1$H NMR (300 MHz, CDCl$_3$) δ 8.21 (d, J=8.29 Hz, 2H), 7.99 (d, J=7.91 Hz, 2H), 7.72 (d, J=8.29 Hz, 2H), 7.65 (d, J=8.67 Hz, 2H), 7.22-7.33 (m, 2H), 4.77 (d, J=12.43 Hz, 2H), 3.93 (dd, J=6.97, 8.48 Hz, 1H), 2.91 (dd, J=8.48, 14.51 Hz, 1H), 2.55 (dd, J=6.78, 14.69 Hz, 1H), 2.40 (s, 3H), 1.75 (s, 3H). MS m/e 426.1 (M+H).

Example 33

2-[2-Benzo[1,3]dioxol-5-yl-6-(4-trifluoromethyl-phenyl)-pyridin-4-yl]-4-methyl-pentanoic acid

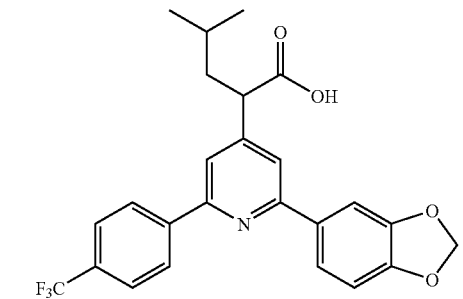

The title compound was prepared using 3,4-(methylenedioxy)phenylboronic acid in place of 3,5-di(trifluoromethyl)benzeneboronic acid as described in Example 6. $^1$H NMR (300 MHz, CDCl$_3$) δ 8.21 (d, J=8.29 Hz, 2H), 7.73 (d, J=8.29 Hz, 2H), 7.67 (d, J=1.51 Hz, 1H), 7.57-7.66 (m, 3H), 6.91 (d, J=8.29 Hz, 1H), 6.03 (s, 2H), 3.78 (t, J=7.72 Hz, 1H), 2.01-2.12 (m, 1H), 1.76 (dt, J=7.06, 13.75 Hz, 1H), 1.56 (dt, J=6.73, 13.28 Hz, 1H), 0.95 (d, J=6.40 Hz, 6H). MS m/e 458.3 (M+H).

Example 34

2-[2-Biphenyl-3-yl-6-(4-trifluoromethyl-phenyl)-pyridin-4-yl]-4-methyl-pent-4-enoic acid

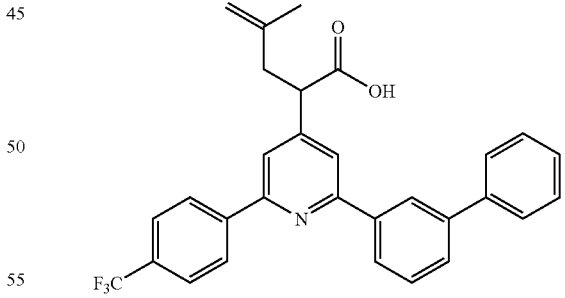

The title compound was prepared using 3-phenylbenzeneboronic acid in place of 3,5-di(trifluoromethyl)benzeneboronic acid as described in Examples 6 and 15. $^1$H NMR (300 MHz, CDCl$_3$) δ 8.30 (s, 1H), 8.23 (d, J=7.91 Hz, 2H), 8.06 (d, J=7.91 Hz, 1H), 7.62-7.81 (m, 7H), 7.34-7.59 (m, 4H), 4.79 (d, J=12.06 Hz, 2H), 3.97 (t, J=7.72 Hz, 1H), 2.94 (dd, J=8.67, 14.69 Hz, 1H), 2.58 (dd, J=6.78, 14.69 Hz, 1H), 1.76 (s, 3H). MS m/e 488.3 (M+H).

Example 35

2-[2-Biphenyl-3-yl-6-(4-trifluoromethyl-phenyl)-pyridin-4-yl]-4-methyl-pentanoic acid

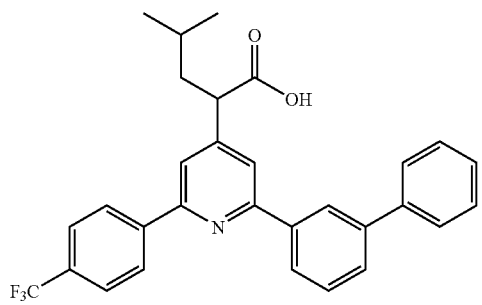

The title compound was prepared using 3-phenylbenzeneboronic acid in place of 3,5-di(trifluoromethyl)benzeneboronic acid as described in Example 6. $^1$H NMR (300 MHz, CDCl$_3$) δ 8.30 (s, 1H), 8.23 (d, J=7.91 Hz, 2H), 8.06 (d, J=7.91 Hz, 1H), 7.60-7.82 (m, 7H), 7.33-7.58 (m, 4H), 3.82 (t, J=7.72 Hz, 1H), 2.02-2.17 (m, 1H), 1.78 (dt, J=7.11, 14.03 Hz, 1H), 1.50-1.64 (m, 1H), 0.95 (d, J=6.78 Hz, 6H). MS m/e 490.2 (M+H).

Example 36

2-[2-(3-Isobutoxy-phenyl)-6-(4-trifluoromethyl-phenyl)-pyridin-4-yl]-4-methyl-pentanoic acid

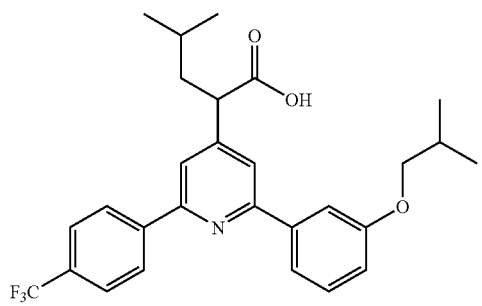

The title compound was prepared using 3-isobutoxyphenylboronic acid in place of 3,5-di(trifluoromethyl)benzeneboronic acid as described in Example 6. $^1$H NMR (300 MHz, CDCl$_3$) δ 8.23 (d, J=8.29 Hz, 2H), 7.74 (d, J=8.29 Hz, 2H), 7.61-7.70 (m, 4H), 7.39 (t, J=7.91 Hz, 1H), 6.98 (dd, J=1.70, 8.10 Hz, 1H), 3.74-3.87 (m, 3H), 2.03-2.19 (m, 2H), 1.78 (dt, J=7.21, 13.85 Hz, 1H), 1.50-1.63 (m, 1H), 1.06 (d, J=6.78 Hz, 6H), 0.95 (d, J=6.40 Hz, 6H). MS m/e 486.3 (M+H).

Example 37

4-Methyl-2-[2-(4-phenoxy-phenyl)-6-(4-trifluoromethyl-phenyl)-pyridin-4-yl]-pentanoic acid

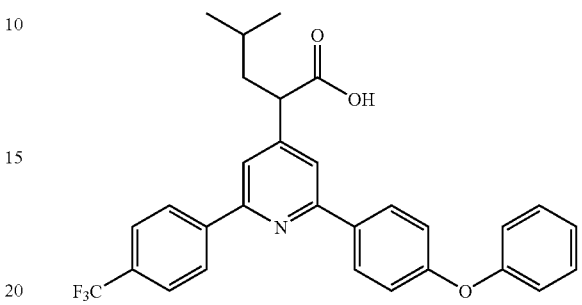

The title compound was prepared using 4-phenoxyphenylboronic acid in place of 3,5-di(trifluoromethyl)benzeneboronic acid as described in Example 6. $^1$H NMR (300 MHz, CDCl$_3$) δ 8.22 (d, J=7.91 Hz, 2H), 8.10 (d, J=9.04 Hz, 2H), 7.73 (d, J=8.29 Hz, 2H), 7.65 (d, J=3.39 Hz, 2H), 7.31-7.44 (m, 2H), 7.00-7.20 (m, 5H), 3.80 (t, J=7.72 Hz, 1H), 1.97-2.15 (m, 1H), 1.78 (dt, J=6.97, 13.94 Hz, 1H), 1.57 (dt, J=6.73, 13.28 Hz, 1H), 0.96 (d, J=6.40 Hz, 3H). MS m/e 506.2 (M+H).

Example 38

4-Methyl-2-[2-phenyl-6-(4-trifluoromethyl-phenyl)-pyridin-4-yl]-pentanoic acid

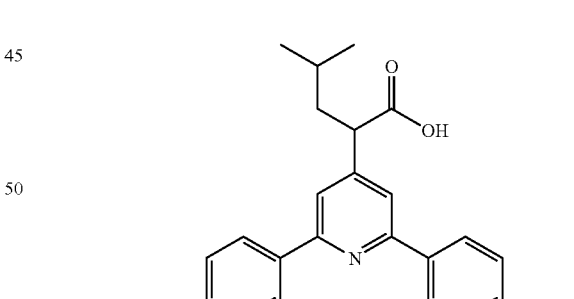

The title compound was prepared using benzeneboronic acid in place of 3,5-di(trifluoromethyl)benzeneboronic acid as described in Example 6. $^1$H NMR (300 MHz, CDCl$_3$) δ 8.24 (d, J=8.29 Hz, 2H), 8.05-8.17 (m, 2H), 7.72 (dd, J=7.91, 13.94 Hz, 4H), 7.41-7.58 (m, 3H), 3.82 (t, J=7.91 Hz, 1H), 2.09 (dt, J=7.68, 13.66 Hz, 1H), 1.71-1.86 (m, 1H), 1.58 (dt, J=6.64, 13.47 Hz, 1H), 0.96 (d, J=6.78 Hz, 6H). MS m/e 414.1 (M+H).

Example 39

2-[2-(4-Methanesulfonyl-phenyl)-6-(4-trifluoromethyl-phenyl)-pyridin-4-yl]-4-methyl-pentanoic acid

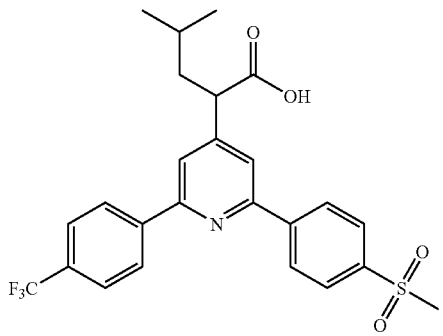

The title compound was prepared using 4-methylsulfonylphenylboronic acid in place of 3,5-di(trifluoromethyl)benzeneboronic acid as described in Example 6. $^1$H NMR (300 MHz, CDCl$_3$) δ 8.64 (s, 1H), 8.45 (d, J=7.91 Hz, 1H), 8.22 (d, J=7.91 Hz, 2H), 8.02 (d, J=8.29 Hz, 1H), 7.67-7.82 (m, 5H), 3.85 (t, J=7.72 Hz, 1H), 2.13 (dt, J=7.68, 13.66 Hz, 1H), 1.79 (dt, J=7.06, 13.75 Hz, 1H), 1.59 (dt, J=6.73, 13.28 Hz, 1H), 0.97 (d, J=6.40 Hz, 6H). MS m/e 492.1 (M+H).

Example 40

2-[2-[Isobutyl-(4-trifluoromethyl-phenyl)-amino]-6-(4-trifluoromethyl-phenyl)-pyridin-4-yl]-4-methyl-pentanoic acid

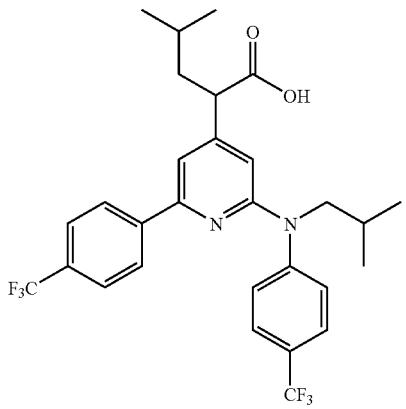

a) (6-Chloro-4-methyl-pyridin-2-yl)-(4-trifluoromethyl-phenyl)-amine

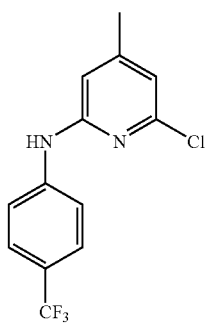

To a solution of 2-bromo-6-chloro-4-methylpyridine (415 mg, 2.0 mmol) in toluene (10 mL) was added 4-trifluoromethylaniline (325 mg, 2.0 mL), Pd$_2$(dba)$_3$ (50 mg, XANT-PHOS (50 mg), and t-BuOK (350 mg). The mixture was microwaved 30 minutes at 120° C., filtered through Celite and washed with CH$_2$Cl$_2$ (3×). The combined organic layers were concentrated. The residue was purified by chromatography on silica gel (20-40% CH$_2$Cl$_2$ heptane) to give the product as a white solid (320 mg, 56%). $^1$H NMR (300 MHz, CDCl$_3$) δ 7.53-7.63 (m, 2H), 7.41-7.49 (m, 2H), 6.70 (s, 1H), 6.61 (s, 2H), 2.28 (s, 3H). MS m/e 287.1 (M+H)

b) (6-Chloro-4-methyl-pyridin-2-yl)-(2-methyl-allyl)-(4-trifluoromethyl-phenyl)-amine

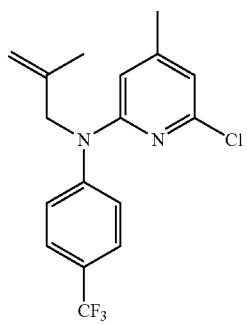

To a solution of (6-chloro-4-methyl-pyridin-2-yl)-(4-trifluoromethyl-phenyl)-amine (290 mg, 1.0 mmol) in THF (10 mL) was added NaH (60%, 80 mg, 2.0 mmol) and 1-bromo-3-methylpropene (150 mg, 1.1 mmol). The mixture was microwaved 20 minutes at 120° C. and concentrated. The residue was purified by chromatography on silica gel (10-30% CH$_2$Cl$_2$ in heptane) to give the product as a colorless oil (230 mg, 68%). $^1$H NMR (300 MHz, CDCl$_3$) δ 7.58 (d, J=8.29 Hz, 2H), 7.34 (d, J=8.67 Hz, 2H), 6.59 (s, 1H), 6.45 (s, 1H), 4.81 (d, J=15.07 Hz, 2H), 4.55 (s, 2H), 2.18 (s, 3H), 1.76 (s, 3H). MS m/e 341.1 (M+H), c) (2-Methyl-allyl)-[4-methyl-6-(4-trifluoromethyl-phenyl)-pyridin-2-yl]-(4-trifluoromethyl-phenyl)-amine

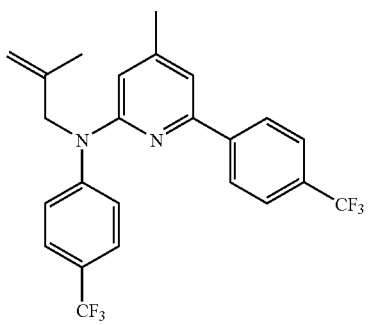

To a degassed solution of (6-chloro-4-methyl-pyridin-2-yl)-(2-methyl-allyl)-(4-trifluoromethyl-phenyl)-amine (340 mg, 1.0 mmol), 4-trifluoromethylbenzeneboronic acid (230 mg, 1.2 mmol), 2N Na$_2$CO$_3$ (1.5 mL) in DME (10 mL) was added tetrakis(triphenylphosphine)palladium (120 mg, 0.1 mmol) under argon. The mixture was heated to 85° C. for 4 h, cooled to room temperature, diluted with water, and extracted with methylene chloride (3×). The organic solution was washed with brine, dried over Na₂SO₄, and concentrated. The residue was purified by column chromatography on silica gel (5-20% methylene chloride in methylene chloride) to give the product as a white solid (270 mg, 60%). ¹H NMR (300 MHz, CDCl₃) δ 8.09 (d, J=7.91 Hz, 2H), 7.69 (d, J=8.29 Hz, 2H), 7.59 (d, J=8.67 Hz, 2H), 7.39 (d, J=8.67 Hz, 2H), 7.11 (s, 1H), 6.66 (s, 1H), 4.86 (s, 2H), 4.70 (s, 2H), 2.30 (s, 3H), 1.81 (s, 3H). MS m/e 451.2 (M+H).

d) Isobutyl-[4-methyl-6-(4-trifluoromethyl-phenyl)-pyridin-2-yl]-(4-trifluoromethyl-phenyl)-amine

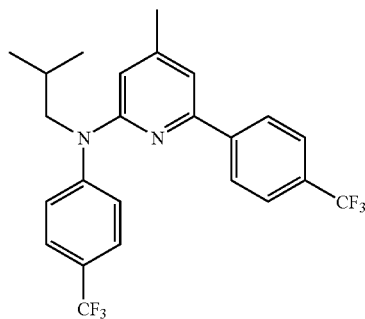

A solution of (2-methyl-allyl)-[4-methyl-6-(4-trifluoromethyl-phenyl)-pyridin-2-yl]-(4-trifluoromethyl-phenyl)-amine (270 mg, 0.6 mmol), Pd/C (10%, 30 mg) in methanol (30 mL) was hydrogenated for 4 h. The mixture was filtered through Celite, washed with methanol, and evaporated. The residue was dissolved in CH₂Cl₂, filtered and evaporated to give the product as a white solid (250 mg, 92%). ¹H NMR (300 MHz, CDCl₃) δ 8.12 (d, J=7.91 Hz, 2H), 7.70 (d, J=8.29 Hz, 2H), 7.58-7.66 (m, 2H), 7.38 (d, J=8.29 Hz, 2H), 7.06 (s, 1H), 6.45 (s, 1H), 3.95 (d, J=7.16 Hz, 2H), 2.25 (s, 3H), 2.10-2.22 (m, 1H), 0.98 (d, J=6.78 Hz, 6H). MS m/e 453.3 (M+H).

e) [2-[Isobutyl-(4-trifluoromethyl-phenyl)-amino]-6-(4-trifluoromethyl-phenyl)-pyridin-4-yl]-acetic acid methyl ester

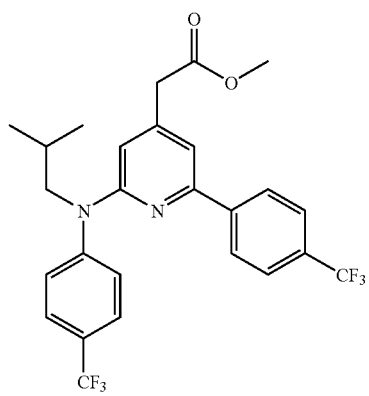

A solution of LDA (1.8 M in THF/heptane/ethyl benzene, 340 mL, 0.6 mmol) was added slowly to a stirred solution of isobutyl-[4-methyl-6-(4-trifluoromethyl-phenyl)-pyridin-2-yl]-(4-trifluoromethyl-phenyl)-amine (135 g, 0.3 mmol) under N₂ at −78° C. After 30 minutes dimethyl carbonate (55 mg, 0.6 mmol) was added. After stirring at −78° C. for 30 minutes, the solution was allowed to warm up slowly and stirred at 0° C. for 30 minutes. The reaction was quenched with saturated aqueous NH₄Cl (1 mL). The mixture was partitioned between CH₂Cl₂ and H₂O. The aqueous layer was extracted with CH₂Cl₂ (2×). The combined extracts were washed with brine, then dried (Na₂SO₄), filtered and evaporated. The residue was purified by column chromatography on silica gel (40-80% CH₂Cl₂ in heptane) to give the product as light yellow oil (75 mg, 49%). ¹H NMR (300 MHz, CDCl₃) δ 8.12 (d, J=7.91 Hz, 2H), 7.70 (d, J=8.29 Hz, 2H), 7.65 (d, J=8.29 Hz, 2H), 7.40 (d, J=8.29 Hz, 2H), 7.14 (s, 1H), 6.50 (s, 1H), 3.96 (d, J=7.16 Hz, 2H), 3.69 (s, 3H), 3.51 (s, 2H), 2.05-2.22 (m, 1H), 0.98 (d, J=6.78 Hz, 6H). MS m/e 511.2 (M+H).

f) 2-[2-[Isobutyl-(4-trifluoromethyl-phenyl)-amino]-6-(4-trifluoromethyl-phenyl)-pyridin-4-yl]-4-methyl-pent-4-enoic acid methyl ester

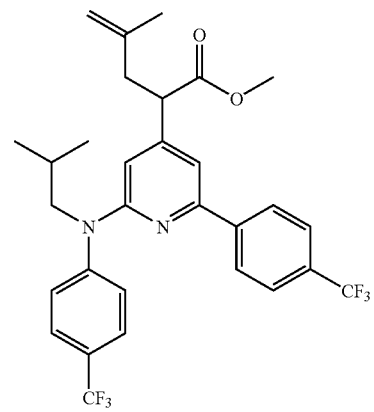

To a solution of [2-[isobutyl-(4-trifluoromethyl-phenyl)-amino]-6-(4-trifluoromethyl-phenyl)-pyridin-4-yl]-acetic acid methyl ester (75 mg, 0.15 mmol) in THF (5 mL) at −78° C. under argon was added potassium bis(trimethylsilyl)amide (0.5 M solution in toluene, 300 μL, 0.15 mmol). After stirring for 30 minutes, 3-bromo-2-methylpropene (20 mg, 0.15 mmol) was added and stirred for an additional 30 minutes The reaction mixture was allowed to warm up slowly and stirred for another 30 minutes at 0° C. The mixture was then concentrated and purified by column chromatography on silica gel (0-30% methylene chloride in heptane) to give the product as a white solid (40 mg, 47%). ¹H NMR (300 MHz, CDCl₃) δ 8.12 (d, J=8.29 Hz, 2H), 7.71 (d, J=8.29 Hz, 2H), 7.57-7.68 (m, 2H), 7.38 (d, J=8.29 Hz, 2H), 7.19 (s, 1H), 6.55 (s, 1H), 4.61-4.79 (m, 2H), 3.96 (d, J=7.54 Hz, 2H), 3.67 (s, 3H), 2.68-2.85 (m, 1H), 2.31-2.47 (m, 1H), 2.07-2.26 (m, 1H), 1.70 (s, 3H), 0.89-1.05 (m, 6H). MS m/e 565.3 (M+H).

g) 2-[2-[Isobutyl-(4-trifluoromethyl-phenyl)-amino]-6-(4-trifluoromethyl-phenyl)-pyridin-4-yl]-4-methyl-pentanoic acid methyl ester

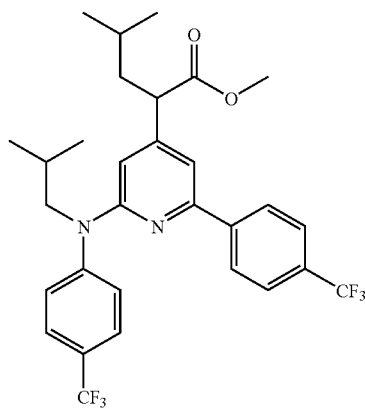

A solution of 2-[2-[isobutyl-(4-trifluoromethyl-phenyl)-amino]-6-(4-trifluoromethyl-phenyl)-pyridin-4-yl]-4-methyl-pent-4-enoic acid methyl ester (40 mg, 0.07 mmol), Pd/C (10%, 5 mg) in methanol (10 mL) was hydrogenated for 4 h. The mixture was filtered through Celite, washed with methanol, evaporated. The residue was dissolved in $CH_2Cl_2$, filtered and evaporated to give the product as colorless oil (40 mg, 100%). $^1$H NMR (300 MHz, $CDCl_3$) δ 8.12 (d, J=8.29 Hz, 2H), 7.70 (d, J=8.29 Hz, 2H), 7.64 (d, J=8.67 Hz, 2H), 7.38 (d, J=8.67 Hz, 2H), 7.18 (s, 1H), 6.57 (s, 1H), 3.96 (d, J=7.16 Hz, 2H), 3.66 (s, 3H), 2.10-2.23 (m, 1H), 1.90 (dt, J=7.72, 13.56 Hz, 1H), 1.62 (dt, J=6.92, 13.66 Hz, 1H), 1.40-1.52 (m, 1H), 0.97 (d, J=6.78 Hz, 6H), 0.89 (dd, J=4.33, 6.59 Hz, 5H). MS m/e 567.3 (M+H).

h) 2-[2-[Isobutyl-(4-trifluoromethyl-phenyl)-amino]-6-(4-trifluoromethyl-phenyl)-pyridin-4-yl]-4-methyl-pentanoic acid

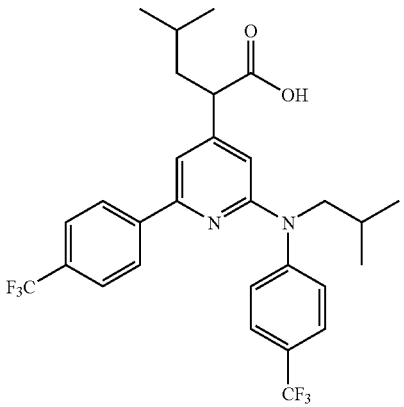

A solution of 2-[2-[isobutyl-(4-trifluoromethyl-phenyl)-amino]-6-(4-trifluoromethyl-phenyl)-pyridin-4-yl]-4-methyl-pentanoic acid methyl ester (40 mg, 0.07 mmol) in NaOH (1N, 0.5 mL) and THF (3 mL) was stirred at 40° C. overnight. The mixture was cooled to room temperature, acidified with 10% citric acid, and extracted with $CH_2Cl_2$ (3×). The organic layer was washed with brine, dried over $Na_2SO_4$, filtered and evaporated. The residue was purified by chromatography (5-20% ethyl acetate in $CH_2Cl_2$) to give the product as a white solid (28 mg, 71%). $^1$H NMR (300 MHz, $CDCl_3$) δ 8.11 (d, J=8.29 Hz, 2H), 7.70 (d, J=8.29 Hz, 2H), 7.57-7.67 (m, 2H), 7.38 (d, J=8.29 Hz, 2H), 7.18 (s, 1H), 6.57 (s, 1H), 3.96 (d, J=7.54 Hz, 2H), 3.55 (t, J=7.54 Hz, 1H), 2.07-2.23 (m, 1H), 1.83-1.95 (m, 1H), 1.65 (dt, J=7.06, 13.75 Hz, 1H), 1.52 (dd, J=6.59, 13.37 Hz, 1H), 0.97 (d, J=6.78 Hz, 6H), 0.90 (dd, J=4.52, 6.40 Hz, 6H). MS m/e 553.3 (M+H).

Example 41

4-Methyl-2-[2-[(3-methyl-butyl)-(4-trifluoromethyl-phenyl)-amino]-6-(4-trifluoromethyl-phenyl)-pyridin-4-yl]-pentanoic acid

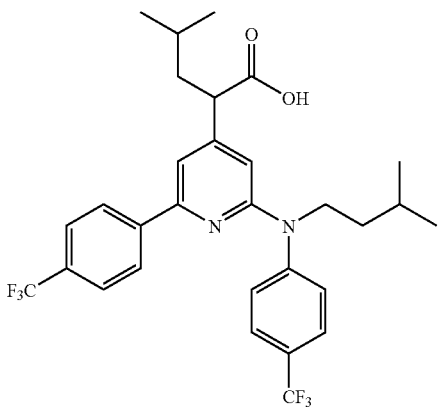

The title compound was prepared using 3-methyl-iodobutane in place of 3-bromo-2-methylpropene as described in Example 41. $^1$H NMR (300 MHz, $CDCl_3$) δ 8.11 (d, J=8.29 Hz, 2H), 7.70 (d, J=8.29 Hz, 2H), 7.58-7.68 (m, 2H), 7.38 (d, J=8.29 Hz, 2H), 7.18 (s, 1H), 6.57 (s, 1H), 3.96 (d, J=7.54 Hz, 2H), 3.55 (t, J=7.54 Hz, 1H), 2.09-2.25 (m, 1H), 1.84-1.98 (m, 1H), 1.46-1.70 (m, 3H), 0.97 (d, J=6.78 Hz, 6H), 0.90 (dd, J=4.52, 6.40 Hz, 6H). MS m/e 567.2 (M+H).

Example 42

[2-[(3-Methyl-butyl)-(4-trifluoromethyl-phenyl)-amino]-6-(4-trifluoromethyl-phenyl)-pyridin-4-yl]-acetic acid

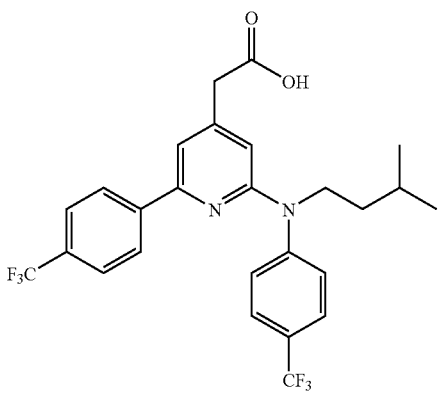

A solution of [2-[(3-methyl-butyl)-(4-trifluoromethyl-phenyl)-amino]-6-(4-trifluoromethyl-phenyl)-pyridin-4-yl]-acetic acid methyl ester (prepared using 3-methyl-iodo-butane in place of 3-bromo-2-methylprepene as described in Example 41) 55 mg, 0.1 mmol) in NaOH (1N, 0.5 mL) and THF (3 mL) was stirred at 40° C. overnight. The mixture was cooled to room temperature, acidified with 10% citric acid, extracted with $CH_2Cl_2$ (3×). The organic layer was washed with brine, dried over Na$_2$SO$_4$, filtered and evaporated. The residue was purified by chromatography (5-20% ethyl acetate in CH$_2$Cl$_2$) to give the product as a white solid (50 mg, 59%). $^1$H NMR (300 MHz, CDCl$_3$) δ 8.13 (d, J=8.29 Hz, 2H), 7.68 (dd, J=8.48, 13.37 Hz, 4H), 7.38 (d, J=8.29 Hz, 2H), 7.14 (s, 1H), 6.47 (s, 1H), 4.12 (d, J=15.45 Hz, 2H), 3.55 (s, 2H), 1.58-1.68 (m, 3H), 0.96 (d, J=6.40 Hz, 6H). MS m/e 511.2 (M+H).

Example 43

[2-[(2-Cyclohexyl-ethyl)-(4-trifluoromethyl-phenyl)-amino]-6-(4-trifluoromethyl-phenyl)-pyridin-4-yl]-acetic acid

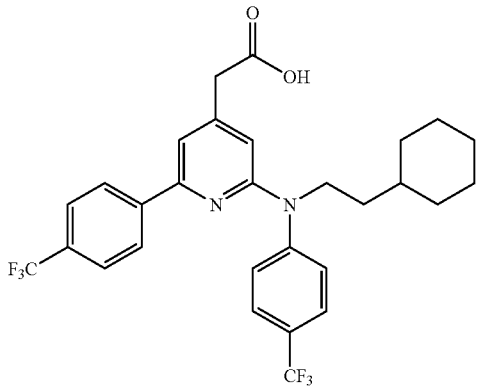

The title compound was prepared using 2-cyclohexylethylbromide in place of 3-bromo-2-methylpropene as described in Examples 41 and 43. $^1$H NMR (300 MHz, CDCl$_3$) δ 8.13 (d, J=8.29 Hz, 2H), 7.67 (dd, J=8.29, 15.07 Hz, 4H), 7.38 (d, J=8.29 Hz, 2H), 7.14 (s, 1H), 6.49 (s, 1H), 4.03-4.19 (m, 2H), 3.55 (s, 2H), 1.13-1.77 (m, 13H). MS m/e 551.2 (M+H).

Example 44

2-[2-[(2-Cyclohexyl-ethyl)-(4-trifluoromethyl-phenyl)-amino]-6-(4-trifluoromethyl-phenyl)-pyridin-4-yl]-4-methyl-pentanoic acid

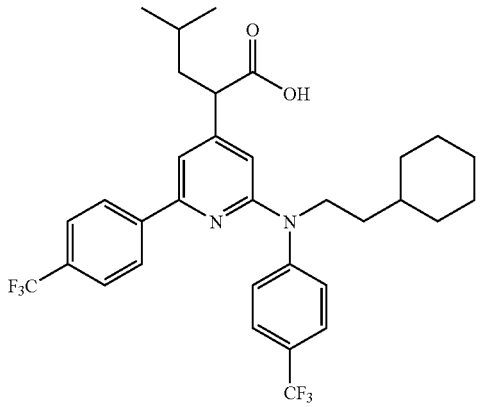

The title compound was prepared using 2-cyclohexylethylbromide in place of 3-bromo-2-methylpropene as described in Example 41. $^1$H NMR (300 MHz, CDCl$_3$) δ 8.12 (d, J=7.91 Hz, 2H), 7.69 (d, J=8.29 Hz, 2H), 7.63 (d, J=8.29 Hz, 2H), 7.36 (d, J=8.29 Hz, 2H), 7.17 (s, 1H), 6.56 (s, 1H), 4.07-4.17 (m, 2H), 3.55 (t, J=7.72 Hz, 1H), 1.13-1.96 (m, 16H), 0.90 (dd, J=4.33, 6.59 Hz, 6H). MS m/e 607.3 (M+H).

Example 45

4-Methyl-2-[2-[(2-piperidin-1-yl-ethyl)-(4-trifluoromethyl-phenyl)-amino]-6-(4-trifluoromethyl-phenyl)-pyridin-4-yl]-pentanoic acid

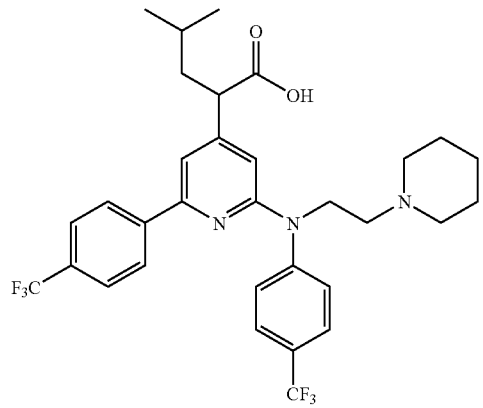

The title compound was prepared using N-(2-bromoethyl)piperidine hydrobromide in place of 3-bromo-2-methylpropene as described in Example 41. $^1$H NMR (300 MHz, CD$_3$OD) δ 8.06 (d, J=8.29 Hz, 2H), 7.67 (d, J=8.29 Hz, 2H), 7.59 (d, J=8.29 Hz, 2H), 7.19-7.38 (m, 3H), 6.62 (s, 1H), 4.27 (t, J=6.78 Hz, 2H), 3.40 (m, 3H), 3.13 (t, J=6.78 Hz, 4H), 1.09-1.66 (m, 9H), 0.76-0.85 (m, 6H). MS m/e 622.3 (M+Na).

Example 46

2-[2-[(4-tert-Butyl-phenyl)-(3-methyl-butyl)-amino]-6-(4-trifluoromethyl-phenyl)-pyridin-4-yl]-4-methyl-pentanoic acid

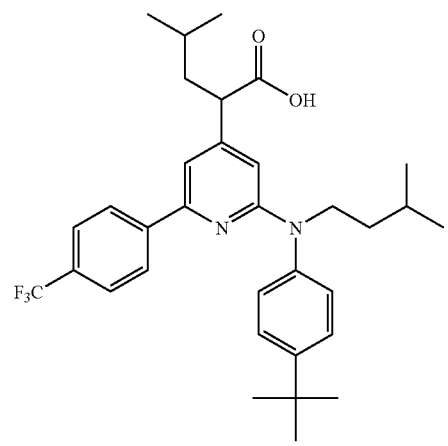

The title compound was prepared using 3-methyl-iodobutane in place of 3-bromo-2-methylpropene and 4-tert-butylaniline in place of 4-trifluoromethylaniline as described in Example 41. $^1$H NMR (300 MHz, CDCl$_3$) δ 8.15 (d, J=8.29 Hz, 2H), 7.68 (d, J=8.29 Hz, 2H), 7.41 (d, J=8.67 Hz, 2H), 7.15 (d, J=8.67 Hz, 2H), 7.06 (s, 1H), 6.28 (s, 1H), 3.98-4.08 (m, 2H), 3.45 (t, J=7.72 Hz, 1H), 1.77-1.86 (m, 1H), 1.55-1.70 (m, 4H), 1.40-1.53 (m, 1H), 1.35 (s, 9H), 0.90-0.98 (m, 6H), 0.85 (t, J=6.22 Hz, 6H). MS m/e 555.3 (M+H).

Example 47

[2-[(4-tert-Butyl-phenyl)-(3-methyl-butyl)-amino]-6-(4-trifluoromethyl-phenyl)-pyridin-4-yl]-acetic acid

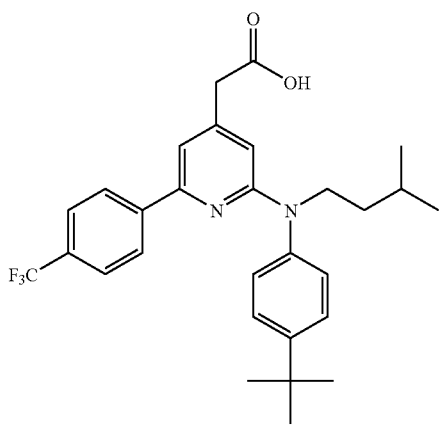

The title compound was prepared using 3-methyl-iodobutane in place of 3-bromo-2-methylpropene and 4-tert-butylaniline in place of 4-trifluoromethylaniline as described in Examples 41 and 43. $^1$H NMR (300 MHz, CDCl$_3$) δ 8.16 (d, J=8.29 Hz, 2H), 7.68 (d, J=8.29 Hz, 2H), 7.43 (d, J=8.67 Hz, 2H), 7.17 (d, J=8.67 Hz, 2H), 7.02 (s, 1H), 6.22 (s, 1H), 4.05 (d, J=15.07 Hz, 2H), 3.48 (s, 2H), 1.63 (dd, J=6.03, 8.29 Hz, 3H), 1.36 (s, 9H), 0.92-0.98 (m, 6H). MS m/e 499.4 (M+H).

Biological Activity

Screening of the Compounds of the Invention for γ-Secretase-Modulating Activity

Screening was carried out using SKNBE2 cells carrying the APP 695-wild type, grown in DMEM/NUT-mix F12 (HAM) provided by Gibco (cat no. 31330-38) containing 5% Serum/Fe supplemented with 1% non-essential amino acids.

Cells were grown to near confluency.

The screening was performed using the assay as described in Citron et al (1997) Nature Medicine 3: 67.

Examples of the γ-secretase modulating activity of representative products of the invention are shown in the following table.

| # | JNJ # | Chemical name | EC$_{50}$ μM | % inhibition @ 1 uM |
|---|---|---|---|---|
| 1 | 40885156 | 2-[2,6-Bis-(4-trifluoromethyl-phenyl)-pyridin-4-yl]-4-methyl-pentanoic acid | 0.26 | |
| 2 | 40885130 | 2-[2-(4-Fluoro-phenyl)-6-(4-trifluoromethyl-phenyl)-pyridin-4-yl]-4-methyl-pentanoic acid | | 28 |
| 3 | 40868932 | 4-Methyl-2-[2-(4-trifluoromethoxy-phenyl)-6-(4-trifluoromethyl-phenyl)-pyridin-4-yl]-pentanoic acid | 0.38 | |
| 4 | CZC18909 | 2-[2-(4-Methoxy-phenyl)-6-(4-trifluoromethyl-phenyl)-pyridin-4-yl]-4-methyl-pentanoic acid | | 1 |
| 5 | CZC18908 | 4-Methyl-2-[2-(4-trifluoromethyl-phenyl)-6-(3,4,5-trifluoro-phenyl)-pyridin-4-yl]-pentanoic acid | — | — |
| 6 | 41023151 | 2-[2-(3,5-Bis-trifluoromethyl-phenyl)-6-(4-trifluoromethyl-phenyl)-pyridin-4-yl]-4-methyl-pentanoic acid | 0.27 | |
| 7 | 40875081 | 4-Methyl-2-[2-quinolin-3-yl-6-(4-trifluoromethyl-phenyl)-pyridin-4-yl]-pentanoic acid | 0.67 | |
| 8 | 40789177 | 2-[2-(3-Fluoro-5-trifluoromethyl-phenyl)-6-(4-trifluoromethyl-phenyl)-pyridin-4-yl]-4-methyl-pentanoic acid | 0.12 | |
| 9 | 40822743 | 2-[2-(4-Isopropyl-phenyl)-6-(4-trifluoromethyl-phenyl)-pyridin-4-yl]-4-methyl-pentanoic acid | 0.73 | |
| 10 | 40532102 | 2-[2-(3,5-Difluoro-phenyl)-6-(4-trifluoromethyl-phenyl)-pyridin-4-yl]-4-methyl-pentanoic acid | 0.2 | |
| 11 | 40532154 | 4-Methyl-2-[2-p-tolyl-6-(4-trifluoromethyl-phenyl)-pyridin-4-yl]-pentanoic acid | | 0 |
| 12 | 40489748 | 4-Methyl-2-[2-(3-trifluoromethyl-phenyl)-6-(4-trifluoromethyl-phenyl)-pyridin-4-yl]-pentanoic acid | | 32 |
| 13 | 40532167 | 2-[2-Biphenyl-4-yl-6-(4-trifluoromethyl-phenyl)-pyridin-4-yl]-4-methyl-pentanoic acid | | 49 |
| 14 | 40532141 | 4-Methyl-2-[2-naphthalen-2-yl-6-(4-trifluoromethyl-phenyl)-pyridin-4-yl]-pentanoic acid | | 34 |
| 15 | 40878422 | 4-Methyl-2-[2-naphthalen-2-yl-6-(4-trifluoromethyl-phenyl)-pyridin-4-yl]-pent-4-enoic acid | | 19 |
| 16 | 40545336 | 2-[2-(2,4-Bis-trifluoromethyl-phenyl)-6-(4-trifluoromethyl-phenyl)-pyridin-4-yl]-4-methyl-pent-4-enoic acid | | 23 |
| 17 | 40837238 | 2-[2-(2,4-Bis-trifluoromethyl-phenyl)-6-(4-trifluoromethyl-phenyl)-pyridin-4-yl]-4-methyl-pentanoic acid | | 64 |

-continued

| # | JNJ # | Chemical name | EC$_{50}$ μM | % inhibition @ 1 uM |
|---|---|---|---|---|
| 18 | 40824381 | 2-[2-Isoquinolin-4-yl-6-(4-trifluoromethyl-phenyl)-pyridin-4-yl]-4-methyl-pent-4-enoic acid | | 14 |
| 19 | 40837264 | 2-[2-Isoquinolin-4-yl-6-(4-trifluoromethyl-phenyl)-pyridin-4-yl]-4-methyl-pentanoic acid | | 14 |
| 20 | 40837277 | 2-[2-(2,3-Difluoro-phenyl)-6-(4-trifluoromethyl-phenyl)-pyridin-4-yl]-4-methyl-pent-4-enoic acid | | 9 |
| 21 | 40878396 | 2-[2-(2,3-Difluoro-phenyl)-6-(4-trifluoromethyl-phenyl)-pyridin-4-yl]-4-methyl-pentanoic acid | | 12 |
| 22 | 40479660 | 2-[2-(2,4-Difluoro-phenyl)-6-(4-trifluoromethyl-phenyl)-pyridin-4-yl]-4-methyl-pentanoic acid | | 5 |
| 23 | 40532115 | 2-[2-(2,4-Difluoro-phenyl)-6-(4-trifluoromethyl-phenyl)-pyridin-4-yl]-4-methyl-pent-4-enoic acid | | 0 |
| 24 | 40879553 | 2-[2-(2,5-Difluoro-phenyl)-6-(4-trifluoromethyl-phenyl)-pyridin-4-yl]-4-methyl-pent-4-enoic acid | | 22 |
| 25 | 41124707 | 2-[2-(2,5-Difluoro-phenyl)-6-(4-trifluoromethyl-phenyl)-pyridin-4-yl]-4-methyl-pentanoic acid | | 19 |
| 26 | 40824394 | 2-[2-(2,6-Difluoro-phenyl)-6-(4-trifluoromethyl-phenyl)-pyridin-4-yl]-4-methyl-pentanoic acid | | 2 |
| 27 | 40852435 | 2-[2-(2,6-Difluoro-phenyl)-6-(4-trifluoromethyl-phenyl)-pyridin-4-yl]-4-methyl-pent-4-enoic acid | | 5 |
| 28 | 40852422 | 2-[2-Benzo[b]thiophen-2-yl-6-(4-trifluoromethyl-phenyl)-pyridin-4-yl]-4-methyl-pent-4-enoic acid | | 0 |
| 29 | 40852409 | 2-[2-Benzo[b]thiophen-2-yl-6-(4-trifluoromethyl-phenyl)-pyridin-4-yl]-4-methyl-pentanoic acid | | 57 |
| 30 | 40837316 | 4-Methyl-2-[6'-trifluoromethyl-6-(4-trifluoromethyl-phenyl)-[2,3']bipyridinyl-4-yl]-pentanoic acid | | 0 |
| 31 | 40837290 | 4-Methyl-2-[6'-trifluoromethyl-6-(4-trifluoromethyl-phenyl)-[2,3']bipyridinyl-4-yl]-pent-4-enoic acid | | 59 |
| 32 | 40824394 | 4-Methyl-2-[2-p-tolyl-6-(4-trifluoromethyl-phenyl)-pyridin-4-yl]-pent-4-enoic acid | | 7 |
| 33 | 40824355 | 2-[2-Benzo[1,3]dioxol-5-yl-6-(4-trifluoromethyl-phenyl)-pyridin-4-yl]-4-methyl-pentanoic acid | | 20 |
| 34 | 40824342 | 2-[2-Biphenyl-3-yl-6-(4-trifluoromethyl-phenyl)-pyridin-4-yl]-4-methyl-pent-4-enoic acid | | 16 |
| 35 | 40515450 | 2-[2-Biphenyl-3-yl-6-(4-trifluoromethyl-phenyl)-pyridin-4-yl]-4-methyl-pentanoic acid | | 53 |
| 36 | 40815463 | 2-[2-(3-Isobutoxy-phenyl)-6-(4-trifluoromethyl-phenyl)-pyridin-4-yl]-4-methyl-pentanoic acid | | 41 |
| 37 | 40792232 | 4-Methyl-2-[2-(4-phenoxy-phenyl)-6-(4-trifluoromethyl-phenyl)-pyridin-4-yl]-pentanoic acid | | 73 |
| 38 | 40587144 | 4-Methyl-2-[2-phenyl-6-(4-trifluoromethyl-phenyl)-pyridin-4-yl]-pentanoic acid | | 8 |
| 39 | 40586884 | 2-[2-(4-Methanesulfonyl-phenyl)-6-(4-trifluoromethyl-phenyl)-pyridin-4-yl]-4-methyl-pentanoic acid | | 18 |
| 40 | 40586871 | 2-[2-[Isobutyl-(4-trifluoromethyl-phenyl)-amino]-6-(4-trifluoromethyl-phenyl)-pyridin-4-yl]-4-methyl-pentanoic acid | 0.34 | |
| 41 | 40579968 | 4-Methyl-2-[2-[(3-methyl-butyl)-(4-trifluoromethyl-phenyl)-amino]-6-(4-trifluoromethyl-phenyl)-pyridin-4-yl]-pentanoic acid | 0.3 | |
| 42 | 40577576 | [2-[(3-Methyl-butyl)-(4-trifluoromethyl-phenyl)-amino]-6-(4-trifluoromethyl-phenyl)-pyridin-4-yl]-acetic acid | | 36 |
| 43 | 40577420 | [2-[(2-Cyclohexyl-ethyl)-(4-trifluoromethyl-phenyl)-amino]-6-(4-trifluoromethyl-phenyl)-pyridin-4-yl]-acetic acid | | 56 |
| 44 | 40571180 | 2-[2-[(2-Cyclohexyl-ethyl)-(4-trifluoromethyl-phenyl)-amino]-6-(4-trifluoromethyl-phenyl)-pyridin-4-yl]-4-methyl-pentanoic acid | 0.64 | |

-continued

| # | JNJ # | Chemical name | EC$_{50}$ μM | % inhibition @ 1 uM |
|---|---|---|---|---|
| 45 | 40571154 | 4-Methyl-2-[2-[(2-piperidin-1-yl-ethyl)-(4-trifluoromethyl-phenyl)-amino]-6-(4-trifluoromethyl-phenyl)-pyridin-4-yl]-pentanoic acid | | 20 |
| 46 | 40569932 | 2-[2-[(4-tert-Butyl-phenyl)-(3-methyl-butyl)-amino]-6-(4-trifluoromethyl-phenyl)-pyridin-4-yl]-4-methyl-pentanoic acid | | 22 |
| 47 | 40569919 | [2-[(4-tert-Butyl-phenyl)-(3-methyl-butyl)-amino]-6-(4-trifluoromethyl-phenyl)-pyridin-4-yl]-acetic acid | 1.29 | |

While the foregoing specification teaches the principles of the present invention, with examples provided for the purpose of illustration, it will be understood that the practice of the invention encompasses all of the usual variations, adaptations and/or modifications as come within the scope of the following claims and their equivalents. All publications disclosed in the above specification are hereby incorporated by reference in full.

The invention claimed is:

1. A compound having the general Formula (I)

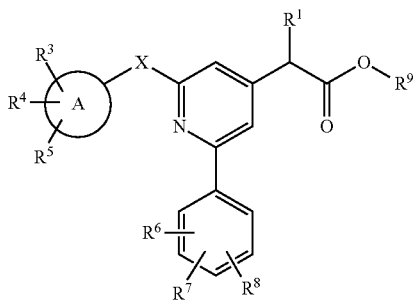

wherein:
A is phenyl, pyridyl, napthyl, biphenyl, quinolinyl, isoquinolinyl, or benzo[b]thiophen-2-yl, alternatively, A is taken together with $R^3$, $R^4$, and $R^5$, and is selected from the group consisting of:

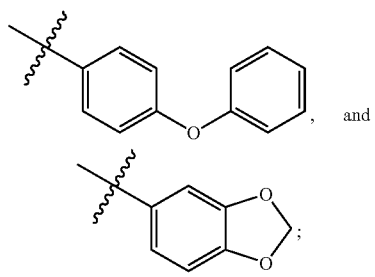

$R^1$ is H, $C_{(1-5)}$alkyl, or $C_{(1-5)}$alkenyl;
X is a direct bond, or —$NR^2$—;
  wherein $R^2$ is $C_{(1-5)}$alkyl optionally substituted with $C_{(1-6)}$cycloalkyl or $C_{(1-6)}$heterocyclyl;
$R^3$ is H, $CF_3$, F, $OCF_3$, $C_{(1-4)}$alkyl, —$OC_{(1-4)}$alkyl, or —$SO_2CH_3$;
$R^4$ is H, $CF_3$, F, $OCF_3$, $C_{(1-4)}$alkyl, —$OC_{(1-4)}$alkyl, or —$SO_2CH_3$;
$R^5$ is H, $CF_3$, F, $OCF_3$, $C_{(1-4)}$alkyl, —$OC_{(1-4)}$alkyl, or —$SO_2CH_3$;
$R^6$ is F, $OCF_3$, or $CF_3$;
$R^7$ is H, F, $OCF_3$, or $CF_3$;
$R^8$ is H, F, $OCF_3$, or $CF_3$;
and
$R^9$ is H, or $C_{(1-4)}$alkyl;
or an ester or pharmaceutically acceptable salt thereof.

2. A compound of claim 1, wherein:
A is phenyl, pyridyl, napthyl, or biphenyl, alternatively, A is taken together with $R^3$, $R^4$, and $R^5$, and is selected from the group consisting of:

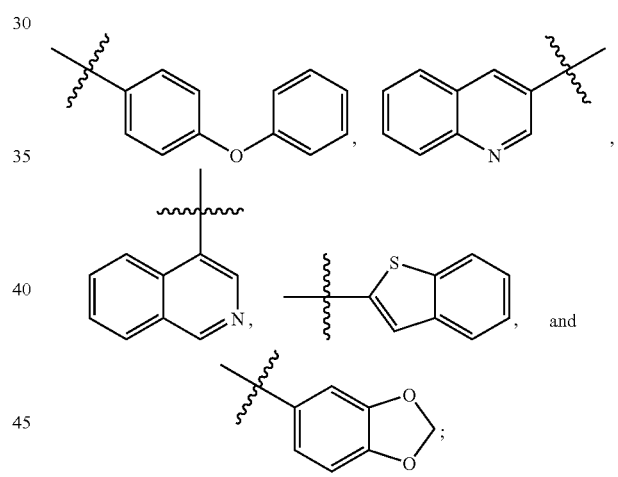

X is a direct bond, or —$NR^2$—;
  wherein $R^2$ is $C_{(1-5)}$alkyl optionally substituted with cyclohexyl or piperidinyl;
$R^3$ is $CF_3$, F, $OCF_3$, $C_{(1-4)}$alkyl, —$OC_{(1-4)}$alkyl, or —$SO_2CH_3$;
$R^4$ is H, F, $OCF_3$, or $CF_3$;
$R^5$ is H, F, $OCF_3$, or $CF_3$;
$R^6$ is F, or $CF_3$;
$R^7$ is H, or F;
$R^8$ is H, or F;
and
$R^9$ is H;
or an ester or pharmaceutically acceptable salt thereof.

3. A compound of claim 2, wherein:
A is phenyl or pyridyl, alternatively, A is taken together with $R^3$, $R^4$, and $R^5$, and is selected from the group consisting of:

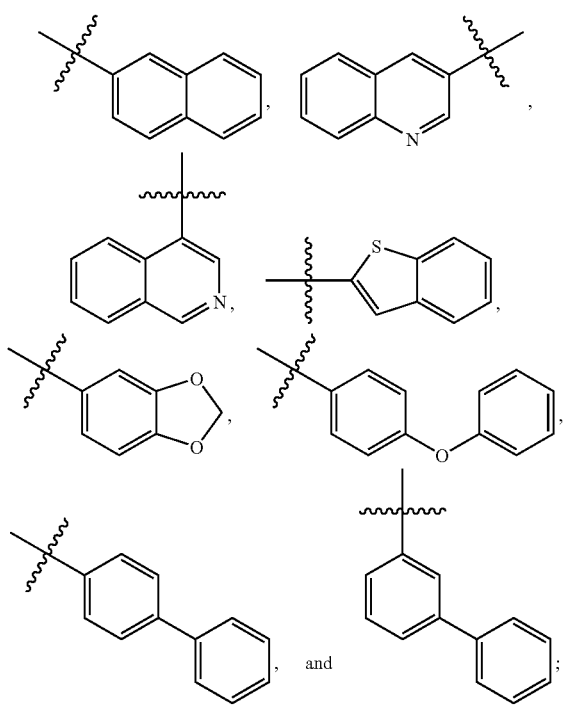

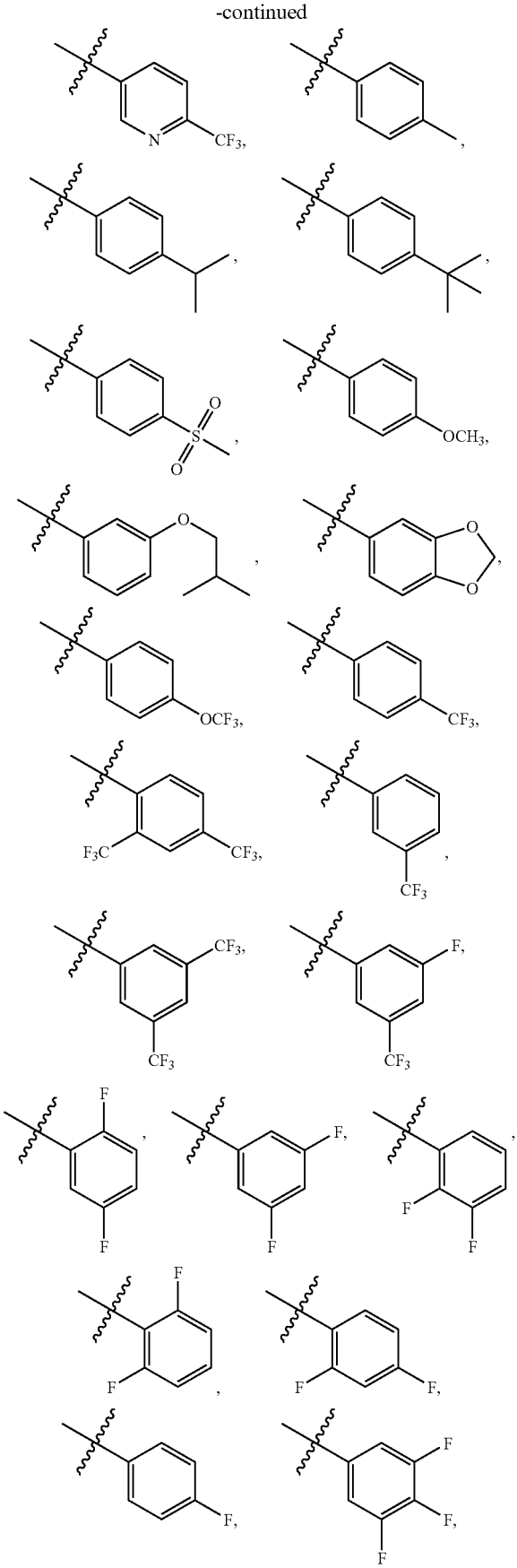

$R^1$ is selected from the group consisting of H, —$CH_2CH(CH_3)_2$, and 2-methyl 1-propen-3-yl;

X is a direct bond, or —$NR^2$—;
   wherein $R^2$ is selected from the group consisting of alkyl selected from the group consisting of —$CH_2CH(CH_3)_2$, —$CH_2CH_2CH(CH_3)_2$, and ethyl, wherein said ethyl is substituted with cyclohexyl or piperidinyl;

$R^3$ is $CF_3$, F, $OCF_3$, $OCH_3$, $CH_3$, isopropyl, tert-butyl, —$OCH_2CH(CH_3)_2$, or —$SO_2CH_3$;

$R^4$ is H, F, or $CF_3$;

$R^5$ is H, or F;

$R^6$ is $CF_3$;

$R^7$ is H;

and $R^8$ is H;

or an ester or pharmaceutically acceptable salt thereof.

4. A compound of claim 3, wherein:

A is taken together with $R^3$, $R^4$, and $R^5$, and is selected from the group consisting of:

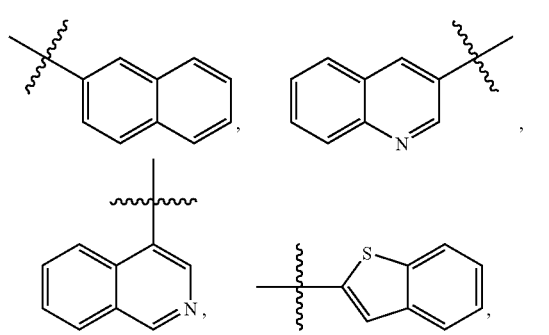

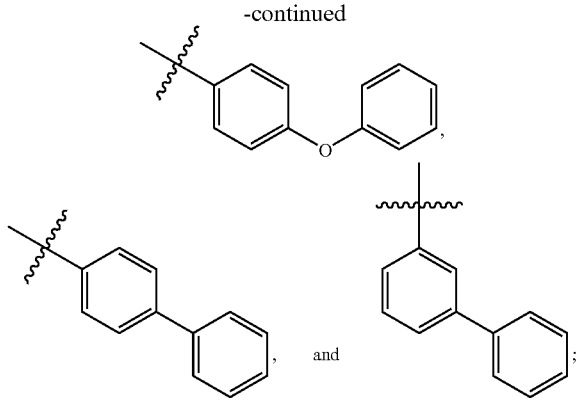
or an ester or pharmaceutically acceptable salt thereof.
5. A compound selected from the group consisting of:
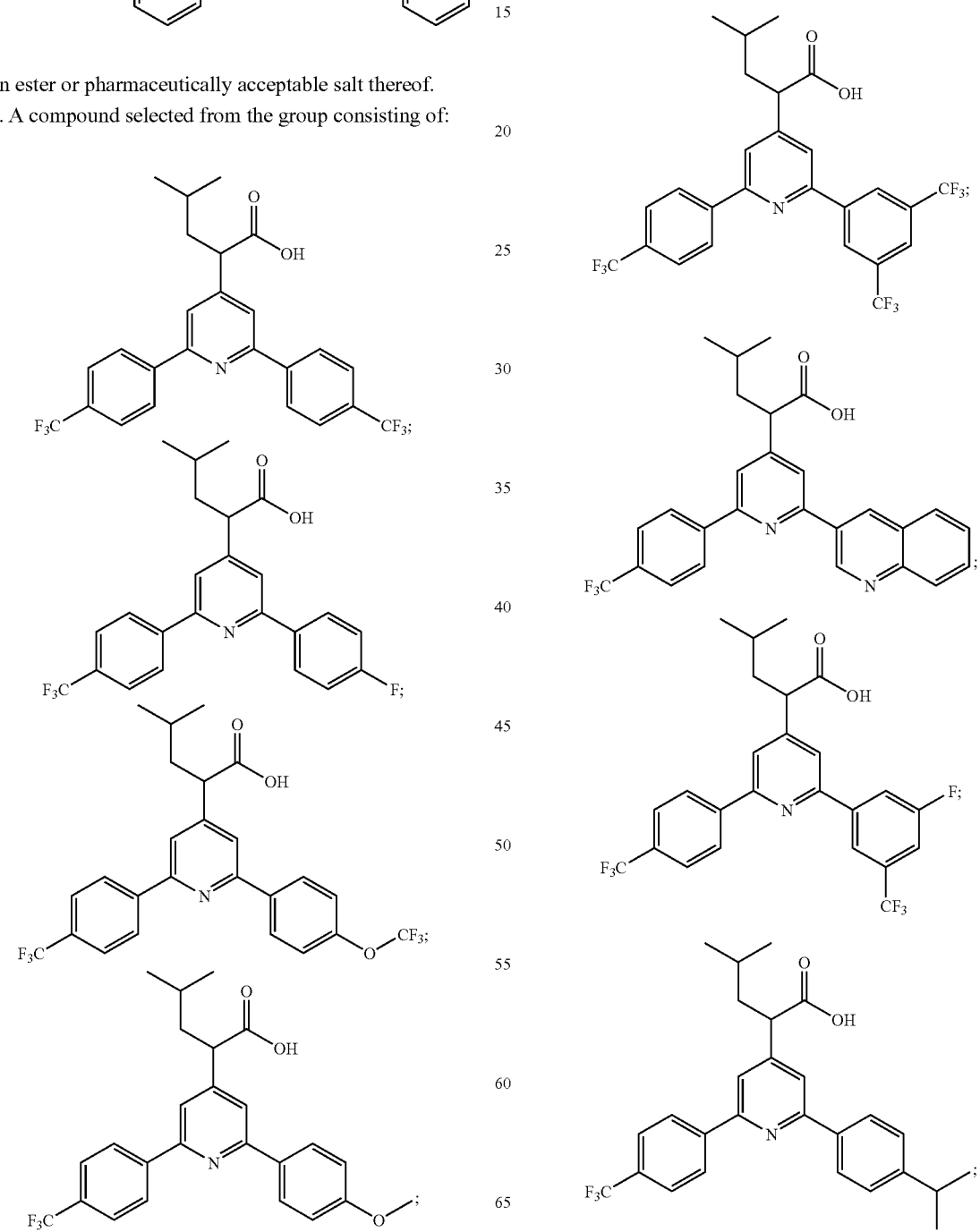

75
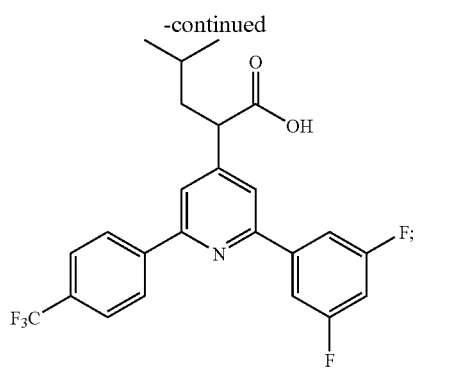
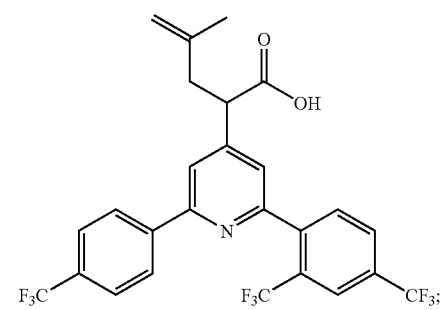
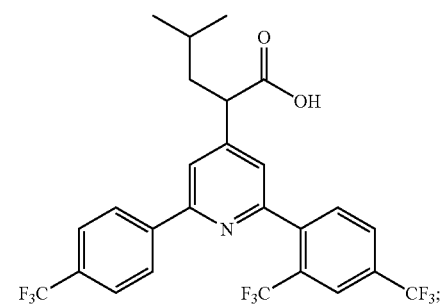
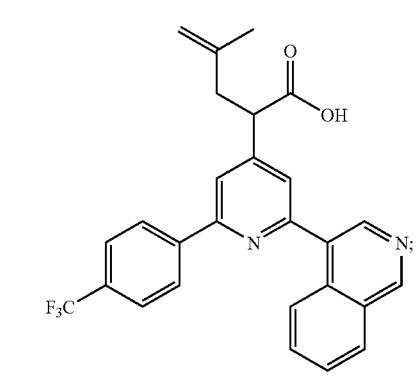
76
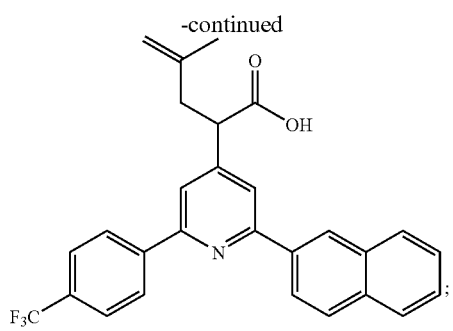
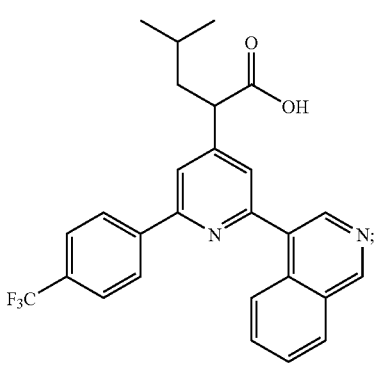

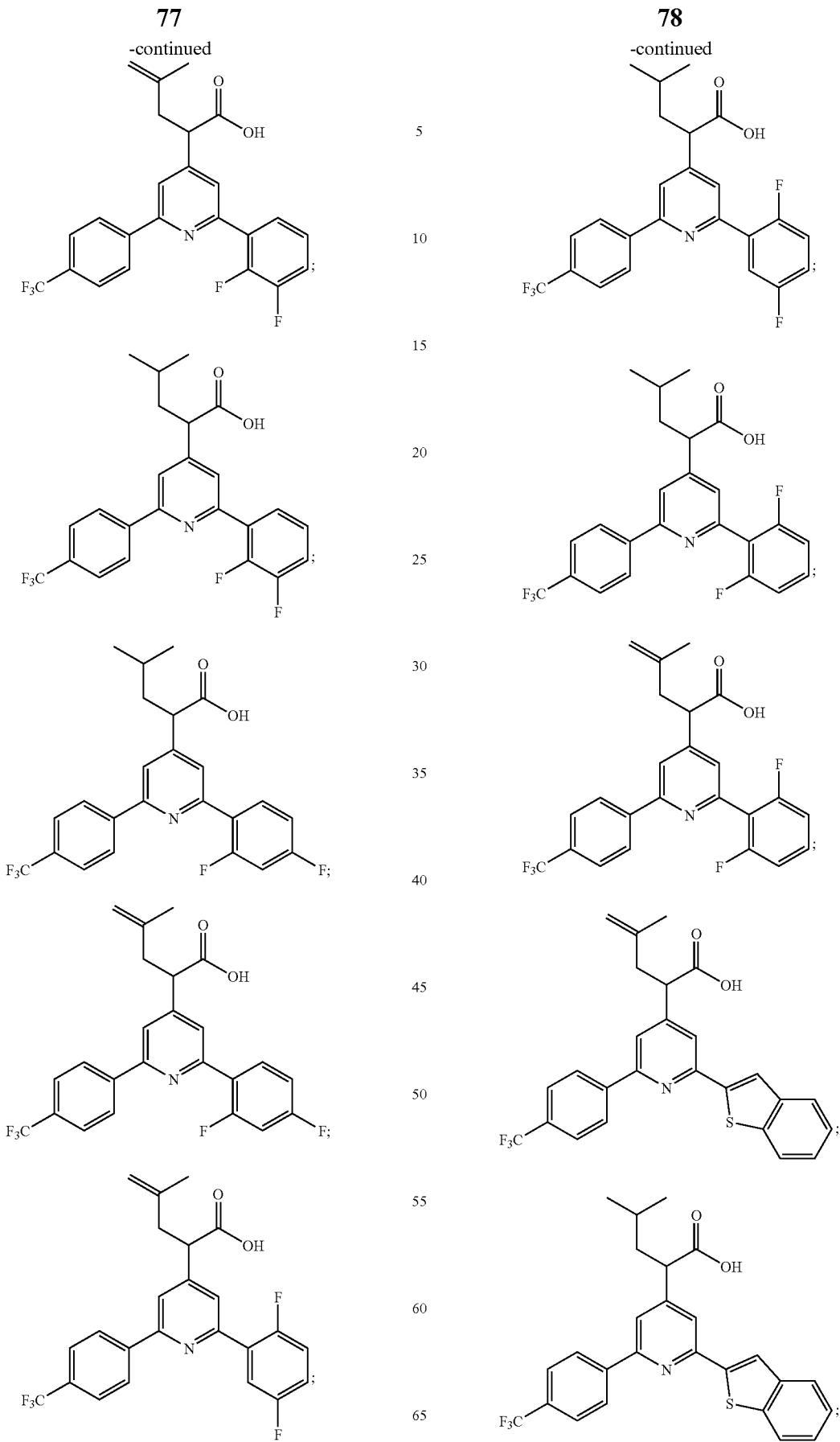

-continued
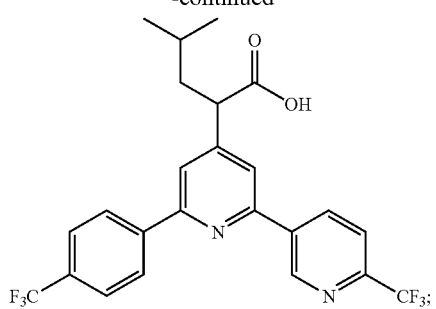
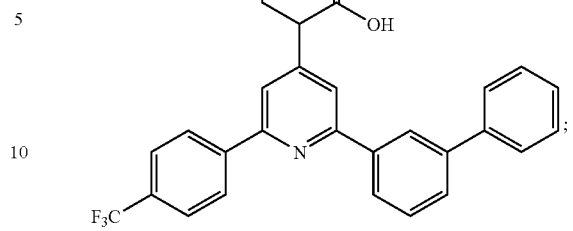
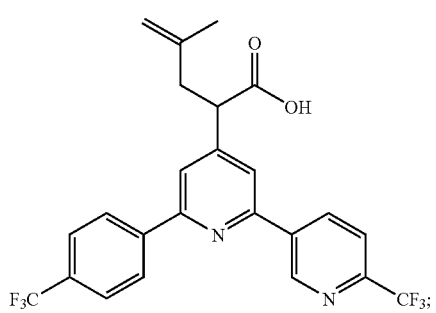
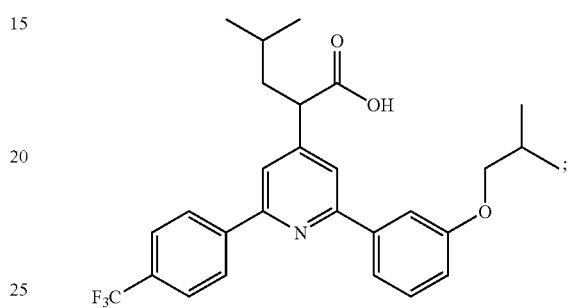
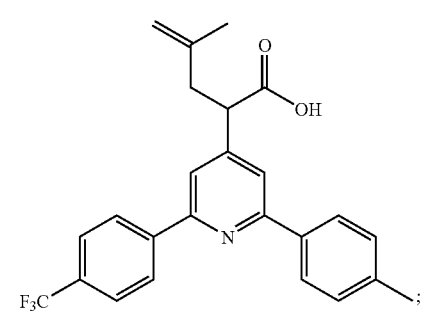
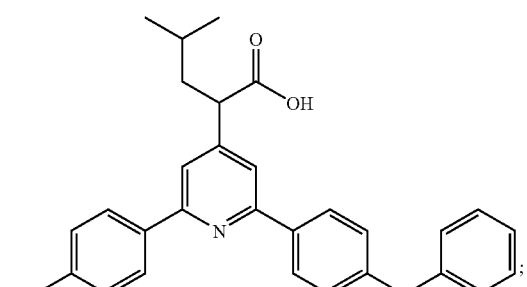
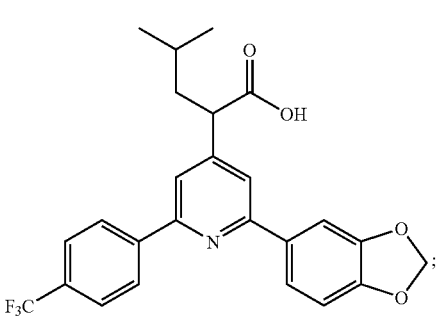
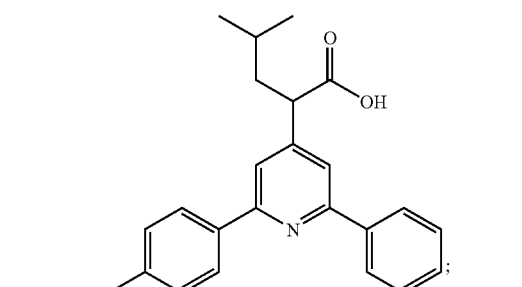
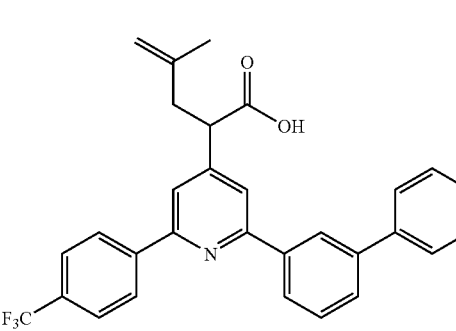
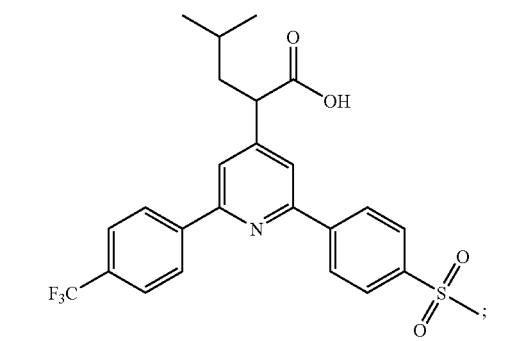

81
-continued
82
-continued

or an ester or pharmaceutically acceptable salt thereof.

6. A pharmaceutical composition comprising a compound according to any of claims 1 to 5 in admixture with an inert carrier.

7. A method of treating Alzheimer's disease in a mammal, comprising administering to the mammal a therapeutically effective amount of a compound according to any of claims 1 to 5.

8. The compound according to claim 1 wherein $R^9$ is H, $C_5$ alkyl, or $C_{(1-5)}$alkenyl.

* * * * *